United States Patent
Stogniew et al.

(10) Patent No.: US 9,688,679 B2
(45) Date of Patent: Jun. 27, 2017

(54) 7-BENZYL-4-(METHYLBENZYL)-2,4,6,7,8,9-HEXAHYDROIMIDAZO[1,2-A]PYRIDO[3,4-E]PYRIMIDIN-5 (1H)-ONE, SALTS THEREOF AND METHODS OF USING THE SAME IN COMBINATION THERAPY

(71) Applicants: Oncoceutics, Inc., Philadelphia, PA (US); PROVID PHARMACEUTICALS INC., Monmouth Junction, NJ (US)

(72) Inventors: Martin Stogniew, Blue Pell, PA (US); Joshua E. Allen, Cambridge, MA (US)

(73) Assignee: Oncoceutics, Inc., Philadelphia, PA (US)

( * ) Notice: Subject to any disclaimer, the term of this patent is extended or adjusted under 35 U.S.C. 154(b) by 0 days.

(21) Appl. No.: 15/036,210

(22) PCT Filed: Sep. 12, 2014

(86) PCT No.: PCT/US2014/055373
§ 371 (c)(1),
(2) Date: May 12, 2016

(87) PCT Pub. No.: WO2015/073109
PCT Pub. Date: May 21, 2015

(65) Prior Publication Data
US 2016/0264574 A1  Sep. 15, 2016

Related U.S. Application Data

(63) Continuation-in-part of application No. 14/341,392, filed on Jul. 25, 2014, now Pat. No. 9,376,437, which is a continuation-in-part of application No. 14/208,657, filed on Mar. 13, 2014, now Pat. No. 9,265,765, application No. PCT/US2014/055373, which is a continuation-in-part of application No. PCT/US2014/048241, filed on Jul. 25, 2014, and a continuation-in-part of application No. 14/208,657.

(60) Provisional application No. 61/904,718, filed on Nov. 15, 2013, provisional application No. 61/779,828, filed on Mar. 13, 2013.

(51) Int. Cl.
| | |
|---|---|
| *A61K 31/337* | (2006.01) |
| *A61K 31/395* | (2006.01) |
| *A61K 31/4188* | (2006.01) |
| *A61K 31/4545* | (2006.01) |
| *A61K 31/513* | (2006.01) |
| *A61K 31/519* | (2006.01) |
| *C07D 471/14* | (2006.01) |
| *A61K 45/06* | (2006.01) |

(52) U.S. Cl.
CPC .......... *C07D 471/14* (2013.01); *A61K 31/337* (2013.01); *A61K 31/395* (2013.01); *A61K 31/4188* (2013.01); *A61K 31/4545* (2013.01); *A61K 31/513* (2013.01); *A61K 31/519* (2013.01); *A61K 45/06* (2013.01)

(58) Field of Classification Search
CPC ................ A61K 31/337; A61K 31/395; A61K 31/4188; A61K 31/4545; A61K 31/513; A61K 31/519
See application file for complete search history.

(56) References Cited

U.S. PATENT DOCUMENTS

| | | |
|---|---|---|
| 4,642,345 A | 2/1987 | Temple, Jr. |
| 7,635,690 B2 | 12/2009 | Schinazi et al. |
| 2004/0067953 A1 | 4/2004 | Stein et al. |
| 2007/0149571 A1 | 6/2007 | Stein et al. |
| 2008/0221135 A1 | 9/2008 | Voi |
| 2008/0254040 A1 | 10/2008 | Stefanic et al. |
| 2010/0266540 A1 | 10/2010 | Craven |
| 2011/0287001 A1 | 11/2011 | Holland et al. |
| 2012/0128732 A1 | 5/2012 | Trieu et al. |
| 2012/0276088 A1 | 11/2012 | El-Deiry et al. |

(Continued)

FOREIGN PATENT DOCUMENTS

| | | |
|---|---|---|
| DE | 2150062 | 4/1973 |
| WO | WO 2015/153468 A1 | 10/2015 |

OTHER PUBLICATIONS

Allen et al. "Dual Inactivation of Akt and ERK by TIC10 Signals Foxo3a Nuclear Translocation, TRAIL Gene Induction, and Potent Antitumor Effects", www.sciencetranslationmedicine.org vol. 5 Issue 171, 2013.

(Continued)

*Primary Examiner* — Yong Chong
(74) *Attorney, Agent, or Firm* — Mark S. Cohen; Pearl Cohen Zedek Latzer Baratz LLP

(57) ABSTRACT

This disclosure relates, at least in part, to a method of treatment. In one embodiment, the method of treatment comprises administering to a subject in need of such treatment a first therapeutic agent including compound (1): (structurally represented) or a pharmaceutically acceptable salt thereof in combination with a second therapeutic agent, wherein the first therapeutic agent and the second therapeutic agent are administered either simultaneously or sequentially.

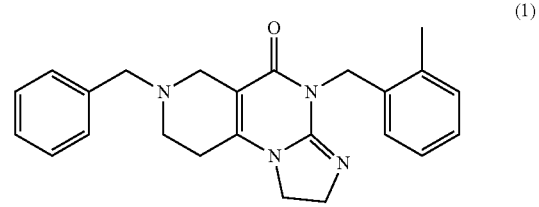

4 Claims, 1 Drawing Sheet

(56) References Cited

U.S. PATENT DOCUMENTS

2013/0172314 A1 7/2013 Chen et al.
2013/0209518 A1 8/2013 Desai et al.

OTHER PUBLICATIONS

Allen et al. "First-In-Class Small Molecule ONC201 Induces DR5 and Cell Death in Tumor but Not Normal Cells to Provide a Wide Therapeutic Index as an Anti-Cancer Agent" PLoS One. Nov. 18, 2015;10(11):e0143082.
Allen et al. "Identification of TRAIL-inducing compounds highlights small molecule ONC201/TIC10 as a unique anti-cancer agent that activates the TRAIL pathway" Mol Cancer. May 1, 2015;14:99.
Allen et al. "Genetic and Pharmacological Screens Converge in Identifying FLIP, BCL2, and IAP Proteins as Key Regulators of Sensitivity to the TRAIL-Inducing Anticancer Agent ONC201/TIC10" Cancer Res. Apr. 15, 2015;75(8):1668-74.
Allen et al. "The small molecule TIC10 has potent anticancer efficacy mediated by induction of TRAIL production in normal and tumor cells" Cancer Research. Apr. 15, 2011;71(8 Supplement):4502-.
Allen et al. "ONC201 Possesses a Benign Safety Profile at Highly Efficacious Doses in Normal Human Cells and Animal Toxicology Studies" Blood. Dec. 6, 2014;124(21):4812-; Abstract.
Allen et al. "ONC201 (TIC10) Induces TRAIL and Cell Death in Preclinical Models of Pediatric Lymphoma" Blood. Nov. 15, 2013;122(21):1671-; Abstract.
Allen et al. "Kinase library siRNA screen identifies KSR1 as a synergistic therapeutic target in combination with TIC10" Cancer Research. Apr. 15, 2013;73(8 Supplement):2059-; Abstract.
Allen et al. "Potent anti-tumor effects of TIC10 require Foxo3a and TRAIL gene upregulation" Cancer Research. Apr. 15, 2012;72(8 Supplement):1935-; Abstract.
Imperato GH, Allen JE, El-Deiry WS. Characterization of TIC10, a novel small molecule inducer of TRAIL, in combination with chemotherapy for lymphoma in vitro. Cancer Research. Apr. 15, 2013;73(8 Supplement):2949; Abstract.
Interational Search Report for PCT Appl. No. PCT/US14/25885 Mailed on Jul. 3, 2014.
Interational Search Report for PCT Appl. No. PCT/US14/48241 Mailed on Oct. 29, 2014.
Interational Search Report for PCT Appl. No. PCT/US2014/55373 Mailed on Nov. 24, 2014.
Ishizawa et al. "ATF4 induction through an atypical integrated stress response to ONC201 triggers p53-independent apoptosis in hematological malignancies" Sci Signal. Feb. 16, 2016;9(415):ra17.
Ishizawa et al. "ONC201 induces p53-independent apoptosis and cell cycle arrest in hematological malignancies and leukemic stem/progenitor cells by inducing ER stress and mTOR inhibition" Blood. Dec. 6, 2014;124(21):3122-; Abstract.
Jacob et al. "Pharmacophore reassignment for induction of the immunosurveillance cytokine TRAIL", Angew Chem Int Ed Engl. Jun. 23, 2014;53(26):6628-31.
Karpel-Massler et al. "TIC10/ONC201 synergizes with Bcl-2/Bcl-xL inhibition in glioblastoma by suppression of Mcl-1 and its binding partners in vitro and in vivo" Oncotarget. Nov. 3, 2015;6(34):36456-71.
Kline et al. "ONC201 kills solid tumor cells by triggering an integrated stress response dependent on ATF4 activation by specific eIF2α kinases" Sci. Signal.. Feb. 16, 2016;9(415):ra18-.
Kojima et al. "ONC201 Exerts p53-Independent Cytotoxicity Through TRAIL and DR5 Induction in Mantle Cell Lymphomas" Blood, Nov. 15, 2013;122(21):3822-; Abstract.
Lulla et al. "Caspase-Dependent Anti-Tumor Effects of ONC201/TIC10 on Acute Myeloid Leukemia (AML) and Multiple Myeloma (MM)" Blood. Dec. 6, 2014;124(21);5224-; Abstract.
Prabhu et al. "Small-Molecule ONC201/TIC10 Targets Chemotherapy-Resistant Colorectal Cancer Stem-like Cells in an Akt/Foxo3a/TRAIL-Dependent Manner" Cancer Res. Apr. 1, 2015;75(7):1423-32; Abstract.
Prabhu et al. "ONC201 Depletes Cancer Stem Cells in Refractory Cancer Patient Samples" Blood. Dec. 6, 2014;124(21):5219-; Abstract.
Prabhu et al. "Small Molecule ONC201/TIC10 Induces Caspase-Dependent Apoptosis in Acute Lymphoblastic Leukemia Cells Via Modulation of Bcl-2 and IAP Family Proteins" Blood, Dec. 6, 2014;124(21):5237-; Abstract.
Prabhu et al. "Therapeutic targeting of colorectal cancer stem cells by TRAIL-inducing small molecule TIC10" Cancer Research. Apr. 15, 2013;73(8 Supplement):3732; Abstract.
Pubchem SureCN2018352, CID 5486859, pp. 1-3, Create Date: Aug. 9, 2005; p. 1; [retrieved on Sep. 19, 2014]. Retrieved from the Internet: <URL: https://pubchem.ncbi.nlm.nih.gov/summary/summary.cgi?cid=5486859&loc=ec_rcs>.
Pubchem CID 73777259, pp. 1-3, Create Date: May 26, 2014; p. 1; [retrieved on Sep. 19, 2014]. Retrieved from the Internet: <URL: https://pubchem.ncbi.nlm.nih.gov/summary/summary.cgi?cid=73777259&loc=ec_rcs>.
Talekar et al. "ONC201 induces cell death in pediatric non-Hodgkin's lymphoma cells" Cell Cycle. Aug. 3, 2015;14(15):2422-8.
Talekar et al. "ONC201/TIC10 Is Effective as a Monoagent and Synergizes with Chemotherapy to Induce Cell Death in Non-Hodgkin Lymphoma" Blood. Dec. 6, 2014;124(21):5491-; Abstract.
Talekar et al. "TRAIL-inducing agent-TIC10 and combinatorial therapeutics in pediatric lymphoma: a targeted approach" Abstract LB-307, Cancer Research. Apr. 15, 2013;73(8 Supplement):LB-307; Abstract.
Wagner et al., "The angular structure of ONC201, a TRAIL pathway-inducing compound, determines its potent anti-cancer activity", Oncotarget vol. 5, No. 24, Jan. 2015.
Wagner et al. "Screen of Small Molecule ONC201/TIC10 Identifies Single Agent Activity and Combinatorial Efficacy with Bortezomib, Rituximab or Dexamethasone in Killing of Acute Lymphoblastic Leukemia Cells" Blood. Dec. 6, 2014;124(21):5233-; Abstract.
Zhang et al. "The preclinical evaluation of TIC10/ONC201 as an anti-pancreatic cancer agent" Biochem Biophys Res Commun. Aug. 5, 2016;476(4):260-6.
Zhao et al. "ONC201, a small molecule Foxo3a activator, activity against patient-derived glioblastoma tumor-initiating cells" In ASCO Annual Meeting Proceedings May 20, 2014 (vol. 32, No. 15_suppl, p. e13022).
Forfar et al., "Reaction between 5-(phenoxymethyl)-2-amino-2-oxazoline and N-benzyl-3-(ethoxycarbonyl)-4-piperidinone hydrochloride: a structural investigation", Tetrahedron 55, 1999, pp. 12819-12828.

7-BENZYL-4-(METHYLBENZYL)-2,4,6,7,8,9-HEXAHYDROIMIDAZO[1,2-A]PYRIDO[3,4-E]PYRIMIDIN-5 (1H)-ONE, SALTS THEREOF AND METHODS OF USING THE SAME IN COMBINATION THERAPY

CROSS-REFERENCE TO RELATED APPLICATIONS

This application is a continuation-in-part of U.S. patent application Ser. No. 14/341,392, filed Jul. 25, 2014, and International Patent Application No. PCT/US2014/048241, filed Jul. 25, 2014, each of which is a continuation-in-part of U.S. patent application Ser. No. 14/208,657, filed Mar. 13, 2014, which in turn claims the benefit of U.S. Provisional Patent Application No. 61/779,828, filed Mar. 13, 2013, and U.S. Provisional Patent Application No. 61/904,718, filed Nov. 15, 2013, all of which are incorporated herein by reference in their entireties. This application is also a continuation-in-part of U.S. patent application Ser. No. 14/208,657, filed Mar. 13, 2014, and claims the benefit of U.S. Provisional Patent Application No. 61/904,718, filed Nov. 15, 2013.

BACKGROUND OF THE INVENTION

TNF-related apoptosis-inducing ligand (TRAIL; Apo2L) is an endogenous protein that selectively induces apoptosis in cancer cells. TRAIL is a powerful inducer of apoptosis in a wide range of human cancer cell lines via pro-apoptotic death receptor 4 (DR4; TRAIL-R1) and death receptor 5 (DR5; TRAIL-R2) at the cell surface through engagement of the extrinsic or intrinsic apoptotic pathways. TRAIL plays a direct role in tumor suppression during immune surveillance but this anti-tumor mechanism is lost during the disease progression. The ability of TRAIL to initiate apoptosis selectively in cancer cells has led to ongoing clinical trials with administration of recombinant TRAIL and the longer-lived TRAIL-agonist antibodies targeting either of its two pro-apoptotic death receptors.

Despite its potency, recombinant TRAIL has efficacy-limiting properties such as short serum half-life, stability, cost, and delivery. Delivery of recombinant TRAIL or TRAIL-agonist antibodies to the brain is limited by inability of recombinant TRAIL and TRAIL-agonist antibodies to cross the blood-brain barrier. Accordingly, there is a continuing need for anti-cancer compositions and methods.

BRIEF SUMMARY OF THE INVENTION

In one aspect, the present invention provides a pharmaceutical composition, comprising a compound (1):

Compound (1)

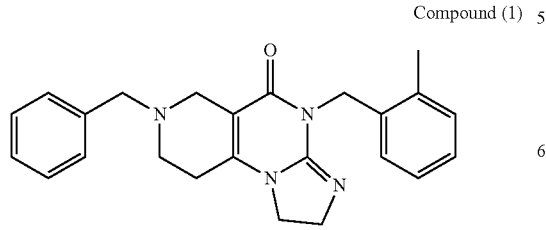

or a pharmaceutically acceptable salt thereof. In one embodiment, the pharmaceutical composition comprises compound (1) in the form of a pharmaceutically acceptable salt thereof. In one embodiment, the pharmaceutical composition comprises compound (1) in the form of a pharmaceutically acceptable mono-salt thereof. In one embodiment, the pharmaceutical composition comprises compound (1) in the form of a pharmaceutically acceptable di-salt thereof. In one embodiment, the pharmaceutical composition comprises compound (1) in the form of a pharmaceutically acceptable salt selected from the group consisting of hydrochloride, hydrobromide, hydrogensulphate, sulfates, phosphates, fumarates, succinates, oxalates and lactates, bisulfates, hydroxyl, tartrate, nitrate, citrate, bitartrate, carbonate, malate, maleate, fumarate sulfonate, methylsulfonate, formate, acetate, and carboxylate. In one embodiment, the pharmaceutical composition comprises compound (1) in the form of a pharmaceutically acceptable salt selected from the group consisting of p-toluene-sulfonate, benzenesulfonate, methanesulfonate, oxalate, succinate, tartrate, citrate, fumarate, glucuronate, ascorbate and maleate. In one embodiment, the pharmaceutical composition comprises compound (1) in the form of a pharmaceutically acceptable salt selected from the group consisting of ammonium, sodium, potassium, calcium, magnesium, zinc, lithium, and/or with other counter-ions such as methylamino, dimethylamino, diethylamino and triethylamino counter-ions. In one embodiment, the pharmaceutical composition comprises compound (1) in the form of a hydrochloride di-salt or hydrobromide di-salt.

In one embodiment, the pharmaceutical composition of the present invention includes a pharmaceutically acceptable carrier.

In some embodiments, a pharmaceutical composition in accordance with the present invention includes a second therapeutic agent. In one such embodiment, the second therapeutic agent is an anti-cancer agent. In one embodiment, the anti-cancer agent is a mitotic inhibitor. In one embodiment, the anti-cancer agent is selected from the group consisting of: paclitaxel, docetaxel and a combination thereof. In an alternative embodiment, the second therapeutic agent is an anti-angiogenic agent. In one embodiment, the anti-angiogenic agent is bevacizumab. In one embodiment, the second therapeutic agent is administered as part of combination therapy to treat a patient. In one embodiment, details for the combination therapy is included in the package insert for compound (1).

In some embodiments, the pharmaceutical composition is formulated for oral administration.

In another aspect, the present invention provides a method of treatment. In one embodiment, the method of treatment comprises administering to a subject a pharmaceutical composition, the pharmaceutical composition comprising a pharmaceutically effective amount of compound (1):

Compound (1)

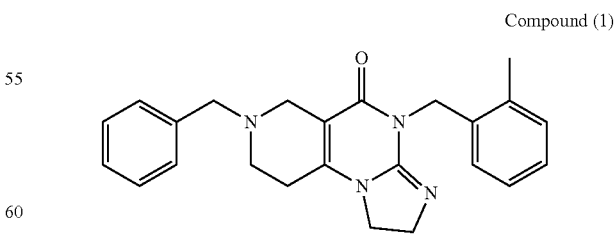

or a pharmaceutically acceptable salt thereof.

In one embodiment, the method of treatment comprises administering to the subject a pharmaceutical composition comprising a pharmaceutically effective amount of compound (1) or a pharmaceutically acceptable salt thereof. In one embodiment, the method of treatment comprises administering to the subject a pharmaceutical composition comprising a pharmaceutically effective amount of compound (1) or a pharmaceutically acceptable salt thereof and a pharmaceutically acceptable carrier.

In some embodiments, the method of treatment comprises further comprising administering an additional therapeutic agent. In one embodiment, the additional therapeutic agent includes an anti-cancer agent. In one embodiment, the additional anti-cancer agent comprises an anti-mitotic agent. In one embodiment, the additional anti-cancer agent comprises paclitaxel, docetaxel, bevacizumab or any combinations thereof.

In one embodiment, the method of treatment further comprises assaying tumor necrosis factor (TNF)-related apoptosis-inducing ligand in a sample obtained from the subject undergoing treatment. In one embodiment, the TNF-related apoptosis-inducing ligand is assayed in a blood sample obtained from the subject.

In one embodiment of the method of treatment in accordance with the present invention, the subject undergoing treatment has, or is at risk of having, cancer. In one embodiment, the cancer is selected from the group consisting of colon cancer, breast cancer, glioblastoma multiforme, Mantle cell lymphoma, and colorectal cancer.

In one embodiment of the method of treatment in accordance with the present invention, the subject is at risk of having cancer. In one embodiment, the cancer is selected from the group consisting of actinic keratosis, Barrett's esophagus, atrophic gastritis, dyskeratosis congenital, sideropenic dysphagia, lichen planus, oral submucous fibrosis, solar elastosis, cervical dysplasia, leukoplakia, and erythroplakia.

In one embodiment of the method of treatment in accordance with the present invention, the pharmaceutical composition is administered via an oral route of administration. In one embodiment, the pharmaceutical composition is administered via a route of administration selected from the group consisting of: rectal, nasal, pulmonary, epidural, ocular, otic, intra-arterial, intracardiac, intracerebroventricular, intradermal, intravenous, intramuscular, intraperitoneal, intraosseous, intrathecal, intravesical, subcutaneous, topical, transdermal, transmucosal, sublingual, buccal, vaginal, and inhalational routes of administration.

In one embodiment, the present invention provides a method of treating a subject having, or is at risk of having, brain cancer, the method comprising: administering to the subject a pharmaceutical composition comprising a pharmaceutically effective amount of compound (1):

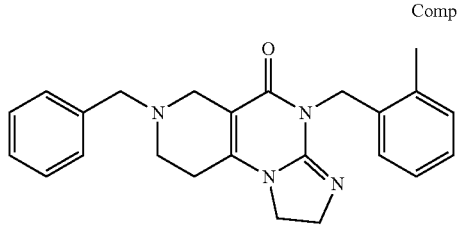

Compound (1)

or a pharmaceutically acceptable salt thereof. In one embodiment, the method of treating a subject having, or is at risk of having brain cancer, comprises administering to the subject a pharmaceutical composition comprising a pharmaceutically effective amount of compound (1) or a pharmaceutically acceptable salt thereof and a pharmaceutically acceptable carrier.

In one embodiment, the present invention provides a method of treatment comprising administering to a subject a pharmaceutical composition, the pharmaceutical composition comprising a pharmaceutically effective amount of compound (1):

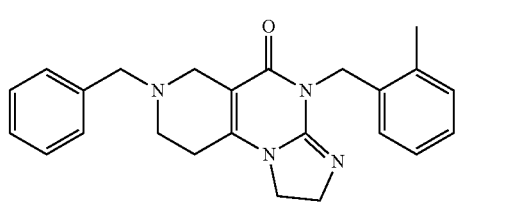

Compound (1)

or a pharmaceutically acceptable salt thereof; and a pharmaceutically acceptable carrier.

The foregoing summary, as well as the following detailed description of embodiments of the compositions and methods of treatment, will be better understood when read in conjunction with the appended claims. It should be understood, however, that the invention is not limited to the precise arrangements and instrumentalities described herein.

In another aspect, the present invention provides a method of treatment, which comprises administering to a subject in need of such treatment a combination of a first therapeutic agent including the following compound (1) and a second therapeutic agent, the method comprising:

(i) administering to the subject the first therapeutic agent including compound (1):

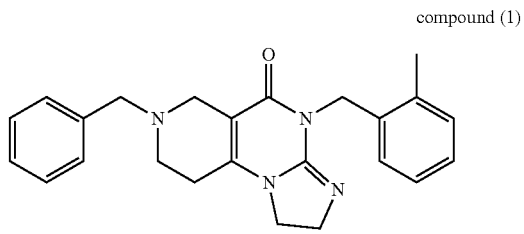 [SMILES: Cc1ccccc1CN1C(=O)C2=C(CCN(Cc3ccccc3)C2)N2CCN=C12]

compound (1)

or a pharmaceutically acceptable salt thereof;

(ii) waiting until a predetermined waiting time has elapsed after the time of administration of the first therapeutic agent to the subject; and (iii) administering the second therapeutic agent to the subject, wherein the predetermined waiting time is chosen so as to obtain a delayed therapeutic effect of the first therapeutic agent without an increased risk or with a reduced risk of possible combined toxic effects of the first and second therapeutic agents.

In another aspect, the present invention provides a method of treatment, which comprises administering to a subject in need of such treatment a combination of a first therapeutic agent and a second therapeutic agent, the method comprising:

(i) administering to the subject the first therapeutic agent including compound (1):

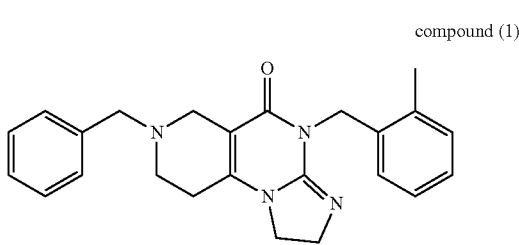

compound (1)

or a pharmaceutically acceptable salt thereof;
(ii) monitoring level of compound (1) or a pharmaceutically acceptable salt thereof or a metabolite thereof in the subject using pharmacokinetic profiling; and
(iii) administering the second therapeutic agent conditional on the level of the first therapeutic agent in the subject.

In another aspect, the present invention provides a method of treatment, which comprises administering to a subject in need of such treatment a combination of a first therapeutic agent and a second therapeutic agent, the method comprising:
(i) administering to the subject the first therapeutic agent including compound (1):

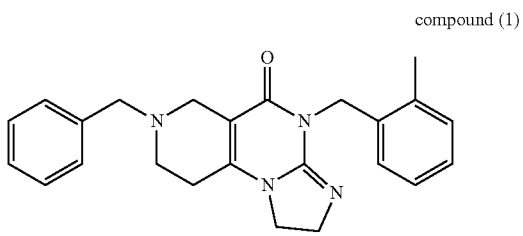 [SMILES: Cc1ccccc1CN1C(=O)C2=C(CCN(Cc3ccccc3)C2)N2CCN=C12]

compound (1)

or a pharmaceutically acceptable salt thereof; and
(iii) administering the second therapeutic agent conditional on the expected half life of exemplary compound (1) of about 3 hours to about 8 hours in the subject undergoing treatment. In some embodiments, the expected half life of exemplary compound (1) is from about 3 hours to about 24 hours in the subject undergoing treatment.

In another aspect, the present invention provides a method of treatment, which comprises administering to a subject in need of such treatment a combination of a first therapeutic agent and a second therapeutic agent, the method comprising:
(i) administering to the subject the first therapeutic agent including compound (1):

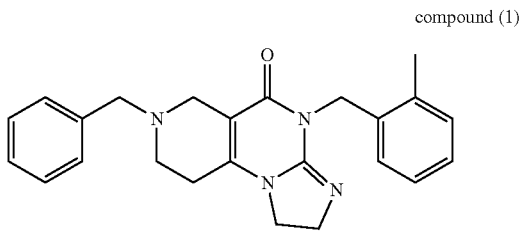 [SMILES: Cc1ccccc1CN1C(=O)C2=C(CCN(Cc3ccccc3)C2)N2CCN=C12]

compound (1)

or a pharmaceutically acceptable salt thereof; and
(iii) administering the second therapeutic agent conditional on adverse events from the first therapeutic agent have resolved or are resolving. In some embodiments, adverse events from the first therapeutic agent are related to the blood levels of the first therapeutic agent or metabolites thereof in the subject undergoing treatment.

In another aspect, the present invention provides a kit for monitoring of compound (1) or a pharmaceutically acceptable salt thereof or a metabolite thereof in an individual treated with compound (1) or a pharmaceutically acceptable salt thereof or a metabolite thereof using pharmacokinetic profiling, the kit comprising a plurality of point-of-care device or a point of use device capable of quantitating the drug in the at least two samples or matrices suitable for storage of the at least two samples prior to quantitation by a laboratory. In some embodiments, a kit according to the present invention further comprising instructions for collecting and/or storing the at least two samples.

BRIEF DESCRIPTION OF THE DRAWINGS

The foregoing summary, as well as the following detailed description of embodiments of the present invention, will be better understood when read in conjunction with the appended drawings of an exemplary embodiment. It should be understood, however, that the invention is not limited to the precise arrangements and instrumentalities shown.

In the drawings.

DETAILED DESCRIPTION OF THE INVENTION

Figure 1:
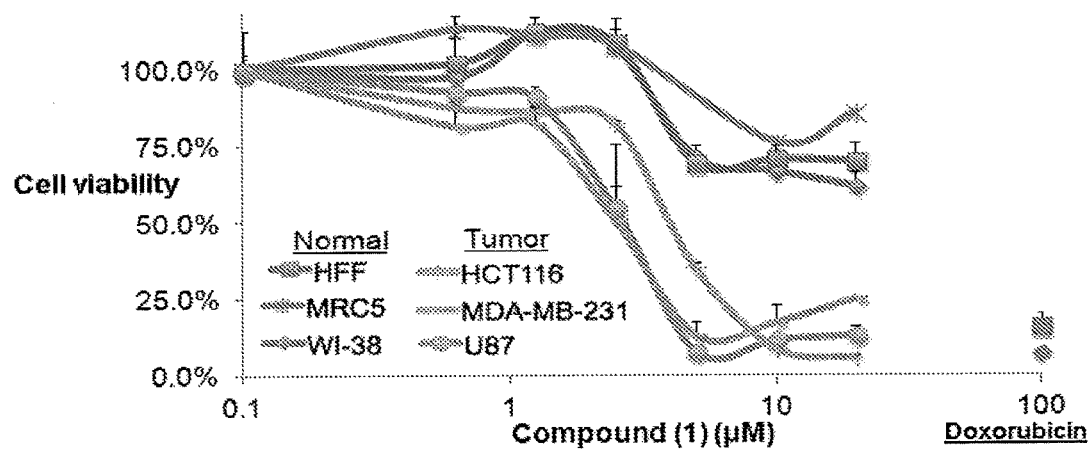
FIG. 1 illustrates a dose response relation showing effects of various concentrations of an exemplary compound of the present invention, compound (1), on viability of tumor and normal cells.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Engelke, D. R., RNA Interference (RNAi): Nuts and Bolts of RNAi Technology, DNA Press LLC, Eagleville, Pa., 2003; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 9780470151808, as well as U.S. Patent Application Publication No. 20120276088. The content of each of the foregoing references is hereby incorporated by reference in its entirety.

The singular terms "a," "an," and "the" are not intended to be limiting and include plural referents unless explicitly state or the context clearly indicates otherwise.

I. Compositions

In one aspect, the present invention provides a pharmaceutical composition, comprising a compound (1):

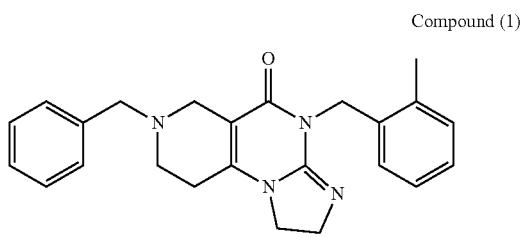 [SMILES: Cc1ccccc1CN1C(=O)C2=C(CCN(Cc3ccccc3)C2)N2CCN=C12]

Compound (1)

or a pharmaceutically acceptable salt thereof. In one embodiment, the pharmaceutical composition comprises compound (1) or a pharmaceutically acceptable mono-salt thereof. In one embodiment, the pharmaceutical composition comprises compound (1) or a pharmaceutically acceptable di-salt thereof. In one embodiment, the pharmaceutical composition comprises compound (1) or a pharmaceutically acceptable mono- or multi-salt (e.g., di-salt or tri-salt, where it is understood that throughout this disclosure a di-salt encompasses a multi-salt or tri-salt) thereof selected from the group consisting of hydrochloride, hydrobromide, hydrogensulphate, sulfates, phosphates, fumarates, succinates, oxalates and lactates, bisulfates, hydroxyl, tartrate, nitrate, citrate, bitartrate, carbonate, malate, maleate, fumarate sulfonate, methylsulfonate, formate, and carboxylate. In one embodiment, the pharmaceutical composition comprises compound (1) or a pharmaceutically acceptable salt thereof selected from the group consisting of p-toluenesulfonate, benzenesulfonate, methanesulfonate, oxalate, succinate, tartrate, citrate, fumarate and maleate. In one embodiment, the pharmaceutical composition comprises compound (1) or a pharmaceutically acceptable salt selected from the group consisting of ammonium, sodium, potassium, calcium, magnesium, zinc, lithium, and/or with counter-ions such as methylamino, dimethylamino, diethylamino and triethylamino counter-ions. In one embodiment, the pharmaceutical composition comprises compound (1), a hydrochloride di-salt thereof (e.g., di-hydrochloride salt) or a hydrobromide di-salt thereof (e.g., di-hydrobromide salt).

Compound (1) has the same chemical structure that would be revealed by structural analysis (e.g. NMR, X-ray diffraction) of compound NSC 350625, available from the National Cancer Institute's Developmental Therapeutics Program Repository.

In one embodiment, a pharmaceutical composition in accordance with the present invention includes a di-salt (e.g., a di-hydrochloride salt) of compound (1).

Salts (e.g., di-salts or tri-salts) of compound (1) can be prepared from compound (1):

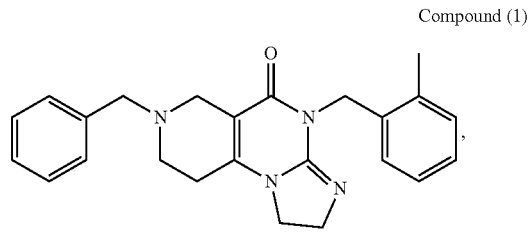 [SMILES: Cc1ccccc1CN1C(=O)C2=C(CCN(Cc3ccccc3)C2)N2CCN=C12]

Compound (1)

which can be obtained commercially or synthesized using standard chemical synthetic methodology known to one of ordinary skill in the art.

In one embodiment, the pharmaceutical composition in accordance with the present invention includes at least one pharmaceutically acceptable carrier. Suitable pharmaceutically acceptable carriers, included, but are not limited to, those found in Handbook of Pharmaceutical Excipients, 7th Edition, edited by Raymond C. Rowe et al., American Pharmaceutical Association, Washington, USA and Pharmaceutical Press, London; and earlier editions.

Exemplary pharmaceutically acceptable carriers, methods for making pharmaceutical compositions and various dosage forms, as well as modes of administration are well-known in the art, for example as detailed in Pharmaceutical Dosage Forms: Tablets, edited by Larry L. Augsburger and Stephen W. Hoag, London: Informa Healthcare, 2008; and in L. V. Allen, Jr. et al., Ansel's Pharmaceutical Dosage Forms and Drug Delivery Systems, 8th Ed., Philadelphia, Pa.: Lippincott, Williams & Wilkins, 2004; A. R. Gennaro, Remington: The Science and Practice of Pharmacy, Lippincott Williams & Wilkins, 21st ed., 2005, particularly chapter 89; and J. G. Hardman et al., Goodman & Gilman's The Pharmacological Basis of Therapeutics, McGraw-Hill Professional, 10th ed., 2001.

In some embodiments, the pharmaceutical composition of the present invention is formulated for ocular administration. In some embodiments, pharmaceutical compositions of the present invention are formulated for topical ocular administration. In some embodiments, the pharmaceutical compositions are formulated as ointments, drops, or liquids. In some embodiments, the pharmaceutical composition of the present invention can include conventional pharmaceutical carriers such as aqueous, powdery or oily bases, thickeners or the like.

In some embodiments, the pharmaceutical composition of the present invention is formulated as intravenous formulation. In one embodiment, the intravenous formulation comprises compound (1) or a pharmaceutically acceptable salt of compound (1) dissolved in a solvent. In one embodiment, the solvent comprises water. In one such embodiment, the intravenous formulation comprises compound (1) or a pharmaceutically acceptable salt of compound (1) dissolved in water at a concentration of 25 mg/ml. In some embodiments, the intravenous formulation includes a higher or a lower concentration of compound (1) or a pharmaceutically acceptable salt thereof. In one embodiment, the intravenous formulation includes compound (1) or a pharmaceutically acceptable salt thereof in a concentration of from about 5 mg/ml to about 100 mg/ml. In one embodiment, the intravenous formulation includes compound (1) or a pharmaceutically acceptable salt thereof in a concentration of about 50 mg/ml. In one embodiment, the intravenous formulation includes compound (1) or a pharmaceutically acceptable salt thereof in a concentration of about 5 mg/ml. In one embodiment, the intravenous formulation includes from about 0.5% to about 10% of compound (1) or a pharmaceutically acceptable salt thereof. In one embodiment, the intravenous formulation includes from about 5% of compound (1) or a pharmaceutically acceptable salt thereof.

In some embodiments, the intravenous formulation has pH of about 3. In one embodiment, pH of the intravenous formulation is adjusted to pH 3 with a phosphate buffer. In some embodiments, the intravenous formulation includes dextrose or sodium chloride. In one embodiment, the intravenous formulation including compound (1) or a pharmaceutically acceptable salt thereof in a concentration of about 5 mg/ml and pH 3 forms a stable solution. In one embodiment, the intravenous formulation includes compound (1) or a pharmaceutically acceptable salt thereof in a concentration of about 5 mg/ml and pH<5 and forms a stable solution. In one embodiment, the intravenous formulation includes compound (1) or a pharmaceutically acceptable salt thereof and one or more antioxidants. In one embodiment, the intravenous formulation includes a mixture of mono- and di-hydrochloride salt of compound (1). In one embodiment, the intravenous formulation includes compound (1) or a pharmaceutically acceptable salt thereof as a 1% solution having compound (1) or for a pharmaceutically acceptable salt thereof in a concentration of about 10 mg/ml. In one such embodiment, the intravenous formulation is a solution having a pH of about 3.3. In one embodiment, the pH is less than 4.0.

In one embodiment, a pharmaceutical composition according to the invention comprises about 0.1-99% of a salt of compound (1) or a pharmaceutically acceptable salt thereof. In one such embodiment, the pharmaceutical composition further includes a pharmaceutically acceptable carrier. In one embodiment, a suitable pharmaceutically acceptable carrier includes an oil. In one embodiment, a suitable pharmaceutically acceptable carrier includes a sterile water. In one embodiment, a suitable pharmaceutically acceptable carrier includes an aqueous carrier.

In some embodiments, the intravenous formulation includes dextrose and/or sodium.

In one embodiment, the intravenous formulation comprises compound (1) or a di-hydrochloride salt of compound (1) dissolved in water at 25 mg/ml. In one such embodiment, the intravenous formulation is adjusted to pH 3 with phosphate buffer. In one such embodiment, the intravenous formulation includes dextrose or sodium chloride. In one such embodiment, the intravenous formulation includes a higher or a lower increase or decrease the concentration of the di-hydrochloride salt of compound (1). In one embodiment, the intravenous formulation includes compound (1) or a di-hydrochloride salt of compound (1) in a concentration of about 5 mg/ml. In one embodiment, the intravenous formulation including compound (1) or a di-hydrochloride salt of compound (1) in a concentration of about 5 mg/ml and pH 3 forms a stable solution. In one embodiment, the intravenous formulation includes compound (1) or a di-hydrochloride salt of compound (1) in a concentration of about 5 mg/ml and pH<5 and forms a stable solution. In one embodiment, the intravenous formulation includes compound (1) or a di-hydrochloride salt of compound (1) and one or more antioxidants. In one embodiment, the intravenous formulation includes a mixture of mono- and di-hydrochloride salt of compound (1). In one embodiment, the intravenous formulation includes compound (1) or a di-hydrochloride salt of compound (1) as a 1% solution having compound (1) or the di-hydrochloride salt of compound (1) in a concentration of about 10 mg/ml. In one such embodiment, the intravenous formulation is a solution having a pH of about 3.33. In one embodiment, the pH is less than 4.0.

In one embodiment, the intravenous formulation includes from about 0.5% to about 10% (or from about 5 mg/ml to about 100 mg/ml) of compound (1) or a di-salt of compound (1). In one embodiment, the intravenous formulation includes from about 5% (or about 50 mg/ml) of compound (1) or a di-salt of compound (1). In one embodiment, the intravenous infusion rate may be slowed to decrease side effects of compound (1) or a di-salt of compound (1).

In one embodiment, a pharmaceutical composition according to the invention comprises about 0.1-99% of a salt of compound (1); and a pharmaceutically acceptable carrier, e.g., an oil or a sterile water or other aqueous carriers. In one embodiment, a pharmaceutical composition according to the invention comprises a mono or di-salt of compound (1) in a range of from about 5% to about 50% for oral dosage forms.

In some embodiments, a pharmaceutical composition of the present invention includes an antioxidant. Suitable antioxidants include: ascorbic acid derivatives such as ascorbic acid, erythorbic acid, sodium ascorbate, thiol derivatives such as thioglycerol, cysteine, acetylcysteine, cystine, dithioerythreitol, dithiothreitol, glutathione, tocopherols, butylated hydroxyanisole (BHA), butylated hydroxytoluene (BHT), sulfurous acid salts such as sodium sulfate, sodium bisulfite, acetone sodium bisulfite, sodium metabisulfite, sodium sulfite, sodium formaldehyde sulfoxylate, and sodium thiosulfate, nordihydroguaiaretic acid. It should be noted that antioxidants used for aqueous formulations typically include: sodium sulphite, sodium metabisulphite, sodium formaldehyde sulphoxylate and ascorbic acid and combinations thereof, whereas antioxidants used in oil-based solutions, organic solvents, include butylated hydroxytoluene (BHT), butylated hydroxyanisole (BHA) and propyl gallate and combinations thereof. In yet other embodiments, an antioxidant can be one or more of a flavanoid, an isoflavone, monothioglycerol, L-cysteine, thioglycolic acid, α-tocopherol, ascorbic acid 6-palmitate, dihydrolipoic acid, butylated hydroxytoluene (BHT), butylated hydroxyanisole (BHA), vitamin E, propyl gallate, β-carotene, ascorbic acid. Antioxidants can typically be used in about 0.1% to 1.0% by weight, more typically about 0.2%.

In one embodiment, the pharmaceutical composition includes compound (1) or a pharmaceutically acceptable salt thereof and at least one other therapeutic agent. In one such embodiment, the at least one other therapeutic agent is selected from the group consisting of hormone analogues and antihormones, aromatase inhibitors, LHRH agonists and antagonists, inhibitors of growth factors, growth factor antibodies, growth factor receptor antibodies, tyrosine kinase inhibitors; antimetabolites; antitumour antibiotics; platinum derivatives; alkylation agents; antimitotic agents; tubuline inhibitors; PARP inhibitors, topoisomerase inhibitors, serine/threonine kinase inhibitors, tyrosine kinase inhibitors, protein protein interaction inhibitors, RAF inhibitors, MEK inhibitors, ERK inhibitors, IGF-1R inhibitors, ErbB receptor inhibitors, rapamycin analogs, BTK inhibitors, CRM1 inhibitors (e.g., KPT185), P53 modulators (e.g., Nutlins), antiangiogenics (e.g., axitinib, aflibercept, sorafenib, and regorafenib), amifostin, anagrelid, clodronat, filgrastin, interferon, interferon alpha, leucovorin, rituximab, procarbazine, levamisole, mesna, mitotane, pamidronate and porfimer, 2-chlorodesoxyadenosine, 2-fluorodesoxy-cytidine, 2-methoxyoestradiol, 2C4,3-alethine, 131-1-TM-601, 3CPA, 7-ethyl-10-hydroxycamptothecin, 16-aza-epothilone B, A 105972, A 204197, abiraterone, aldesleukin, alitretinoin, allovectin-7, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, AMG-479 (ganitumab), ARRY 162, ARRY 438162, ARRY-300, ARRY-142886/AZD-6244 (selumetinib), ARRY-704/AZD-8330, AR-12, AR-42, AS-703988, AXL-1717, AZD-8055, AZD-5363, AZD-6244, ARQ-736, ARQ 680, AS-703026 (primasertib), avastin, AZD-2014, azacytidine, azaepothilone B, azonafide, BAY-43-9006, BAY 80-6946, BBR-3464, BBR-3576, bevacizumab, BEZ-235, biricodar dicitrate, BCX-1777, BKM-120, bleocin, BLP-25, BMS-184476, BMS-247550, BMS-188797, BMS-275291, BMS-663513, BMS- 754807, BNP-1350, BNP-7787, BIBW 2992 (afatinib, tomtovok), BIBF 1120 (vargatef), BI 836845, BI 2536, BI 6727, BI 836845, BI 847325, BI 853520, BUB-022, bleomycinic acid, bleomycin A, bleomycin B, brivanib, bryostatin-1, bortezomib, brostallicin, busulphan, BYL-719, CA-4 prodrug, CA-4, CapCell, calcitriol, canertinib, canfosfamide, capecitabine, carboxyphthalatoplatin, CC1-779, CC-115, CC-223, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, CKI-27, clofarabin, colchicin, combretastatin A4, COT inhibitors, CHS-828, CH-5132799, CLL-Thera, CMT-3 cryptophycin 52, CTP-37, CTLA-4 monoclonal antibodies, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, DS-7423, E7010, E-6201, edatrexat, edotreotide, efaproxiral, eflornithine, EGFR inhibitors, EKB-569, EKB-509, enzastaurin, enzalutamide, elsamitrucin, epothilone B, epratuzumab, ER-86526, erlotinib, ET-18-0CH3, ethynylcytidine, ethynyloestradiol, exatecan, exatecan mesylate, exemestane, exisulind, fenretinide, figitumumab, floxuridine, folic acid, FOLFOX, FOLFOX4, FOLFIRI, formestane, fotemustine, galarubicin, gallium maltolate, gefinitib, gemtuzumab, gimatecan, glufosfamide, GCS-100, GDC-0623, GDC-0941 (pictrelisib), GDC-0980, GDC-0032, GDC-0068, GDC-0349, GDC-0879, G17DT immunogen, GMK, GPX-100, gp100-peptide vaccines, GSK-5126766, GSK-690693, GSK-1120212 (trametinib), GSK-2118436 (dabrafenib), GSK-2126458, GSK-2132231A, GSK-2334470, GSK-2110183, GSK-2141795, GW2016, granisetron, herceptine, hexamethylmelamine, histamine, homoharringtonine, hyaluronic acid, hydroxyurea, hydroxyprogesterone caproate, ibandronate, ibrutinib, ibritumomab, idatrexate, idenestrol, IDN-5109, IGF-1R inhibitors, IMC-1C11, IMC-A12 (cixutumumab), immunol, indisulam, interferon alpha-2a, interferon alpha-2b, pegylated interferon alpha-2b, interleukin-2, INK-1117, INK-128, INSM-18, ionafarnib, ipilimumab, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, KW-2450, lobaplatin, leflunomide, lenograstim, leuprolide, leuporelin, lexidronam, LGD-1550, linezolid, lutetium texaphyrin, lometrexol, losoxantrone, LU 223651, lurtotecan, LY-S6AKT1, LY-2780301, mafosfamide, marimastat, mechloroethamine, MEK inhibitors, MEK-162, methyltestosteron, methylprednisolone, MEDI-573, MEN-10755, MDX-H210, MDX-447, MDX-1379, MGV, midostaurin, minodronic acid, mitomycin, mivobulin, MK-2206, MK-0646 (dalotuzumab), MLN518, motexaf in gadolinium, MS-209, MS-275, MX6, neridronate, neratinib, Nexavar, neovastat, nilotinib, nimesulide, nitroglycerin, nolatrexed, norelin, N-acetylcysteine, 06-benzylguanine, oblimersen, omeprazole, oncophage, oncoVEXGM-CSF, ormiplatin, ortataxel, OX44 antibodies, OSI-027, OSI-906 (linsitinib), 4-1BB antibodies, oxantrazole, oestrogen, panitumumab, patupilone, pegfilgrastim, PCK-3145, pegfilgrastim, PBI-1402, PBI-05204, PD0325901, PD-1 antibodies, PEG-paclitaxel, albumin-stabilized paclitaxel, PEP-005, PF-05197281, PF-05212384, PF-04691502, PHT-427, P-04, PKC412, P54, PI-88, pelitinib, pemetrexed, pentrix, perifosine, perillylalcohol, pertuzumab, PI3K inhibitors, PI3K/mTOR inhibitors, PG-TXL, PG2, PLX-4032/RO-5185426 (vemurafenib), PLX-3603/RO-5212054, PT-100, PWT-33597, PX-866, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, R115777, RAF-265, ramosetron, ranpirnase, RDEA-119/BAY 869766, RDEA-436, rebeccamycin analogues, receptor tyrosine kinase (RTK) inhibitors, regorafenib, revimid, RG-7167, RG-7304, RG-7421, RG-7321, RG 7440, rhizoxin, rhu-MAb, rinfabate, risedronate, rituximab, robatumumab, rofecoxib, RO-31-7453, RO-5126766, RO-5068760, RPR 109881A, rubidazone, rubitecan, R-flurbiprofen, RX-0201, S-9788, sabarubicin, SAHA, sargramostim, satraplatin, SB 408075, Se-015/Ve-015, SU5416, SU6668, SDX-101, semustin, seocalcitol, SM-11355, SN-38, SN-4071, SR-27897, SR-31747, SR-13668, SRL-172, sorafenib, spiroplatin, squalamine, suberanilohydroxamic acid, sutent, T 900607, T 138067, TAK-733, TAS-103, tacedinaline, talaporf in, Tarceva, tariquitar, tasisulam, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymalfasin, thymectacin, tiazofurin, tipifarnib, tirapazamine, tocladesine, tomudex, toremofin, trabectedin, TransMID-107, transretinic acid, traszutumab, tremelimumab, tretinoin, triacetyluridine, triapine, triciribine, trimetrexate, TLK-286TXD 258, tykerb/tyverb, urocidin, valrubicin, vatalanib, vincristine, vinflunine, virulizin, WX-UK1, WX-554, vectibix, xeloda, XELOX, XL-147, XL-228, XL-281, XL-518/R-7420/GDC-0973, XL-765, YM-511, YM-598, ZD-4190, ZD-6474, ZD-4054, ZD-0473, ZD-6126, ZD-9331, ZD1839, ZSTK-474, zoledronat, zosuquidar, and combinations thereof.

In one embodiment, the at least one other therapeutic agent comprises one or more hormone analogues and/or antihormones are selected from the group consisting of tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxy-progesterone, octreotide, and combinations thereof. In one embodiment, the at least one other therapeutic agent comprises one or more LHRH agonists and/or antagonists selected from the group consisting of goserelin acetate, luprolide acetate, triptorelin pamoate and combinations thereof and wherein the LHRH antagonists are selected from the group consisting of Degarelix, Cetrorelix, Abarelix, Ozarelix, Degarelix combinations thereof. In one embodiment, the at least one other therapeutic agent comprises one or more growth factor inhibitors selected from the group consisting of inhibitors of: platelet derived growth factor (PDGF), fibroblast growth factor (FGF), vascular endothelial growth factor (VEGF), epidermal growth factor (EGF), insuline-like growth factors (IGF), human epidermal growth factor (HER) and hepatocyte growth factor (HGF). In one embodiment, the at least one other therapeutic agent comprises one or more inhibitors of the human epidermal growth factor selected from the group consisting of HER2, HER3, and HER4. In one embodiment, the at least one other therapeutic agent comprises one or more tyrosine kinase inhibitors selected from the group consisting of cetuximab, gefitinib, imatinib, lapatinib and trastuzumab, and combinations thereof. In one embodiment, the at least one other therapeutic agent comprises one or more aromatase inhibitors selected from the group consisting of anastrozole, letrozole, liarozole, vorozole, exemestane, atamestane, and combinations thereof. In one embodiment, the at least one other therapeutic agent comprises one or more antimetabolites which are antifolates selected from the group consisting of methotrexate, raltitrexed, and pyrimidine analogues. In one embodiment, the at least one other therapeutic agent comprises one or more antimetabolites which are pyrimidine analogues selected from the group consisting of 5-fluorouracil, capecitabin and gemcitabin. In one embodiment, the at least one other therapeutic agent comprises one or more antimetabolites which are purine and/or adenosine analogues selected from the group consisting of mercaptopurine, thioguanine, cladribine and pentostatin, cytarabine, fludarabine, and combinations thereof. In one embodiment, the at least one other therapeutic agent comprises one or more antitumour antibiotics selected from the group consisting of anthracyclins, doxorubicin, daunorubicin, epirubicin and idarubicin, mitomycin-C, bleomycin, dactinomycin, plicamycin, streptozocin and combinations thereof. In one embodiment, the at least one other therapeutic agent comprises one or more platinum derivatives selected from the group consisting of cisplatin, oxaliplatin, carboplatin and combinations thereof. In one embodiment, the at least one other therapeutic agent comprises one or more alkylation agents selected from the group consisting of estramustin, meclorethamine, melphalan, chlorambucil, busulphan, dacarbazin, cyclophosphamide, ifosfamide, temozolomide, nitrosoureas, and combinations thereof. In one embodiment, the at least one other therapeutic agent comprises nitrosoureas selected from the group consisting of carmustin, lomustin, thiotepa, and combinations thereof. In one embodiment, the at least one other therapeutic agent comprises antimitotic agents selected from the group consisting of *Vinca* alkaloids and taxanes. In one embodiment, the at least one other therapeutic agent comprises one or more taxanes selected from the group consisting of paclitaxel, docetaxel, and combinations thereof. In one embodiment, the at least one other therapeutic agent comprises one or more *Vinca* alkaloids selected from the group consisting of vinblastine, vindesin, vinorelbin, vincristine, and combinations thereof. In one embodiment, the at least one other therapeutic agent comprises one or more topoisomerase inhibitors which are epipodophyllotoxins. In one embodiment, the at least one other therapeutic agent comprises one or more epipodophyllotoxins selected from the group consisting of etoposide and etopophos, teniposide, amsacrin, topotecan, irinotecan, mitoxantron, and combinations thereof. In one embodiment, the at least one other therapeutic agent comprises one or more serine/threonine kinase inhibitors selected from the group consisting of PDK 1 inhibitors, B-Raf inhibitors, mTOR inhibitors, mTORC1 inhibitors, PI3K inhibitors, dual mTOR/PI3K inhibitors, STK 33 inhibitors, AKT inhibitors, PLK 1 inhibitors, inhibitors of CDKs, Aurora kinase inhibitors, and combinations thereof. In one embodiment, the at least one other therapeutic agent comprises one or more tyrosine kinase inhibitors which are PTK2/FAK inhibitors. In one embodiment, the at least one other therapeutic agent comprises one or more protein protein interaction inhibitors selected from the group consisting of IAP, Mcl-1, MDM2/MDMX and combinations thereof. In one embodiment, the at least one other therapeutic agent comprises one or more rapamycin analogs selected from the group consisting of everolimus, temsirolimus, ridaforolimus, sirolimus, and combinations thereof. In one embodiment, the at least one other therapeutic agent comprises one or more therapeutic agents selected from the group consisting of amifostin, anagrelid, clodronat, filgrastin, interferon, interferon alpha, leucovorin, rituximab, procarbazine, levamisole, mesna, mitotane, pamidronate and porfimer, and combinations thereof. In one embodiment, the at least one other therapeutic agent comprises one or more therapeutic agents selected from the group consisting of 2-chlorodesoxyadenosine, 2-fluorodesoxy-cytidine, 2-methoxyoestradiol, 2C4,3-alethine, 131-1-TM-601, 3CPA, 7-ethyl-10-hydroxycamptothecin, 16-aza-epothilone B, A 105972, A 204197, abiraterone, aldesleukin, alitretinoin, allovectin-7, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, AMG-479 (ganitumab), ARRY 162, ARRY 438162, ARRY-300, ARRY-142886/AZD-6244 (selumetinib), ARRY-704/AZD-8330, AR-12, AR-42, AS-703988, AXL-1717, AZD-8055, AZD-5363, AZD-6244, ARQ-736, ARQ 680, AS-703026 (primasertib), avastin, AZD-2014, azacytidine, azaepothilone B, azonafide, BAY-43-9006, BAY 80-6946, BBR-3464, BBR-3576, bevacizumab, BEZ-235, biricodar dicitrate, BCX-1777, BKM-120, bleocin, BLP-25, BMS-184476, BMS-247550, BMS-188797, BMS-275291, BMS-663513, BMS-754807, BNP-1350, BNP-7787, BIBW 2992 (afatinib, tomtovok), BIBF 1120 (vargatef), BI 836845, BI 2536, BI 6727, BI 836845, BI 847325, BI 853520, BUB-022, bleomycinic acid, bleomycin A, bleomycin B, brivanib, bryostatin-1, bortezomib, brostallicin, busulphan, BYL-719, CA-4 prodrug, CA-4, CapCell, calcitriol, canertinib, canfosfamide, capecitabine, carboxyphthalatoplatin, CC1-779, CC-115, CC-223, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, CKI-27, clofarabin, colchicin, combretastatin A4, COT inhibitors, CHS-828, CH-5132799, CLL-Thera, CMT-3 cryptophycin 52, CTP-37, CTLA-4 monoclonal antibodies, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, DS-7423, E7010, E-6201, edatrexat, edotreotide, efaproxiral, eflornithine, EGFR inhibitors, EKB-569, EKB-509, enzastaurin, enzalutamide, elsamitrucin, epothilone B, epratuzumab, ER-86526, erlotinib, ET-18-OCH3, ethynylcytidine, ethynyloestradiol, exatecan, exatecan mesylate, exemestane, exisulind, fenretinide, figitumumab, floxuridine, folic acid, FOLFOX, FOLFOX4, FOLFIRI, formestane, fotemustine, galarubicin, gallium maltolate, gefinitib, gemtuzumab, gimatecan, glufosfamide, GCS-100, GDC-0623, GDC-0941 (pictrelisib), GDC-0980, GDC-0032, GDC-0068, GDC-0349, GDC-0879, G17DT immunogen, GMK, GPX-100, gp100-peptide vaccines, GSK-5126766, GSK-690693, GSK-1120212 (trametinib), GSK-2118436 (dabrafenib), GSK-2126458, GSK-2132231A, GSK-2334470, GSK-2110183, GSK-2141795, GW2016, granisetron, herceptine, hexamethylmelamine, histamine, homoharringtonine, hyaluronic acid, hydroxyurea, hydroxyprogesterone caproate, ibandronate, ibrutinib, ibritumomab, idatrexate, idenestrol, IDN-5109, IGF-1R inhibitors, IMC-1C11, IMC-A12 (cixutumumab), immunol, indisulam, interferon alpha-2a, interferon alpha-2b, pegylated interferon alpha-2b, interleukin-2, INK-1117, INK-128, INSM-18, ionafarnib, ipilimumab, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, KW-2450, lobaplatin, leflunomide, lenograstim, leuprolide, leuporelin, lexidronam, LGD-1550, linezolid, lutetium texaphyrin, lometrexol, losoxantrone, LU 223651, lurtotecan, LY-S6AKT1, LY-2780301, mafosfamide, marimastat, mechloroethamine, MEK inhibitors, MEK-162, methyltestosteron, methylprednisolone, MEDI-573, MEN-10755, MDX-H210, MDX-447, MDX-1379, MGV, midostaurin, minodronic acid, mitomycin, mivobulin, MK-2206, MK-0646 (dalotuzumab), MLN518, motexaf in gadolinium, MS-209, MS-275, MX6, neridronate, neratinib, Nexavar, neovastat, nilotinib, nimesulide, nitroglycerin, nolatrexed, norelin, N-acetylcysteine, 06-benzylguanine, oblimersen, omeprazole, oncophage, oncoVEXGM-CSF, ormiplatin, ortataxel, OX44 antibodies, OSI-027, OSI-906 (linsitinib), 4-1BB antibodies, oxantrazole, oestrogen, panitumumab, patupilone, pegfilgrastim, PCK-3145, pegfilgrastim, PBI-1402, PBI-05204, PD0325901, PD-1 antibodies, PEG-paclitaxel, albumin-stabilized paclitaxel, PEP-005, PF-05197281, PF-05212384, PF-04691502, PHT-427, P-04, PKC412, P54, PI-88, pelitinib, pemetrexed, pentrix, perifosine, perillylalcohol, pertuzumab, PI3K inhibitors, PI3K/mTOR inhibitors, PG-TXL, PG2, PLX-4032/RO-5185426 (vemurafenib), PLX-3603/RO-5212054, PT-100, PWT-33597, PX-866, picoplatin, pivaloyloxymethylbutyrate, pixantrone, phenoxodiol O, PKI166, plevitrexed, plicamycin, polyprenic acid, porfiromycin, prednisone, prednisolone, quinamed, quinuprisin, R115777, RAF-265, ramosetron, ranpirnase, RDEA-119/BAY 869766, RDEA-436, rebeccamycin analogues, receptor tyrosine kinase (RTK) inhibitors, revimid, RG-7167, RG-7304, RG-7421, RG-7321, RG 7440, rhizoxin, rhu-MAb, rinfabate, risedronate, rituximab, robatumumab, rofecoxib, RO-31-7453, RO-5126766, RO-5068760, RPR 109881A, rubidazone, rubitecan, R-flurbiprofen, RX-0201, S-9788, sabarubicin, SAHA, sargramostim, satraplatin, SB 408075, Se-015/Ve-015, SU5416, SU6668, SDX-101, semustin, seocalcitol, SM-11355, SN-38, SN-4071, SR-27897, SR-31747, SR-13668, SRL-172, sorafenib, spiroplatin, squalamine, suberanilohydroxamic acid, sutent, T 900607, T 138067, TAK-733, TAS-103, tacedinaline, talaporf in, Tarceva, tariquitar, tasisulam, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymalfasin, thymectacin, tiazofurin, tipifarnib, tirapazamine, tocladesine, tomudex, toremofin, trabectedin, TransMID-107, transretinic acid, traszutumab, tremelimumab, tretinoin, triacetyluridine, triapine, triciribine, trimetrexate, TLK-286TXD 258, tykerb/tyverb, urocidin, valrubicin, vatalanib, vincristine, vinflunine, virulizin, WX-UK1, WX-554, vectibix, xeloda, XELOX, XL-147, XL-228, XL-281, XL-518/R-7420/GDC-0973, XL-765, YM-511, YM-598, ZD-4190, ZD-6474, ZD-4054, ZD-0473, ZD-6126, ZD-9331, ZD1839, ZSTK-474, zoledronat, zosuquidar, and combinations thereof.

In some embodiments, the at least one other therapeutic agent comprises a steroid. Steroids include, but are not limited to, dexamethasone, prednisolone, methyl prednisolone, prednisone, hydrocortisone, triamcinolone, betamethasone, and cortivazol. In some embodiments, the at least one other therapeutic agent comprises an anti-emetic. Anti-emetics include, but are not limited to, 5-HT3 receptor agonists (such as dolasetron, granisetron, ondansetron, tropisetron, palonosetron, and mirtazapine), dopamine agonists (such as domperidone, olanzapine, droperidol, haloperidol, chlorpromazine, prochlorperazine, alizapride, prochlorperazine, and metoclopramide), NK1 receptor antagonists (such as aprepitant and casopitant), antihistamines (such as cyclizine, diphenhydramine, dimenhydrinate, doxylamine, meclizine, promethazine, hydroxyzine), cannabinoids (such as *cannabis*, dronabinol, nabilone, and sativex), benzodiazepines (such as midazolam and lorazepam), anticholinergics (such as hyoscine), trimethobenzamide, ginger, emetrol, propofol, peppermint, muscimol, and ajwain.

In some embodiments, the at least one other therapeutic agent comprises anti-cancer agent which includes a mitotic inhibitor. In one embodiment, the mitotic inhibitor includes a taxane. In one embodiment, the mitotic inhibitor includes a taxane selected from the group consisting of paclitaxel and docetaxel.

In one embodiment, the pharmaceutical composition includes compound (1) or a pharmaceutically acceptable salt thereof and at least one anti-cancer agent, wherein the anti-cancer agent includes, without limitation, one or more of acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bevacizumab, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflomithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, zorubicin and combinations thereof.

Examples of suitable anti-cancer agents include, but are not limited to, those described Goodman and Gilman's The Pharmacological Basis of Therapeutics, 12th Ed., edited by Laurence Brunton, Bruce Chabner, Bjorn Knollman, McGraw Hill Professional, 2010.

In some exemplary embodiments, the pharmaceutical composition includes a salt (e.g., a mono- or di-salt) of compound (1) and at least one other therapeutic agent, wherein the at least one other therapeutic agent comprises an anti-angiogenic agent. In one such embodiment, the anti-angiogenic agent is bevacizumab. In one embodiment, the anti-angiogenic agent is selected from the group consisting of aflibercept, axitinib, angiostatin, endostatin, 16 kDa prolactin fragment, laminin peptides, fibronectin peptides, tissue metalloproteinase inhibitors (TIMP 1, 2, 3, 4), plasminogen activator, inhibitors (PAI-1, -2), tumor necrosis factor α, (high dose, invitro), TGF-β1, interferons (IFN-α, -β, γ), ELR-CXC Chemokines: IL-12; SDF-1; MIG; platelet factor 4 (PF-4); IP-10, thrombospondin (TSP), SPARC, 2-methoxyoestradiol, proliferin-related protein, suramin, sorafenib, regorafenib, thalidomide, cortisone, linomide, fumagillin (AGM-1470; TNP-470), tamoxifen, retinoids, CM101, dexamethasone, leukemia inhibitory factor (LIF), hedgehog inhibitor and combinations thereof.

The pharmaceutical combination in accordance with the present invention can include the first and second therapeutic agents in any desired proportions provided that the synergistic or cooperative effect still occurs. The synergistic pharmaceutical combination in accordance with the present invention preferably contains the first and second therapeutic agents in a ratio of from about 1:9 to about 9:1. In one embodiment, the synergistic pharmaceutical combination contains the first and second therapeutic agents in a ratio of from about 1:8 to about 8:1. In one embodiment, the synergistic pharmaceutical combination contains the first and second therapeutic agents in a ratio of from about 1:7 to about 7:1. In one embodiment, the synergistic pharmaceutical combination contains the first and second therapeutic agents in a ratio of from about 1:6 to about 6:1. In one embodiment, the synergistic pharmaceutical combination contains the first and second therapeutic agents in a ratio of from about 1:5 to about 5:1. In one embodiment, the synergistic pharmaceutical combination contains the first and second therapeutic agents in a ratio of from about 1:4 to about 4:1. In one embodiment, the synergistic pharmaceutical combination contains the first and second therapeutic agents in a ratio of from about 1:3 to about 3:1. In one embodiment, the synergistic pharmaceutical combination contains the first and second therapeutic agents in a ratio of from about 1:2 to about 2:1. In one embodiment, the synergistic pharmaceutical combination contains the first and second therapeutic agents in a ratio of approximately 1:1.

In some preferred embodiments, the second therapeutic agent is selected from the group consisting of Allopurinol, Arsenic Trioxide, Azacitidine, Bortezomib, Bevacizumab, Capecitabine, Carboplatin, Celecoxib, Chlorambucil, Clofarabine, Cytarabine, Dacarbazine, Daunorubicin HCl, Docetaxel, Doxorubicin HCl, Floxuridine, Gemcitabine HCl, Hydroxyurea, Ifosfamide, Imatinib Mesylate, Ixabepilone, Lenalidomide, Megestrol acetate, Methotrexate, Mitotane, Mitoxantrone HCl, Oxaliplatin, Paclitaxel, Pralatrexate, Romidepsin, Sorafenib, Streptozocin, Tamoxifen Citrate, Topotecan HCl, Tretinoin, Vandetanib, Vismodegib, Vorinostat, and combinations thereof.

In some preferred embodiments, the second therapeutic agent comprises a small molecule multi-kinase inhibitor. In one embodiment, the small molecule multi-kinase inhibitor comprises sorafenib or regorafenib. In some preferred embodiments, the second therapeutic agent comprises a Hedgehog Pathway Inhibitor. In one preferred embodiment, the Hedgehog Pathway Inhibitor comprises vismodegib.

In some preferred embodiments, the second therapeutic agent include members of the classes drugs listed in the following table 1.

TABLE 1

Classes Of Drugs That Have Demonstrated Synergy

| Classes of drugs | Examples |
|---|---|
| Purine analogs | Examples include, but are not limited to, allopurinol, oxypurinol, clofarabine, and tisopurine |
| Pyrimidine analogs | Examples include, but are not limited to, 5-fluorouracil, Floxuridine (FUDR), capecitabine, cytarabine, 6-azauracil (6-AU), and gemcitabine (Gemzar). |
| Proteasome inhibitors | Examples include, but are not limited to, bortezomib, carfilzomib, cediranib, disulfiram, epigallocatechin-3-gallate, salinosporamide A, ONCX 0912, CEP-18770, MLN9708, epoxomicin, and MG132. |
| Anti-angiogenic | Examples include, but are not limited to, bevacizumab, aflibercept, sunitinib, sorafenib, pazopanib, vandetanib, cabozantinib, axitinib, ponatinib, regorafenib, ranibizumab, lapatinib, and vandetanib. |
| Platinum-based antineoplastic drugs | Examples include, but are not limited to, cisplatin, carboplatin, oxaliplatin, satraplatin, picoplatin, nedaplatin, and triplatin. |
| COX-2 inhibitors | Examples include, but are not limited to, celecoxib, valdecoxib (Bextra), parecoxib (Dynastat), lumiracoxib, etoricoxib, and rofecoxib. |
| Nitrogen mustards | Examples include, but are not limited to, cyclophosphamide, chlorambucil, uramustine, ifosfamide, melphalan, bendamustine, and mustine. |
| Alkylating agents | Examples include, but are not limited to, cyclophosphamide, mechlorethamine or mustine (HN2) (trade name Mustardgen), uramustine or uracil mustard, melphalan, chlorambucil, ifosfamide, bendamustine, carmustine, lomustine, streptozocin, and busulfan. |
| Anthracyclines | Examples include, but are not limited to, Daunorubicin (Daunomycin), Daunorubicin (liposomal), Doxorubicin (Adriamycin), Doxorubicin (liposomal), Epirubicin, Idarubicin, Valrubicin, and Mitoxantrone. |
| Taxanes | Examples include, but are not limited to, Paclitaxel (Taxol), Docetaxel (Taxotere), and albumin-bound paclitaxel (Abraxane). |
| Nucleotide synthesis inhibitor | Examples include, but are not limited to, methotrexate, pralatrexate, hydroxyurea, and 5-fluorodeoxyuridine, 3,4-dihydroxybenzylamine. |
| Bcr-abl inhibitors | Examples include, but are not limited to, imatinib, nilotinib, dasatinib, bosutinib and ponatinib. |
| Other | Examples include, but are not limited to, arsenic trioxide, thalidomide, revlimid, and mitotane. |
| Topoisomerase inhibitor | Examples include, but are not limited to, amsacrine, etoposide, etoposide phosphate, teniposide, doxorubicin, Topotecan (Hycamtin), Irinotecan (CPT-11, Camptosar), Exatecan, Lurtotecan, ST 1481, CKD 602, ICRF-193, and genistein. |
| HDAC inhibitors | Examples include, but are not limited to, Vorinostat (SAHA), Romidepsin (Istodax), Panobinostat (LBH589), Valproic acid (as Mg valproate), Belinostat (PXD101), Mocetinostat (MGCD0103), Abexinostat (PCI-24781), Entinostat (MS-275), SB939, Resminostat (4SC-201), Givinostat, Quisinostat (JNJ-26481585), CUDC-101, AR-42, CHR-2845, CHR-3996, 4SC-202, CG200745, ACY-1215, ME-344, sulforaphane, Kevetrin, and ATRA. |
| Multi-kinase inhibitors | Examples include, but are not limited to, sorafenib, regorafenib, and vandetanib. |
| Hormone therapies | Examples include, but are not limited to, tamoxifen, toremifene, Arimidex (anastrozole), Aromasin (exemestane), Femara (letrozole), and Fulvestrant (Faslodex). |
| Hedgehog signaling Inhibitors | Examples include, but are not limited to, vismodegib, BMS-833923, IPI-926, LDE-225, PF-04449913, LEQ 506, and TAK-441. |

In some embodiments, the second therapeutic agent includes drugs that target tumor necrosis factor-related apoptosis-inducing ligand (TRAIL) receptors. In one embodiment, the second therapeutic agent includes a recombinant TRAIL or an agonistic antibody that activates one or more TRAIL receptors. In one embodiment, the second therapeutic agent includes one or more antibodies or recombinant TRAIL that activate signaling by DR4 and/or DR5. In one embodiment, the second therapeutic agent includes one or more of mapatumumab, lexatumumab, Apomab, AMG-655, LBY-135 and rhApo2L/TRAIL. In one embodiment, the second therapeutic agent includes an active agent selected from the group consisting of Camptothecin, 5-FU, capecitabine, cisplatin, doxorubicin, irinotecan, paclitaxel, cisplatin, bortezomib, BH3I-2, rituximab, radiation, triterpenoids, sorafenib, gemcitabine, HDAC inhibitors, carboplatin, T-101 (a gossypol derivate), ABT-263, ABT-737, and GX-15-070 (obatoclax), vorinostat, cetuximab, panitumumab, bevacizumab, ganitumab, interferon gamma, sorafenib, XIAP antagonists, Bcl-2 antagonists, and Smac mimetics.

II. Dose

In one embodiment, a pharmaceutical composition according to the invention comprises compound (1) or a pharmaceutically acceptable salt thereof in a dose ranging from about 100 mg to about 2000 mg, where the weight can, in certain embodiments be based on compound (1) in its free base form. In one embodiment, a pharmaceutical composition according to the invention comprises compound (1) or a pharmaceutically acceptable salt thereof in a dose ranging from about 40 mg to about 2000 mg, where the weight can, in certain embodiments be based on compound (1) in its free base form. In one embodiment, a pharmaceutical composition according to the invention comprises compound (1) or a pharmaceutically acceptable salt thereof in a dose ranging from about 50 mg to about 2000 mg, where the weight can, in certain embodiments be based on compound (1) in its free base form. In one embodiment, a pharmaceutical composition according to the invention comprises compound (1) or a pharmaceutically acceptable salt thereof in a dose ranging from about 60 mg to about 2000 mg, where the weight can, in certain embodiments be based on compound (1) in its free base form. In one embodiment, a pharmaceutical composition according to the invention comprises compound (1) or a pharmaceutically acceptable salt thereof in a dose level selected from the group consisting of from about 50 mg to about 200 mg, from about 50 mg to about 300 mg, from about 50 mg to about 400 mg, from about 50 mg to about 500 mg, from about 50 mg to about 600 mg, from about 50 mg to about 700 mg, from about 50 mg to about 800 mg, from about 50 mg to about 900 mg, from about 50 mg to about 1000 mg, from about 50 mg to about 1100 mg, from about 50 mg to about 1200 mg, from about 50 mg to about 1300 mg, from about 50 mg to about 1400 mg, from about 50 mg to about 1500 mg, from about 50 mg to about 1600 mg, from about 50 mg to about 1700 mg, from about 50 mg to about 1800 mg, and from about 50 mg to about 1900 mg, from 40 mg to 2000 mg. In one embodiment, a pharmaceutical composition according to the invention comprises compound (1) or a pharmaceutically acceptable salt thereof in a dose level selected from the group consisting of from about 40 mg to about 200 mg, from about 40 mg to about 300 mg, from about 40 mg to about 400 mg, from about 40 mg to about 500 mg, from about 40 mg to about 600 mg, from about 40 mg to about 700 mg, from about 40 mg to about 800 mg, from about 40 mg to about 900 mg, from about 40 mg to about 1000 mg, from about 40 mg to about 1100 mg, from about 40 mg to about 1200 mg, from about 40 mg to about 1300 mg, from about 40 mg to about 1400 mg, from about 40 mg to about 1500 mg, from about 40 mg to about 1600 mg, from about 40 mg to about 1700 mg, from about 40 mg to about 1800 mg, and from about 40 mg to about 1900 mg, from 40 mg to 2000 mg. In one embodiment, a pharmaceutical composition according to the invention comprises compound (1) or a pharmaceutically acceptable salt thereof in a dose level selected from the group consisting of from about 60 mg to about 200 mg, from about 60 mg to about 300 mg, from about 60 mg to about 400 mg, from about 60 mg to about 500 mg, from about 60 mg to about 600 mg, from about 60 mg to about 700 mg, from about 60 mg to about 800 mg, from about 60 mg to about 900 mg, from about 60 mg to about 1000 mg, from about 60 mg to about 1100 mg, from about 60 mg to about 1200 mg, from about 60 mg to about 1300 mg, from about 60 mg to about 1400 mg, from about 60 mg to about 1500 mg, from about 60 mg to about 1600 mg, from about 60 mg to about 1700 mg, from about 60 mg to about 1800 mg, and from about 60 mg to about 1900 mg, from 60 mg to 2000 mg. In one embodiment, a pharmaceutical composition according to the invention comprises compound (1) or a pharmaceutically acceptable salt thereof in a dose level selected from the group consisting of from about 100 mg to about 200 mg, from about 100 mg to about 300 mg, from about 100 mg to about 400 mg, from about 100 mg to about 500 mg, from about 100 mg to about 600 mg, from about 100 mg to about 700 mg, from about 100 mg to about 800 mg, from about 100 mg to about 900 mg, from about 100 mg to about 1000 mg, from about 100 mg to about 1100 mg, from about 100 mg to about 1200 mg, from about 100 mg to about 1300 mg, from about 100 mg to about 1400 mg, from about 100 mg to about 1500 mg, from about 100 mg to about 1600 mg, from about 100 mg to about 1700 mg, from about 100 mg to about 1800 mg, and from about 100 mg to about 1900 mg, from 50 mg to 2000 mg and from 40 mg to 200 mg. In one embodiment, a pharmaceutical composition according to the invention comprises compound (1) or a pharmaceutically acceptable salt thereof in a dose level selected from the group consisting of from about 200 mg to about 300 mg, from about 200 mg to about 400 mg, from about 200 mg to about 500 mg, from about 200 mg to about 600 mg, from about 200 mg to about 700 mg, from about 200 mg to about 800 mg, from about 200 mg to about 900 mg, from about 200 mg to about 1000 mg, from about 200 mg to about 1100 mg, from about 200 mg to about 1200 mg, from about 200 mg to about 1300 mg, from about 200 mg to about 1400 mg, from about 200 mg to about 1500 mg, from about 200 mg to about 1600 mg, from about 200 mg to about 1700 mg, from about 200 mg to about 1800 mg, and from about 200 mg to about 1900 mg based on compound (1) in its free base form. In one embodiment, a pharmaceutical composition according to the invention comprises compound (1) or a pharmaceutically acceptable salt thereof in a dose level selected from the group consisting of from about 400 mg to about 500 mg, from about 400 mg to about 600 mg, from about 400 mg to about 700 mg, from about 400 mg to about 800 mg, from about 400 mg to about 900 mg, from about 400 mg to about 1000 mg, from about 400 mg to about 1100 mg, from about 400 mg to about 1200 mg, from about 400 mg to about 1300 mg, from about 400 mg to about 1400 mg, from about 400 mg to about 1500 mg, from about 400 mg to about 1600 mg, from about 400 mg to about 1700 mg, from about 400 mg to about 1800 mg, and from about 400 mg to about 1900 mg based on compound (1) in its free base form. In one embodiment, a pharmaceutical composition according to the invention comprises compound (1) or a pharmaceutically acceptable salt thereof in a dose level selected from the group consisting of from about 50 mg to about 60 mg, from about 50 mg to about 70 mg, from about 50 mg to about 80 mg, from about 50 mg to about 90 mg, from about 50 mg to about 100 mg, from about 60 mg to about 70 mg, from about 60 mg to about 80 mg, from about 60 mg to about 90 mg, from about 60 mg to about 100 mg, from about 70 mg to about 80 mg, from about 70 mg to about 90 mg, from about 70 mg to about 100 mg, from about 80 mg to about 90 mg, from about 80 mg to about 100 mg, and from about 90 mg to about 100 mg In one embodiment, a pharmaceutical composition according to the invention comprises compound (1) or a pharmaceutically acceptable salt thereof in a dose ranging from about 1 mg/kg to about 40 mg/kg. In one embodiment, a pharmaceutical composition according to the invention comprises compound (1) or a pharmaceutically acceptable salt thereof in a dose level selected from the group consisting of from about 1 mg/Kg to about 40 mg/Kg, from about 2 mg/Kg to about 40 mg/Kg, from about 3 mg/Kg to about 40 mg/Kg, from about 4 mg/Kg to about 40 mg/Kg, from about 5 mg/Kg to about 40 mg/Kg, from about 6 mg/Kg to about 40 mg/Kg, from about 7 mg/Kg to about 40 mg/Kg, from about 8 mg/Kg to about 40 mg/Kg, from about 9 mg/Kg to about 40 mg/Kg, from about 10 mg/Kg to about 40 mg/Kg, from about 11 mg/Kg to about 40 mg/Kg, from about 12 mg/Kg to about 40 mg/Kg, from about 13 mg/Kg to about 40 mg/Kg, from about 14 mg/Kg to about 40 mg/Kg, from about 15 mg/Kg to about 40 mg/Kg, from about 16 mg/Kg to about 40 mg/Kg, from about 17 mg/Kg to about 40 mg/Kg, from about 18 mg/Kg to about 40 mg/Kg, from about 19 mg/Kg to about 40 mg/Kg, from about 20 mg/Kg to about 40 mg/Kg, from about 21 mg/Kg to about 40 mg/Kg, from about 22 mg/Kg to about 40 mg/Kg, from about 23 mg/Kg to about 40 mg/Kg, from about 24 mg/Kg to about 40 mg/Kg, from about 25 mg/Kg to about 40 mg/Kg, from about 26 mg/Kg to about 40 mg/Kg, from about 27 mg/Kg to about 40 mg/Kg, from about 28 mg/Kg to about 40 mg/Kg, from about 29 mg/Kg to about 40 mg/Kg, from about 30 mg/Kg to about 40 mg/Kg, from about 31 mg/Kg to about 40 mg/Kg, from about 32 mg/Kg to about 40 mg/Kg, from about 33 mg/Kg to about 40 mg/Kg, from about 34 mg/Kg to about 40 mg/Kg, from about 35 mg/Kg to about 40 mg/Kg, from about 36 mg/Kg to about 40 mg/Kg, from about 37 mg/Kg to about 40 mg/Kg, from about 38 mg/Kg to about 40 mg/Kg, and from about 39 mg/Kg to about 40 mg/Kg.

In one embodiment, a pharmaceutical composition according to the invention comprises compound (1) or a pharmaceutically acceptable salt thereof in a dose level selected from the group consisting of from about 1 mg/Kg to about 30 mg/Kg, from about 2 mg/Kg to about 30 mg/Kg, from about 3 mg/Kg to about 30 mg/Kg, from about 4 mg/Kg to about 30 mg/Kg, from about 5 mg/Kg to about 30 mg/Kg, from about 6 mg/Kg to about 30 mg/Kg, from about 7 mg/Kg to about 30 mg/Kg, from about 8 mg/Kg to about 30 mg/Kg, from about 9 mg/Kg to about 30 mg/Kg, from about 10 mg/Kg to about 30 mg/Kg, from about 11 mg/Kg to about 30 mg/Kg, from about 12 mg/Kg to about 30 mg/Kg, from about 13 mg/Kg to about 30 mg/Kg, from about 14 mg/Kg to about 30 mg/Kg, from about 15 mg/Kg to about 30 mg/Kg, from about 16 mg/Kg to about 30 mg/Kg, from about 17 mg/Kg to about 30 mg/Kg, from about 18 mg/Kg to about 30 mg/Kg, from about 19 mg/Kg to about 30 mg/Kg, from about 20 mg/Kg to about 30 mg/Kg, from about 21 mg/Kg to about 30 mg/Kg, from about 22 mg/Kg to about 30 mg/Kg, from about 23 mg/Kg to about 30 mg/Kg, from about 24 mg/Kg to about 30 mg/Kg, from about 25 mg/Kg to about 30 mg/Kg, from about 26 mg/Kg to about 30 mg/Kg, from about 27 mg/Kg to about 30 mg/Kg, from about 28 mg/Kg to about 30 mg/Kg, and from about 29 mg/Kg to about 30 mg/Kg.

In one embodiment, a pharmaceutical composition according to the invention comprises compound (1) or a pharmaceutically acceptable salt thereof in a dose level selected from the group consisting of from about 1 mg/Kg to about 20 mg/Kg, from about 2 mg/Kg to about 20 mg/Kg, from about 3 mg/Kg to about 20 mg/Kg, from about 4 mg/Kg to about 20 mg/Kg, from about 5 mg/Kg to about 20 mg/Kg, from about 6 mg/Kg to about 20 mg/Kg, from about 7 mg/Kg to about 20 mg/Kg, from about 8 mg/Kg to about 20 mg/Kg, from about 9 mg/Kg to about 20 mg/Kg, from about 10 mg/Kg to about 20 mg/Kg, from about 11 mg/Kg to about 20 mg/Kg, from about 12 mg/Kg to about 20 mg/Kg, from about 13 mg/Kg to about 20 mg/Kg, from about 14 mg/Kg to about 20 mg/Kg, from about 15 mg/Kg to about 20 mg/Kg, from about 16 mg/Kg to about 20 mg/Kg, from about 17 mg/Kg to about 20 mg/Kg, from about 18 mg/Kg to about 20 mg/Kg, and from about 19 mg/Kg to about 20 mg/Kg.

In one embodiment, a pharmaceutical composition according to the invention comprises compound (1) or a pharmaceutically acceptable salt thereof in a dose level selected from the group consisting of from about 1 mg/Kg to about 10 mg/Kg, from about 2 mg/Kg to about 10 mg/Kg, from about 3 mg/Kg to about 10 mg/Kg, from about 4 mg/Kg to about 10 mg/Kg, from about 5 mg/Kg to about 10 mg/Kg, from about 6 mg/Kg to about 10 mg/Kg, from about 7 mg/Kg to about 10 mg/Kg, from about 8 mg/Kg to about 10 mg/Kg, and from about 9 mg/Kg to about 10 mg/Kg.

In one embodiment, a pharmaceutical composition according to the invention comprises compound (1) or a pharmaceutically acceptable salt thereof in a dose level ranging from about 37.5 mg/m$^2$ to about 1500 mg/m$^2$. In one embodiment, a pharmaceutical composition according to the invention comprises compound (1) or a pharmaceutically acceptable salt thereof in a dose level selected from the group consisting of from about from about 40 mg/m$^2$ to about 1500 mg/m$^2$, from about 45 mg/m$^2$ to about 1500 mg/m$^2$, from about 50 mg/m$^2$ to about 1500 mg/m$^2$, from about 55 mg/m$^2$ to about 1500 mg/m$^2$, from about 60 mg/m$^2$ to about 1500 mg/m$^2$, from about 65 mg/m$^2$ to about 1500 mg/m$^2$, from about 70 mg/m$^2$ to about 1500 mg/m$^2$, from about 75 mg/m$^2$ to about 1500 mg/m$^2$, from about 80 mg/m$^2$ to about 1500 mg/m$^2$, from about 85 mg/m$^2$ to about 1500 mg/m$^2$, from about 90 mg/m$^2$ to about 1500 mg/m$^2$, from about 95 mg/m$^2$ to about 1500 mg/m$^2$, from about 100 mg/m$^2$ to about 1500 mg/m$^2$, from about 105 mg/m$^2$ to about 1500 mg/m$^2$, from about 110 mg/m$^2$ to about 1500 mg/m$^2$, from about 115 mg/m$^2$ to about 1500 mg/m$^2$, from about 120 mg/m$^2$ to about 1500 mg/m$^2$, from about 125 mg/m$^2$ to about 1500 mg/m$^2$, from about 130 mg/m$^2$ to about 1500 mg/m$^2$, from about 135 mg/m$^2$ to about 1500 mg/m$^2$, from about 140 mg/m$^2$ to about 1500 mg/m$^2$, from about 145 mg/m$^2$ to about 1500 mg/m$^2$, from about 150 mg/m$^2$ to about 1500 mg/m$^2$, from about 155 mg/m$^2$ to about 1500 mg/m$^2$, from about 160 mg/m$^2$ to about 1500 mg/m$^2$, from about 165 mg/m$^2$ to about 1500 mg/m$^2$, from about 170 mg/m$^2$ to about 1500 mg/m$^2$, from about 175 mg/m$^2$ to about 1500 mg/m$^2$, from about 180 mg/m$^2$ to about 1500 mg/m$^2$, from about 185 mg/m$^2$ to about 1500 mg/m$^2$, from about 190 mg/m$^2$ to about 1500 mg/m$^2$, from about 195 mg/m$^2$ to about 1500 mg/m$^2$, from about 200 mg/m$^2$ to about 1500 mg/m$^2$, from about 205 mg/m$^2$ to about 1500 mg/m$^2$, from about 210 mg/m$^2$ to about 1500 mg/m$^2$, from about 215 mg/m$^2$ to about 1500 mg/m$^2$, from about 220 mg/m$^2$ to about 1500 mg/m$^2$, from about 225 mg/m$^2$ to about 1500 mg/m$^2$, from about 230 mg/m$^2$ to about 1500 mg/m$^2$, from about 235 mg/m$^2$ to about 1500 mg/m$^2$, from about 240 mg/m$^2$ to about 1500 mg/m$^2$, from about 245 mg/m$^2$ to about 1500 mg/m$^2$, from about 250 mg/m$^2$ to about 1500 mg/m$^2$, from about 255 mg/m$^2$ to about 1500 mg/m$^2$, from about 260 mg/m² to about 1500 mg/m², from about 265 mg/m² to about 1500 mg/m², from about 270 mg/m² to about 1500 mg/m², from about 275 mg/m² to about 1500 mg/m², from about 280 mg/m² to about 1500 mg/m², from about 285 mg/m² to about 1500 mg/m², from about 290 mg/m² to about 1500 mg/m², from about 295 mg/m² to about 1500 mg/m², from about 300 mg/m² to about 1500 mg/m², from about 305 mg/m² to about 1500 mg/m², from about 310 mg/m² to about 1500 mg/m², from about 315 mg/m² to about 1500 mg/m², from about 320 mg/m² to about 1500 mg/m², from about 325 mg/m² to about 1500 mg/m², from about 330 mg/m² to about 1500 mg/m², from about 335 mg/m² to about 1500 mg/m², from about 340 mg/m² to about 1500 mg/m², from about 345 mg/m² to about 1500 mg/m², from about 350 mg/m² to about 1500 mg/m², from about 355 mg/m² to about 1500 mg/m², from about 360 mg/m² to about 1500 mg/m², from about 365 mg/m² to about 1500 mg/m², from about 370 mg/m² to about 1500 mg/m², from about 375 mg/m² to about 1500 mg/m², from about 380 mg/m² to about 1500 mg/m², from about 385 mg/m² to about 1500 mg/m², from about 390 mg/m² to about 1500 mg/m², from about 395 mg/m² to about 1500 mg/m², from about 400 mg/m² to about 1500 mg/m², from about 405 mg/m² to about 1500 mg/m², from about 410 mg/m² to about 1500 mg/m², from about 415 mg/m² to about 1500 mg/m², from about 420 mg/m² to about 1500 mg/m², from about 425 mg/m² to about 1500 mg/m², from about 430 mg/m² to about 1500 mg/m², from about 435 mg/m² to about 1500 mg/m², from about 440 mg/m² to about 1500 mg/m², from about 445 mg/m² to about 1500 mg/m², from about 450 mg/m² to about 1500 mg/m², from about 455 mg/m² to about 1500 mg/m², from about 460 mg/m² to about 1500 mg/m², from about 465 mg/m² to about 1500 mg/m², from about 470 mg/m² to about 1500 mg/m², from about 475 mg/m² to about 1500 mg/m², from about 480 mg/m² to about 1500 mg/m², from about 485 mg/m² to about 1500 mg/m², from about 490 mg/m² to about 1500 mg/m², from about 495 mg/m² to about 1500 mg/m², from about 500 mg/m² to about 1500 mg/m², from about 505 mg/m² to about 1500 mg/m², from about 510 mg/m² to about 1500 mg/m², from about 515 mg/m² to about 1500 mg/m², from about 520 mg/m² to about 1500 mg/m², from about 525 mg/m² to about 1500 mg/m², from about 530 mg/m² to about 1500 mg/m², from about 535 mg/m² to about 1500 mg/m², from about 540 mg/m² to about 1500 mg/m², from about 545 mg/m² to about 1500 mg/m², from about 550 mg/m² to about 1500 mg/m², from about 555 mg/m² to about 1500 mg/m², from about 560 mg/m² to about 1500 mg/m², from about 565 mg/m² to about 1500 mg/m², from about 570 mg/m² to about 1500 mg/m², from about 575 mg/m² to about 1500 mg/m², from about 580 mg/m² to about 1500 mg/m², from about 585 mg/m² to about 1500 mg/m², from about 590 mg/m² to about 1500 mg/m², from about 595 mg/m² to about 1500 mg/m², from about 600 mg/m² to about 1500 mg/m², from about 605 mg/m² to about 1500 mg/m², from about 610 mg/m² to about 1500 mg/m², from about 615 mg/m² to about 1500 mg/m², from about 620 mg/m² to about 1500 mg/m², from about 625 mg/m² to about 1500 mg/m², from about 630 mg/m² to about 1500 mg/m², from about 635 mg/m² to about 1500 mg/m², from about 640 mg/m² to about 1500 mg/m², from about 645 mg/m² to about 1500 mg/m², from about 650 mg/m² to about 1500 mg/m², from about 655 mg/m² to about 1500 mg/m², from about 660 mg/m² to about 1500 mg/m², from about 665 mg/m² to about 1500 mg/m², from about 670 mg/m² to about 1500 mg/m², from about 675 mg/m² to about 1500 mg/m², from about 680 mg/m² to about 1500 mg/m², from about 685 mg/m² to about 1500 mg/m², from about 690 mg/m² to about 1500 mg/m², from about 695 mg/m² to about 1500 mg/m², from about 700 mg/m² to about 1500 mg/m², from about 705 mg/m² to about 1500 mg/m², from about 710 mg/m² to about 1500 mg/m², from about 715 mg/m² to about 1500 mg/m², from about 720 mg/m² to about 1500 mg/m², from about 725 mg/m² to about 1500 mg/m², from about 730 mg/m² to about 1500 mg/m², from about 735 mg/m² to about 1500 mg/m², from about 740 mg/m² to about 1500 mg/m², from about 745 mg/m² to about 1500 mg/m², from about 750 mg/m² to about 1500 mg/m², from about 755 mg/m² to about 1500 mg/m², from about 760 mg/m² to about 1500 mg/m², from about 765 mg/m² to about 1500 mg/m², from about 770 mg/m² to about 1500 mg/m², from about 775 mg/m² to about 1500 mg/m², from about 780 mg/m² to about 1500 mg/m², from about 785 mg/m² to about 1500 mg/m², from about 790 mg/m² to about 1500 mg/m², from about 795 mg/m² to about 1500 mg/m², from about 800 mg/m² to about 1500 mg/m², from about 805 mg/m² to about 1500 mg/m², from about 810 mg/m² to about 1500 mg/m², from about 815 mg/m² to about 1500 mg/m², from about 820 mg/m² to about 1500 mg/m², from about 825 mg/m² to about 1500 mg/m², from about 830 mg/m² to about 1500 mg/m², from about 835 mg/m² to about 1500 mg/m², from about 840 mg/m² to about 1500 mg/m², from about 845 mg/m² to about 1500 mg/m², from about 850 mg/m² to about 1500 mg/m², from about 855 mg/m² to about 1500 mg/m², from about 860 mg/m² to about 1500 mg/m², from about 865 mg/m² to about 1500 mg/m², from about 870 mg/m² to about 1500 mg/m², from about 875 mg/m² to about 1500 mg/m², from about 880 mg/m² to about 1500 mg/m², from about 885 mg/m² to about 1500 mg/m², from about 890 mg/m² to about 1500 mg/m², from about 895 mg/m² to about 1500 mg/m², from about 900 mg/m² to about 1500 mg/m², from about 905 mg/m² to about 1500 mg/m², from about 910 mg/m² to about 1500 mg/m², from about 915 mg/m² to about 1500 mg/m², from about 920 mg/m² to about 1500 mg/m², from about 925 mg/m² to about 1500 mg/m², from about 930 mg/m² to about 1500 mg/m², from about 935 mg/m² to about 1500 mg/m², from about 940 mg/m² to about 1500 mg/m², from about 945 mg/m² to about 1500 mg/m², from about 950 mg/m² to about 1500 mg/m², from about 955 mg/m² to about 1500 mg/m², from about 960 mg/m² to about 1500 mg/m², from about 965 mg/m² to about 1500 mg/m², from about 970 mg/m² to about 1500 mg/m², from about 975 mg/m² to about 1500 mg/m², from about 980 mg/m² to about 1500 mg/m², from about 985 mg/m² to about 1500 mg/m², from about 990 mg/m² to about 1500 mg/m², from about 995 mg/m² to about 1500 mg/m², from about 1000 mg/m² to about 1500 mg/m², from about 1005 m g/m² to about 1500 mg/m², from about 1010 mg/m² to about 1500 mg/m², from about 1015 mg/m² to about 1500 mg/m², from about 1020 mg/m² to about 1500 mg/m², from about 1025 mg/m² to about 1500 mg/m², from about 1030 mg/m² to about 1500 mg/m², from about 1035 mg/m² to about 1500 mg/m², from about 1040 mg/m² to about 1500 mg/m², from about 1045 mg/m² to about 1500 mg/m², from about 1050 mg/m² to about 1500 mg/m², from about 1055 mg/m² to about 1500 mg/m², from about 1060 mg/m² to about 1500 mg/m², from about 1065 mg/m² to about 1500 mg/m², from about 1070 mg/m² to about 1500 mg/m², from about 1075 mg/m² to about 1500 mg/m², from about 1080 mg/m² to about 1500 mg/m², from about 1085 mg/m² to about 1500 mg/m², from about 1090 mg/m² to about 1500 mg/m², from about 1095 mg/m² to about 1500 mg/m², from about 1100 mg/m² to about 1500 mg/m², from about 1105 mg/m² to about 1500 mg/m², from about 1110 mg/m² to about 1500 mg/m², from about 1115 m g/m² to about 1500 mg/m², from about 1120 mg/m² to about 1500 mg/m², from about 1125 mg/m² to about 1500 mg/m², from about 1130 mg/m² to about 1500 mg/m², from about 1135 mg/m² to about 1500 mg/m², from about 1140 mg/m² to about 1500 mg/m², from about 1145 mg/m² to about 1500 mg/m², from about 1150 mg/m² to about 1500 mg/m², from about 1155 mg/m² to about 1500 mg/m², from about 1160 mg/m² to about 1500 mg/m², from about 1165 mg/m² to about 1500 mg/m², from about 1170 mg/m² to about 1500 mg/m², from about 1175 mg/m² to about 1500 mg/m², from about 1180 mg/m² to about 1500 mg/m², from about 1185 mg/m² to about 1500 mg/m², from about 1190 mg/m² to about 1500 mg/m², from about 1195 mg/m² to about 1500 mg/m², from about 1200 mg/m² to about 1500 mg/m², from about 1205 mg/m² to about 1500 mg/m², from about 1210 mg/m² to about 1500 mg/m², from about 1215 mg/m² to about 1500 mg/m², from about 1220 mg/m² to about 1500 mg/m², from about 1225 mg/m² to about 1500 mg/m², from about 1230 mg/m² to about 1500 mg/m², from about 1235 mg/m² to about 1500 mg/m², from about 1240 mg/m² to about 1500 mg/m², from about 1245 mg/m² to about 1500 mg/m², from about 1250 mg/m² to about 1500 mg/m², from about 1255 mg/m² to about 1500 mg/m², from about 1260 mg/m² to about 1500 mg/m², from about 1265 mg/m² to about 1500 mg/m², from about 1270 mg/m² to about 1500 mg/m², from about 1275 mg/m² to about 1500 mg/m², from about 1280 mg/m² to about 1500 mg/m², from about 1285 mg/m² to about 1500 mg/m², from about 1290 mg/m² to about 1500 mg/m², from about 1295 mg/m² to about 1500 mg/m², from about 1300 mg/m² to about 1500 mg/m², from about 1305 mg/m² to about 1500 mg/m², from about 1310 mg/m² to about 1500 mg/m², from about 1315 mg/m² to about 1500 mg/m², from about 1320 mg/m² to about 1500 mg/m², from about 1325 m g/m² to about 1500 mg/m², from about 1330 mg/m² to about 1500 mg/m², from about 1335 mg/m² to about 1500 mg/m², from about 1340 mg/m² to about 1500 mg/m², from about 1345 mg/m² to about 1500 mg/m², from about 1350 mg/m² to about 1500 mg/m², from about 1355 mg/m² to about 1500 mg/m², from about 1360 mg/m² to about 1500 mg/m², from about 1365 mg/m² to about 1500 mg/m², from about 1370 mg/m² to about 1500 mg/m², from about 1375 mg/m² to about 1500 mg/m², from about 1380 mg/m² to about 1500 mg/m², from about 1385 mg/m² to about 1500 mg/m², from about 1390 mg/m² to about 1500 mg/m², from about 1395 mg/m² to about 1500 mg/m², from about 1400 mg/m² to about 1500 mg/m², from about 1405 m g/m² to about 1500 mg/m², from about 1410 mg/m² to about 1500 mg/m², from about 1415 mg/m² to about 1500 mg/m², from about 1420 mg/m² to about 1500 mg/m², from about 1425 mg/m² to about 1500 mg/m², from about 1430 mg/m² to about 1500 mg/m², from about 1435 mg/m² to about 1500 mg/m², from about 1440 mg/m² to about 1500 mg/m², from about 1445 mg/m² to about 1500 mg/m², from about 1450 mg/m² to about 1500 mg/m², from about 1455 mg/m² to about 1500 mg/m², from about 1460 mg/m² to about 1500 mg/m², from about 1465 mg/m² to about 1500 mg/m², from about 1470 mg/m² to about 1500 mg/m², from about 1475 mg/m² to about 1500 mg/m², from about 1480 mg/m² to about 1500 mg/m², from about 1485 mg/m² to about 1500 mg/m², from about 1490 mg/m² to about 1500 mg/m², and from about 1495 mg/m² to about 1500 mg/m².

III. Dosage Forms

Suitable pharmaceutical compositions for use with the methods of the present invention can be formulated into any dosage form that can be administered to a patient. In one embodiment, the pharmaceutical composition is in the form of an oral dosage unit or parenteral dosage unit. In one embodiment, the pharmaceutical composition is in the form of an oral dosage unit. In some embodiments, an oral dosage unit is fractionated into several, smaller doses, which are administered to a subject over a predetermined period of time in order to reduce toxicity of the therapeutic agent being administered. In some embodiments, an oral dosage unit is administered by a tablet or capsule comprising a controlled release formulation that can include a plurality of particles, granules, pellets, minitablets or tablets. In one embodiment, the pharmaceutical composition is in the form of a parenteral dosage unit. In one embodiment, the pharmaceutical composition is in the form of a parenteral dosage unit, wherein the parenteral dosage unit is selected from the group consisting of intravenous (IV), subcutaneous (SC), and intramuscular (M), rectal (PR) and transdermal dosage units. In one embodiment, the pharmaceutical composition is in a dosage form selected from the group consisting of sterile solutions, suspensions, suppositories, tablets and capsules. In one embodiment, the composition is an oral dosage form selected from the group consisting of a tablet, caplet, capsule, lozenge, syrup, liquid, suspension and elixir. In one embodiment, the composition is in an oral dosage form selected from the group consisting of tablets, hard shell capsules, soft gelatin capsules, beads, granules, aggregates, powders, gels, solids and semi-solids.

In some embodiments, suitable foil is of pharmaceutical compositions for use in the methods of the present invention include dermatological compositions adapted for cutaneous topical administration. In some such embodiments, dermatological compositions include a cosmetically or pharmaceutically acceptable medium. In some embodiments, the dermatological compositions for topical administration can include ointments, lotions, creams, gels, drops, suppositories, sprays, liquids and powders. In some embodiments, conventional pharmaceutical carriers, aqueous, powder or oily bases, thickeners, skin enhancers and the like can be necessary or desirable and therefore can be used. Examples of suitable enhancers include, but are not limited to, ethers such as diethylene glycol monoethyl ether (available commercially as Transcutol®) and diethylene glycol monomethyl ether; surfactants such as sodium laurate, sodium lauryl sulfate, cetyltrimethylammonium bromide, benzalkonium chloride, Poloxamer (231, 182, 184), Tween (20, 40, 60, 80), and lecithin (U.S. Pat. No. 4,783,450); alcohols such as ethanol, propanol, octanol, benzyl alcohol, and the like; polyethylene glycol and esters thereof such as polyethylene glycol monolaurate; amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine; terpenes; alkanones; and organic acids, particularly citric acid and succinic acid. Azone® and sulfoxides such as DMSO and C₁ 0MSO may also be used, but are less preferred.

In some embodiments, the pharmaceutical composition of the present invention is in a dosage form selected from the group consisting of sustained release forms, controlled release forms, delayed release forms and response release forms.

IV. Methods of Use

The compositions and methods of the present invention have utility in treating many disease conditions, including cancer (e.g., colorectal, brain, and glioblastoma). In one embodiment, the compositions and methods of the present invention are used to treat diseases such as ocular melanoma, desmoplastic round cell tumor, chondrosarcoma, leptomengial disease, diffuse large B-cell lymphoma, Acute Lymphoblastic Leukemia, Acute Myeloid Leukemia, Adrenocortical Carcinoma, AIDS-Related Cancers, AIDS-Related Lymphoma, Anal or Rectal Cancer, Appendix Cancer, Astrocytomas, and Atypical Teratoid/Rhabdoid Tumor. In one embodiment, the compositions and methods of the present invention are used to treat diseases such as Basal Cell Carcinoma, Basal Cell Nevus Syndrome, Gorlin-Nevus Syndrome, Bile Duct Cancer, Bladder Cancer, Bone Cancer, Osteosarcoma and Malignant Fibrous Histiocytoma, Brain Tumor, Breast Cancer, Bronchial Tumors, Burkitt Lymphoma, and Spinal Cord Tumors. In one embodiment, the compositions and methods of the present invention are used to treat diseases such as Carcinoid Tumor, Carcinoma of Unknown Primary, Central Nervous System Atypical Teratoid/Rhabdoid Tumor, Leptomeningeal Disease, Central Nervous System Embryonal Tumors, Central Nervous System Lymphoma, Cervical Cancer, Chordoma, Chronic Lymphocytic Leukemia, Chronic Myelogenous Leukemia, Chronic Myeloproliferative Disorders, Colon Cancer, Colorectal Cancer, Craniopharyngioma, and Cutaneous T-Cell Lymphoma (including, but not limited to, Sezary syndrome and mycosis fungoides (MF)). In one embodiment, the compositions and methods of the present invention are used to treat diseases such as Embryonal Tumors of Central Nervous System, Endometrial Cancer, Ependymoblastoma, Ependymoma, Esophageal Cancer, Ewing Sarcoma Family of Tumors, Extracranial Germ Cell Tumor, Extragonadal Germ Cell Tumor, Extrahepatic Bile Duct Cancer, and Eye Cancer. In one embodiment, the compositions and methods of the present invention are used to treat diseases such as Gallbladder Cancer, Gastric (Stomach) Cancer, Gastrointestinal Carcinoid Tumor, Gastrointestinal Stromal Tumor (GIST), Germ Cell Tumor, Gestational Trophoblastic Tumor, and Glioma. In one embodiment, the compositions and methods of the present invention are used to treat cancer selected from the group consisting of Hairy Cell Leukemia, Head and Neck Cancer, Hepatocellular (Liver) Cancer, Histiocytosis, Hodgkin Lymphoma, and Hypopharyngeal Cancer. In one embodiment, the compositions and methods of the present invention are used to treat diseases such as Kaposi Sarcoma, and Kidney (Renal Cell) Cancer. In one embodiment, the compositions and methods of the present invention are used to treat diseases such as Langerhans Cell Histiocytosis, Laryngeal Cancer, Lip and Oral Cavity Cancer, Liver Cancer, Lung Cancer, Non-Hodgkin Lymphoma, and Primary Central Nervous System Lymphoma. In one embodiment, the compositions and methods of the present invention are used to treat diseases such as Waldenström's macroglobulinemia (lymphoplasmacytic lymphoma), Malignant Fibrous Histiocytoma of Bone and Osteosarcoma, Medulloblastoma, Medulloepithelioma, Melanoma, Merkel Cell Carcinoma, Mesothelioma, Metastatic Squamous Neck Cancer with Occult Primary, Multiple Endocrine Neoplasia Syndrome, Mouth Cancer, Multiple Myeloma/Plasma Cell Neoplasm, Mycosis Fungoides, Myelodysplastic Syndromes, Myelodysplastic/Myeloproliferative Neoplasms, Multiple Myeloma, and Myeloproliferative Disorders. In one embodiment, the compositions and methods of the present invention are used to treat cancer. In one embodiment, the compositions and methods of the present invention are used to treat diseases such as Nasal Cavity and Paranasal Sinus Cancer, Nasopharyngeal Cancer, and Neuroblastoma. In one embodiment, the compositions and methods of the present invention are used to treat diseases such as Oral Cancer, Lip and Oral Cavity Cancer, Oropharyngeal Cancer, Osteosarcoma and Malignant Fibrous Histiocytoma of Bone, Ovarian Cancer, Ovarian Germ Cell Tumor, Ovarian Epithelial Cancer, and Ovarian Low Malignant Potential Tumor. In one embodiment, the compositions and methods of the present invention are used to treat diseases such as Pancreatic Cancer, Papillomatosis, Paranasal Sinus and Nasal Cavity Cancer, Parathyroid Cancer, Penile Cancer, Pharyngeal Cancer, Pineal Parenchymal Tumors of Intermediate Differentiation, Pineoblastoma and Supratentorial Primitive Neuroectodermal Tumors, Pituitary Tumor, Pleuropulmonary Blastoma, Pregnancy and Breast Cancer, Primary Central Nervous System Lymphoma, and Prostate Cancer. In one embodiment, the compositions and methods of the present invention are used to treat cancer selected from the group consisting of Rectal Cancer, Renal Cell (Kidney) Cancer, Renal Pelvis and Ureter, Respiratory Tract Carcinoma Involving the NUT Gene on Chromosome 15, Retinoblastoma, and Rhabdomyo sarcoma. In one embodiment, the compositions and methods of the present invention are used to treat high grade prostate cancer. In one embodiment, the compositions and methods of the present invention are used to treat medium grade prostate cancer. In one embodiment, the compositions and methods of the present invention are used to treat low grade prostate cancer. In one embodiment, the compositions and methods of the present invention are used to treat castration-resistant prostate cancer.

In one embodiment, the compositions and methods of the present invention are used to treat a proliferative skin disorder. In one embodiment, the compositions and methods of the present invention are used to treat a proliferative skin disorder, wherein the proliferative skin disorder is psoriasis. In one embodiment, the compositions and methods of the present invention are used to treat cancer selected from the group consisting of Salivary Gland Cancer, Sarcoma, Sézary Syndrome, Skin Cancer, Ocular Cancer, Skin Carcinoma, Small Intestine Cancer, Soft Tissue Sarcoma, Squamous Cell Carcinoma, Squamous Neck Cancer with Occult Primary, and Supratentorial Primitive Neuroectodermal Tumors. In one embodiment, the compositions and methods of the present invention are used to treat cancer selected from the group consisting of T-Cell Lymphoma, Testicular Cancer, Throat Cancer, Thymoma and Thymic Carcinoma, Thyroid Cancer, Transitional Cell Cancer of the Renal Pelvis and Ureter, and Gestational Trophoblastic Tumor. In one embodiment, the compositions and methods of the present invention are used to treat cancer selected from the group consisting of Carcinoma of Unknown Primary Site, Cancer of Unknown Primary Site, Unusual Cancers of Childhood, Transitional Cell Cancer Of the Renal Pelvis and Ureter, Urethral Cancer, and Uterine Sarcoma. In one embodiment, the compositions and methods of the present invention are used to treat cancer selected from the group consisting of Vaginal Cancer, and Vulvar Cancer. In one embodiment, the compositions and methods of the present invention are used to treat cancer selected from the group consisting of Wilms Tumor, and Women's Cancers.

In some embodiments, the compositions and methods of the present invention are used as a first-line therapy (sometimes called primary therapy). In some embodiments, the compositions and methods of the present invention are used as a second-line therapy. In some embodiments, the compositions and methods of the present invention are used as a third-line therapy. In some embodiments, the compositions and methods of the present invention are used as a salvage therapy. The term "salvage therapy" as used herein means a therapeutic agent that can be taken with any regimen after a subject's initial treatment regimen has failed or after the subject's condition has not responded to an initial treatment. In some embodiments, the compositions and methods of the present invention are used as a rescue therapy. In one embodiment of the rescue therapy, the compositions of the present invention are used as a rescue agent to counteract the action of an initial treatment. In one embodiment of the rescue therapy, the compositions of the present invention are used as rescue agent which is administered to a subject who has developed resistance to a standard or an initial treatment. In some embodiments, the compositions and methods of the present invention are used as a neoadjuvant therapy. In one embodiment, the neoadjuvant therapy comprises administration of one or more of the therapeutic agents of the present invention to a subject before a main or first line treatment. In one embodiment, the neoadjuvant therapy reduces the size or extent of the cancer being treated before a main or first line treatment is administered to the subject undergoing treatment. In some embodiments, the compositions and methods of the present invention are used as an adjuvant therapy. In one embodiment, the adjuvant therapy comprises administration of one or more therapeutic agents of the present invention to a subject, wherein the one or more therapeutic agent that modify the effect of other therapeutic agents that are already administered to the subject or are concurrently administered to the subject or subsequently administered to the subject.

In some embodiments, the compositions and methods of the present invention exhibit reduced chance of drug-drug interactions. In some embodiments, the compositions and methods of the present invention, compound (1) and/or a pharmaceutically acceptable salt thereof are eliminated from the patient's body before it can interact with another pharmaceutically active agent.

In some embodiments, the compositions and methods of the present invention, compound (1) and/or a pharmaceutically acceptable salt thereof exhibit tonicity level that facilitates combinations with other pharmaceutical agents.

The utility of the methods and compositions of the present invention is not limited to any particular animal species. In one embodiment, a subject treated according to methods and using compositions of the present invention, can be mammalian or non-mammalian. In one embodiment, a mammalian subject can be any mammal including, but not limited to, a human; a non-human primate; a rodent such as a mouse, rat, or guinea pig; a domesticated pet such as a cat or dog; a horse, cow, pig, sheep, goat, or rabbit. In one embodiment, a non-mammalian subject can be any non-mammal including, but not limited to, a bird such as a duck, goose, chicken, or turkey. In one embodiment, subjects can be either gender and can be any age. The composition and methods can also be used to prevent cancer. The composition and methods can also be used to stimulate the immune system.

The utility of the methods and compositions of the present invention is not limited to any particular age of the subject. In one embodiment, a subject treated according to methods and using compositions of the present invention can be over the age of 50 years, over the age of 55 years, over the age of 60 years, or over the age of 65 years. In one embodiment a subject treated according to methods and using compositions of the present invention can be under the age of 50 years, under the age of 55 years, under the age of 60 years, or under the age of 65 years.

In one embodiment the subject has received at least one prior therapeutic agent. In one embodiment the subject has received at least two, at least three, or at least four prior therapeutic agents. In one embodiment the prior therapeutic agent is ibrutinib, bortezomib, carfilzomib, temozolomide, bevacizumab, cyclophosphamide, hydroxydaunorubicin, vincristine, prednisone, cytarabine, cisplatin, rituximab, 5-fluorouracil, oxaliplatin, leucovorin, or lenalidomide.

In one embodiment the subject has been treated with radiation. In one embodiment the subject has been treated with surgery.

In some embodiments of the methods of treating a cancer, the cancer no longer responds to treatment with ibrutinib, bortezomib, carfilzomib, temozolomide, bevacizumab, cyclophosphamide, hydroxydaunorubicin, vincristine, prednisone, cytarabine, cisplatin, rituximab, 5-fluorouracil, oxaliplatin, leucovorin, lenalidomide, radiation, surgery, or a combination thereof.

In some embodiments, the compositions and methods of the present invention have dose response relation in cancer cells that is different from dose response relation of the same the compositions and methods in normal cells. FIG. 1, for example, illustrates the dose response relation in which effects of exemplary compound (1) on proliferation and cell death in normal and tumor cells. FIG. 1 shows cell viability following treatment with exemplary compound (1) at indicated concentrations for 72 hours. The tumors tested included a human colon cancer cell line (HCT116), breast tumor cell line (MDA-MB-231), human primary glioblastoma cell line (U87). And the normal cells tested included human foreskin fibroblasts (HFF), human fetal lung fibroblast (MRC-5) cells, and human lung fibroblast cell line (WI-38). Doxorubicin was used as a positive control at 1 μg/mL in normal fibroblasts. As, shown in FIG. 1, cell viability of normal cells tested is at least about 75% at about 1-5 mg/mL concentration of exemplary compound (1) whereas viability of tumor cells is significantly lower (e.g., at or below 50%) at the same concentration of exemplary compound (1). Moreover, as concentration of exemplary compound (1) is increased beyond about 5 mg/mL viability of tumor cells falls to below 25% whereas viability of normal cells remains at about 75%.

Figure 2:
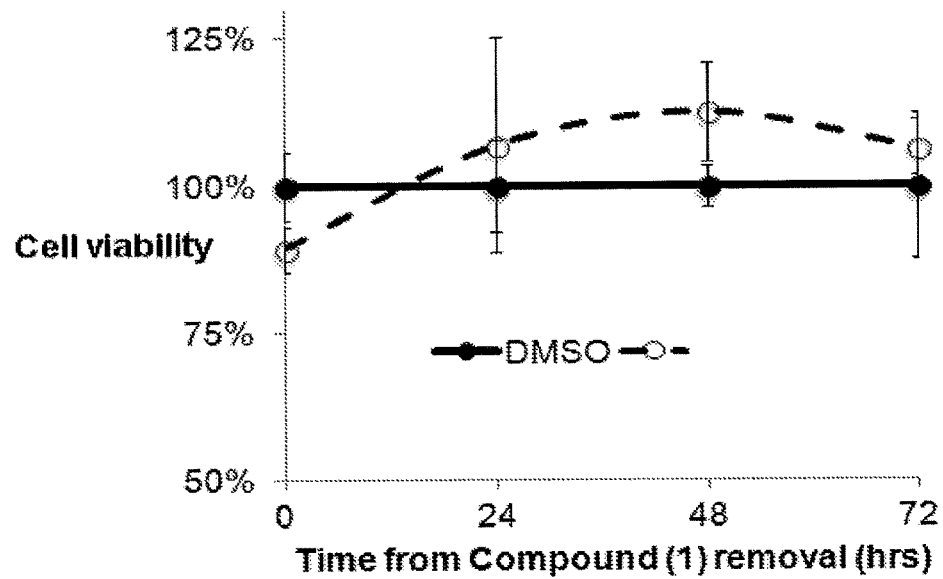
FIG. 2 illustrates cell viability assay in human fetal lung fibroblast (MRC-5) cells following 72 hour treatment with an exemplary compound of the present invention, compound (1).

FIG. 2 illustrates cell viability assay in human fetal lung fibroblast (MRC-5) cells following 72 hour treatment with exemplary compound (1) (5 μM) or DMSO and the indicated recovery period in complete drug-free media after this treatment. The time points are given as time following removal of exemplary compound (1) after 72 hour treatment. As shown in FIG. 2, cell recovery was seen with exemplary compound (1), but not with DMSO.

In some embodiments, the compositions and methods of the present invention have utility in treating cancer in a subject. In one embodiment, the compositions and methods of the present invention have utility in treating cancer in a human subject. In one embodiment, the method of treatment comprises administering to a subject in need of such treatment: (i) a first therapeutic agent including a compound comprising compound (1) or a pharmaceutically acceptable salt thereof in combination with (ii) a second therapeutic agent, wherein the first therapeutic agent and the second therapeutic agent are administered either simultaneously or sequentially. The second therapeutic agent can be any suitable therapeutic agent, including any of the pharmaceutically active agents disclosed in this application. In one embodiment, the pharmaceutically acceptable salt of compound (1) includes a di-hydrochloride salt having the structure of compound (2):

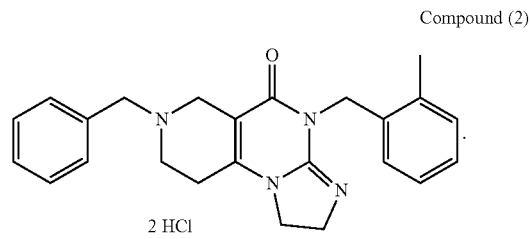 [SMILES: Cc1ccccc1CN1C(=O)C2=C(CCN(Cc3ccccc3)C2)N2CCN=C12]

Compound (2)

It is understood that compound (2), or an alternative di-salt thereof apparent from the teaching of this disclosure, can be substituted for a compound (1) in any of the compositions or dosing regimens described herein.

In some embodiments, the method of treatment comprises administering to a subject in need of such treatment, a pharmaceutically effective amount of compound (1) or a pharmaceutically acceptable salt thereof and a pharmaceutically acceptable carrier.

In some embodiments, the method of treatment of the present invention comprises administering a synergistic pharmaceutical combination, either simultaneously or sequentially, to a subject in need of such treatment, wherein the synergistic pharmaceutical combination comprising (i) a first therapeutic agent comprising compound (1) or a pharmaceutically acceptable salt thereof; and (ii) a second therapeutic agent. In one embodiment, the method of treatment comprises administering to a subject in need of such treatment, either simultaneously or sequentially, therapeutically synergistic effective amounts of a first therapeutic agent comprising compound (1) or a pharmaceutically acceptable salt thereof in combination with a second therapeutic agent. In one embodiment, the method of treatment comprises administering to a subject in need of such treatment an effective amount of a first therapeutic agent comprising compound (1) or a pharmaceutically acceptable salt thereof in combination with an effective amount of a second therapeutic agent, wherein the combination provides a synergistic effect in the in vivo treatment of cancer sensitive to the combination, and wherein the first therapeutic agent and the second therapeutic agent are administered either simultaneously or sequentially. In one embodiment, the method of treatment comprises administering to a subject in need of such treatment an effective amount of a first therapeutic agent comprising compound (1) or a pharmaceutically acceptable salt thereof in combination with an effective amount of a second therapeutic agent, wherein the combination provides a synergistic effect in the in vivo treatment of a minimal residual disease sensitive to the combination, and wherein the first therapeutic agent and the second therapeutic agent are administered either simultaneously or sequentially.

In some embodiments, the second drug can be given before or prior to compound (1).

In one embodiment, the method of treatment of the present invention targets cancer, wherein the cancer is selected from the group consisting of solid tumors, liquid tumors, lymphomas, leukemias, or myelomas.

In one embodiment, the method of treatment of the present invention targets a solid tumor, wherein the solid tumor is selected from the group consisting of: Cervical Cancer, Endometrial Cancer, Extracranial Germ Cell Tumor; Extragonadal Germ Cell Tumor; Germ Cell Tumor; Gestational Trophoblastic Tumor; Ovarian Cancer, Ovarian Germ Cell Tumor, Ovarian Epithelial Cancer, and Ovarian Low Malignant Potential Tumor; Penile Cancer, Prostate Cancer; Pregnancy and Breast Cancer; high grade prostate cancer; medium grade prostate cancer; low grade prostate cancer; castration-resistant prostate cancer; Breast Cancer; Bile Duct Cancer; Extrahepatic Bile Duct Cancer; Gallbladder Cancer; Hepatocellular (Liver) Cancer; Kidney (Renal Cell) Cancer; Liver Cancer, Renal Cell (Kidney) Cancer, Renal Pelvis and Ureter; Basal Cell Carcinoma; Basal Cell Nevus Syndrome, Gorlin-Nevus Syndrome, Melanoma, Merkel Cell Carcinoma, Papillomatosis, Multiple Endocrine Neoplasia Syndrome; Pancreatic Cancer, Parathyroid Cancer, ocular melanoma; Eye Cancer; Retinoblastoma; Malignant Fibrous Histiocytoma; Ewing Sarcoma Family of Tumors; desmoplastic round cell tumor; chondrosarcoma, Kaposi Sarcoma, Rhabdomyosarcoma; Spinal Cord Tumors, Leptomeningeal Disease, Central Nervous System Embryonal Tumors, Chordoma, Embryonal Tumors of Central Nervous System, Ependymoblastoma, Ependymoma, Neuroblastoma; Pineal Parenchymal Tumors of Intermediate Differentiation, Pineoblastoma; Adrenocortical Carcinoma; Bone Cancer, Osteosarcoma; Malignant Fibrous Histiocytoma of Bone and Osteosarcoma; Osteosarcoma and Malignant Fibrous Histiocytoma of Bone; Carcinoid Tumor, Carcinoma of Unknown Primary, Bronchial Tumors, Lung Cancer, Pleuropulmonary Blastoma; Respiratory Tract Carcinoma Involving the NUT Gene on Chromosome 15, Astrocytomas, Atypical Teratoid/Rhabdoid Tumor; Central Nervous System Atypical Teratoid/Rhabdoid Tumor, Craniopharyngioma, Glioma, Brain cancer, Medulloblastoma, Medulloepithelioma, Supratentorial Primitive Neuroectodermal Tumors; Pituitary Tumor; Gastric (Stomach) Cancer, Gastrointestinal Carcinoid Tumor, Gastrointestinal Stromal Tumor (GIST), Bladder Cancer, Anal or Rectal Cancer, Appendix Cancer, Esophageal Cancer, Hypopharyngeal Cancer; Laryngeal Cancer, Lip and Oral Cavity Cancer, Metastatic Squamous Neck Cancer with Occult Primary, Mouth Cancer, Nasal Cavity and Paranasal Sinus Cancer, Nasopharyngeal Cancer, Oral Cancer, Lip and Oral Cavity Cancer, Oropharyngeal Cancer, Paranasal Sinus and Nasal Cavity Cancer, Pharyngeal Cancer; Head and Neck Cancer, and Mesothelioma.

In one embodiment, the method of treatment of the present invention targets lymphoma, wherein the lymphoma is selected from the group consisting of: diffuse large B-cell lymphoma, AIDS-Related Lymphoma, Cutaneous T-Cell Lymphoma, Sezary syndrome, mycosis fungoides (MF); Histiocytosis; Burkitt Lymphoma, and Central Nervous System Lymphoma; Non-Hodgkin Lymphoma, and Primary Central Nervous System Lymphoma, Hodgkin Lymphoma, Waldenström's macroglobulinemia; Mycosis Fungoides; Primary Central Nervous System Lymphoma; lymphoplasmacytic lymphoma, and Primary Central Nervous System Lymphoma.

In one embodiment, the method of treatment of the present invention targets Non-Hodgkin's lymphoma (NHL), wherein the Non-Hodgkin's lymphoma is selected from the group consisting of mantle cell lymphoma, diffuse large B-cell lymphoma, follicular lymphoma, marginal zone lymphoma, small lymphocytic lymphoma, lyphoplasmacytic NHL, Waldenström's macroglobulinaemia, and skin lymphomas.

In one embodiment, the method of treatment of the present invention targets leukemia, wherein the leukemia is selected from the group consisting of: Acute Lymphoblastic Leukemia (ALL), Chronic Lymphocytic Leukemia (CLL), Chronic Myeloproliferative Disorders; Hairy Cell Leukemia; Acute Myeloid Leukemia (AML); Chronic Myelogenous Leukemia (CML); and Langerhans Cell Histiocytosis.

In one embodiment, the method of treatment of the present invention targets acute leukemia, wherein the acute leukemia is selected from the group consisting of acute lymphotyte leukemia, acute myeloid leukemia, chronic lymphoblastic leukemia, chronic myeloid leukemia, myelodysplastic syndrome, or myeloproliferative disease.

In one embodiment, the method of treatment of the present invention targets myeloma, wherein the myeloma is selected from the group consisting of: IgA myeloma; IgG myeloma; IgM myeloma; IgD myeloma; IgE myeloma; light chain myeloma; non secretory myeloma; Multiple Myeloma/Plasma Cell Neoplasm, Multiple Myeloma, Myelodysplastic Syndromes, Myelodysplastic/Myeloproliferative Neoplasms, Myeloproliferative Disorders.

In one embodiment, the method of treatment of the present invention targets cancer, wherein the cancer is selected from the group consisting of Acute Lymphoblastic Leukemia, Acute Myeloid Leukemia, Adrenocortical Carcinoma, AIDS-Related Cancers, AIDS-Related Lymphoma, Anal or Rectal Cancer, Appendix Cancer, Astrocytomas, and Atypical Teratoid/Rhabdoid Tumor.

In one embodiment, the method of treatment of the present invention targets cancer, wherein the cancer is selected from the group consisting of Basal Cell Carcinoma, Basal Cell Nevus Syndrome, Gorlin-Nevus Syndrome, Bile Duct Cancer, Bladder Cancer, Bone Cancer, Osteosarcoma and Malignant Fibrous Histiocytoma, Brain Tumor, Breast Cancer, Bronchial Tumors, Burkitt Lymphoma, and Spinal Cord Tumors.

In one embodiment, the method of treatment of the present invention targets cancer, wherein the cancer is selected from the group consisting of Carcinoid Tumor, Carcinoma of Unknown Primary, Central Nervous System Atypical Teratoid/Rhabdoid Tumor, Central Nervous System Embryonal Tumors, Central Nervous System Lymphoma, Cervical Cancer, Chordoma, Chronic Lymphocytic Leukemia, Chronic Myelogenous Leukemia, Chronic Myeloproliferative Disorders, Colon Cancer, Colorectal Cancer, Craniopharyngioma, and Cutaneous T-Cell Lymphoma (including, but not limited to Sezary syndrome and mycosis fungoides).

In one embodiment, the method of treatment of the present invention targets cancer, wherein the cancer is selected from the group consisting of Embryonal Tumors of Central Nervous System, Endometrial Cancer, Ependymoblastoma, Ependymoma, Esophageal Cancer, Ewing Sarcoma Family of Tumors, Desmoplastic Round Cell Tumor, Chondrosarcoma, Extracranial Germ Cell Tumor, Extragonadal Germ Cell Tumor, Extrahepatic Bile Duct Cancer, and Eye Cancer, including Intraocular Melanoma and Retinoblastoma.

In one embodiment, the method of treatment of the present invention targets cancer, wherein the cancer is selected from the group consisting of Gallbladder Cancer, Gastric (Stomach) Cancer, Gastrointestinal Carcinoid Tumor, Gastrointestinal Stromal Tumor (GIST), Germ Cell Tumor, Gestational Trophoblastic Tumor, and Glioma.

In one embodiment, the method of treatment of the present invention targets cancer, wherein the cancer is selected from the group consisting of Hairy Cell Leukemia, Head and Neck Cancer, Hepatocellular (Liver) Cancer, Histiocytosis, Hodgkin Lymphoma, and Hypopharyngeal Cancer.

In one embodiment, the method of treatment of the present invention targets cancer, wherein the cancer is selected from the group consisting of Kaposi Sarcoma, and Kidney (Renal Cell) Cancer.

The method of treating cancer according to claim 1, wherein the cancer is selected from the group consisting of Langerhans Cell Histiocytosis, Laryngeal Cancer, Lip and Oral Cavity Cancer, Liver Cancer, Lung Cancer, including Non-Small Cell Lung Cancer, and Small Cell Lung Cancer, Non-Hodgkin Lymphoma, and Primary Central Nervous System Lymphoma.

In one embodiment, the method of treatment of the present invention targets cancer, wherein the cancer is selected from the group consisting of Waldenström's macroglobulinemia (lymphoplasmacytic lymphoma), Malignant Fibrous Histiocytoma of Bone and Osteosarcoma, Medulloblastoma, Medulloepithelioma, Melanoma, Merkel Cell Carcinoma, Mesothelioma, Metastatic Squamous Neck Cancer with Occult Primary, Multiple Endocrine Neoplasia Syndrome, Mouth Cancer, Multiple Myeloma/Plasma Cell Neoplasm, Mycosis Fungoides, Myelodysplastic Syndromes, Myelodysplastic/Myeloproliferative Neoplasms, Multiple Myeloma, and Myeloproliferative Disorders.

In one embodiment, the method of treatment of the present invention is useful for treating cancer, wherein the cancer is selected from the group consisting of Nasal Cavity and Paranasal Sinus Cancer, Nasopharyngeal Cancer, and Neuroblastoma.

In one embodiment, the method of treatment of the present invention is useful for treating cancer, wherein the cancer is selected from the group consisting of Oral Cancer, Lip and Oral Cavity Cancer, Oropharyngeal Cancer, Osteosarcoma and Malignant Fibrous Histiocytoma of Bone, Ovarian Cancer, Ovarian Germ Cell Tumor, Ovarian Epithelial Cancer, and Ovarian Low Malignant Potential Tumor.

In one embodiment, the method of treatment of the present invention is useful for treating cancer, wherein the cancer is selected from the group consisting of Pancreatic Cancer, Papillomatosis, Paranasal Sinus and Nasal Cavity Cancer, Parathyroid Cancer, Penile Cancer, Pharyngeal Cancer, Pineal Parenchymal Tumors of Intermediate Differentiation, Pineoblastoma and Supratentorial Primitive Neuroectodermal Tumors, Pituitary Tumor, Pleuropulmonary Blastoma, Pregnancy and Breast Cancer, Primary Central Nervous System Lymphoma, and Prostate Cancer.

In one embodiment, the method of treatment of the present invention is useful for treating cancer, wherein the cancer is selected from the group consisting of Rectal Cancer, Renal Cell (Kidney) Cancer, Renal Pelvis and Ureter, Respiratory Tract Carcinoma Involving the NUT Gene on Chromosome 15, Retinoblastoma, and Rhabdomyosarcoma.

In one embodiment, the method of treatment of the present invention is useful for treating cancer, wherein the cancer is selected from the group consisting of Salivary Gland Cancer, Sarcoma, Sézary Syndrome, Skin Cancer, Skin Carcinoma, Small Intestine Cancer, Soft Tissue Sarcoma, Squamous Cell Carcinoma, Squamous Neck Cancer with Occult Primary, and Supratentorial Primitive Neuroectodermal Tumors.

In one embodiment, the method of treatment of the present invention is useful for treating cancer, wherein the cancer is selected from the group consisting of T-Cell Lymphoma, Testicular Cancer, Throat Cancer, Thymoma and Thymic Carcinoma, Thyroid Cancer, Transitional Cell Cancer of the Renal Pelvis and Ureter, and Gestational Trophoblastic Tumor.

In one embodiment, the method of treatment of the present invention is useful for treating cancer, wherein the cancer is selected from the group consisting of Carcinoma of Unknown Primary Site, Cancer of Unknown Primary Site, Unusual Cancers of Childhood, Transitional Cell Cancer Of the Renal Pelvis and Ureter, Urethral Cancer, and Uterine Sarcoma.

In one embodiment, the method of treatment of the present invention is useful for treating cancer, wherein the cancer is selected from the group consisting of Vaginal Cancer, and Vulvar Cancer.

In one embodiment, the method of treatment of the present invention is useful for treating cancer, wherein the cancer is selected from the group consisting of Wilms Tumor, and Women's Cancers.

In some embodiments, treatment of cancer comprises prevention of tumor growth in a cancer subject. In some embodiments, treatment of cancer comprises prevention of formation of cancer metastases in a cancer subject. In some embodiments, treatment of cancer comprises targeted treatment of minimal residual disease in a cancer subject known to have the minimal residual disease in a cancer or a subject at risk for having minimal residual disease.

This might be indicated after treatment of the primary tumor by surgery and/or after chemotherapy (e.g. radiotherapy) has been initiated or determined to efficacious. Disseminated tumor cells may be in their dormant state and often cannot be attacked by the chemotherapy (radiotherapy). A thus treated patient seemingly is in a healed state, which is also described as "minimal residual disease". Nevertheless, the dormant tumor cells have a potential of forming metastases if they become metastasizing cells due to a growth stimulus also after a longer dormant state.

As used herein, "minimal residual disease" denotes a small number of cancer cells that remain in a subject during treatment, or after treatment when the subject is in remission (exhibiting no symptoms or signs of the disease). The methods described herein are preferably applied to any form of the diseases listed herein, including adult and childhood forms of these diseases.

In one embodiment, the method of treatment of the present invention is useful for treating an autoimmune disease. Autoimmune diseases include, but are not limited to alopecia areata, antiphospholipid, autoimmune hepatitis, celiac disease, diabetes type 1, Graves' disease, Guillain-Barre syndrome, Hashimoto's disease, hemolytic anemia, idiopathic thrombocytopenic purpura, inflammatory bowel disease, inflammatory myopathies, multiple sclerosis, primary biliary cirrhosis, psoriasis, rheumatoid arthritis, scleroderma, Sjögren's syndrome, systemic lupus erythematosus, and vitiligo.

In one embodiment, the method of treatment of the present invention is useful for treating autoimmune and inflammatory disorders of the peripheral nerve system such as amyotrophic lateral sclerosis (Lou Gehrig's disease), based on various causes such as metabolic disorders that include diabetes, B12 and folate vitamin deficiencies, chemotherapy medications and medicines used to treat HIV, poisons that cause peripheral nerve damage, cancers that develop peripheral neuropathies as well as paraneoplastic syndromes, alcohol abuse, chronic kidney disease, injuries that cause compression on nerves and other lesions, infections such as Lyme disease, Guillain Barre syndrome, connective tissue disease, rheumatoid arthritis, Sjogren's syndrome, systemic lupus erythematosus, certain inflammatory conditions such as sarcoidosis, coeliac disease, hereditary diseases such as charcot marie tooth syndrome, Friedreich's ataxia, and/or idiopathic where no specific cause is found but the inflammatory and/or autoimmune mechanisms are the cause of the onset.

In one embodiment, the method of treatment of the present invention is useful for treating autoimmune and inflammatory disorders with ocular manifestations. Such ocular manifestations include, but are not limited to, ocular cicatricial pemphigoid, Mooren's corneal ulcer, various forms of uveitis, rheumatoid arthritis, systemic lupus erythematosus, polyarteritis nodosa, relapsing polychondritis, Wegener's granulomatosis, scleroderma, Behcet's disease, Reiter's disease, inflammatory bowel disease (ulcerative colitis and Crohn's disease) and ankylosing spondylitis, retinitis pigmentosa, macular degeneration, keratoconjunctivitis sicca, scleritis, episcleritis, keratitis, peripheral corneal ulceration, and less common entities such as choroiditis, retinal vasculitis, episcleral nodules, retinal detachments, and/or macular edema.

In one embodiment, the method of treatment of the present invention is useful for treating acute allograft rejection in transplant patients. In one embodiment, the method of treatment of the present invention is useful for treating ischemic stroke. In one embodiment, the method of treatment of the present invention is useful for treating inflammatory diseases. Inflammatory diseases include, but are not limited to, arthritis, psoriasis, asthma, and colitis.

In one embodiment, the first therapeutic agent includes a pharmaceutically acceptable mono-salt of the compound (1). In one embodiment, the first therapeutic agent includes a pharmaceutically acceptable di-salt of compound (1). As described herein, some of our analogues can be tri-salts In one embodiment, the first therapeutic agent includes compound (1) in the form of a pharmaceutically acceptable mono- or di-salt selected from the group consisting of hydrochloride, hydrobromide, hydrogensulphate, sulfates, phosphates, fumarates, succinates, oxalates and lactates, bisulfates, hydroxyl, tartrate, nitrate, citrate, bitartrate, carbonate, malate, maleate, fumarate sulfonate, methylsulfonate, formate, and carboxylate. In one embodiment, the first therapeutic agent includes compound (1) in the form of a pharmaceutically acceptable mono- or di-salt selected from p-toluene-sulfonate, benzenesulfonate, methanesulfonate, oxalate, succinate, tartrate, citrate, fumarate and maleate. In one embodiment, the first therapeutic agent includes compound (1) in the form of a pharmaceutically acceptable mono- or di-salt having a counter ion selected from the group consisting of ammonium, sodium, potassium, calcium, magnesium, zinc, lithium, and/or with counter-ions such as methylamino, dimethylamino, diethylamino, triethylamino counter-ions, and combinations thereof. In one embodiment, the first therapeutic agent includes compound (1) n the form of a hydrochloride di-salt (i.e., di-hydrochloride salt) or hydrobromide di-salt.

In some embodiments of the method of treatment, the second therapeutic agent includes an anti-cancer agent. In some embodiments of the method of treatment, the second therapeutic agent is selected, without limitation, from acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bevacizumab, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflomithine, elsamitrucin, enloplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, zorubicin and combinations thereof.

In some embodiments of the method of treatment, the second therapeutic agent is selected, without limitation, from hormone analogues and antihormones, aromatase inhibitors, LHRH agonists and antagonists, inhibitors of growth factors, growth factor antibodies, growth factor receptor antibodies, tyrosine kinase inhibitors; antimetabolites; antitumour antibiotics; platinum derivatives; alkylation agents; antimitotic agents; tubuline inhibitors; PARP inhibitors, topoisomerase inhibitors, serine/threonine kinase inhibitors, tyrosine kinase inhibitors, protein protein interaction inhibitors, MEK inhibitors, ERK inhibitors, IGF-1R inhibitors, ErbB receptor inhibitors, rapamycin analogs, amifostin, anagrelid, clodronat, filgrastin, interferon, interferon alpha, leucovorin, rituximab, procarbazine, levamisole, mesna, mitotane, pamidronate and porfimer, 2-chlorodesoxyadenosine, 2-fluorodesoxy-cytidine, 2-methoxyoestradiol, 2C4,3-alethine, 131-1-TM-601, 3CPA, 7-ethyl-10-hydroxycamptothecin, 16-aza-epothilone B, A 105972, A 204197, abiraterone, aldesleukin, alitretinoin, allovectin-7, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, AMG-479 (ganitumab), ARRY 162, ARRY 438162, ARRY-300, ARRY-142886/AZD-6244 (selumetinib), ARRY-704/AZD-8330, AR-12, AR-42, AS-703988, AXL-1717, AZD-8055, AZD-5363, AZD-6244, ARQ-736, ARQ 680, AS-703026 (primasertib), avastin, AZD-2014, azacytidine, azaepothilone B, azonafide, BAY-43-9006, BAY 80-6946, BBR-3464, BBR-3576, bevacizumab, BEZ-235, biricodar dicitrate, BCX-1777, BKM-120, bleocin, BLP-25, BMS-184476, BMS-247550, BMS-188797, BMS-275291, BMS-663513, BMS-754807, BNP-1350, BNP-7787, BIBW 2992 (afatinib, tomtovok), BIBF 1120 (vargatef), BI 836845, BI 2536, BI 6727, BI 836845, BI 847325, BI 853520, BUB-022, bleomycinic acid, bleomycin A, bleomycin B, brivanib, bryostatin-1, bortezomib, brostallicin, busulphan, BYL-719, CA-4 prodrug, CA-4, CapCell, calcitriol, canertinib, canfosfamide, capecitabine, carboxyphthalatoplatin, CC1-779, CC-115, CC-223, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, CKI-27, clofarabin, colchicin, combretastatin A4, COT inhibitors, CHS-828, CH-5132799, CLL-Thera, CMT-3 cryptophycin 52, CTP-37, CTLA-4 monoclonal antibodies, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, DS-7423, E7010, E-6201, edatrexat, edotreotide, efaproxiral, eflornithine, EGFR inhibitors, EKB-569, EKB-509, enzastaurin, enzalutamide, elsamitrucin, epothilone B, epratuzumab, ER-86526, erlotinib, ET-18-0CH3, ethynylcytidine, ethynyloestradiol, exatecan, exatecan mesylate, exemestane, exisulind, fenretinide, figitumumab, floxuridine, folic acid, FOLFOX, FOLFOX4, FOLFIRI, formestane, fotemustine, galarubicin, gallium maltolate, gefinitib, gemtuzumab, gimatecan, glufosfamide, GCS-100, GDC-0623, GDC-0941 (pictrelisib), GDC-0980, GDC-0032, GDC-0068, GDC-0349, GDC-0879, G17DT immunogen, GMK, GPX-100, gp100-peptide vaccines, GSK-5126766, GSK-690693, GSK-1120212 (trametinib), GSK-2118436 (dabrafenib), GSK-2126458, GSK-2132231A, GSK-2334470, GSK-2110183, GSK-2141795, GW2016, granisetron, herceptine, hexamethylmelamine, histamine, homoharringtonine, hyaluronic acid, hydroxyurea, hydroxyprogesterone caproate, ibandronate, ibritumomab, idatrexate, idenestrol, IDN-5109, IGF-1R inhibitors, IMC-1C11, IMC-A12 (cixutumumab), immunol, indisulam, interferon alpha-2a, interferon alpha-2b, pegylated interferon alpha-2b, interleukin-2, INK-1117, INK-128, INSM-18, ionafarnib, ipilimumab, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, KW-2450, lobaplatin, leflunomide, lenograstim, leuprolide, leuporelin, lexidronam, LGD-1550, linezolid, lutetium texaphyrin, lometrexol, losoxantrone, LU 223651, lurtotecan, LY-S6AKT1, LY-2780301, mafosfamide, marimastat, mechloroethamine, MEK inhibitors, MEK-162, methyltestosteron, methylprednisolone, MEDI-573, MEN-10755, MDX-H210, MDX-447, MDX-1379, MGV, midostaurin, minodronic acid, mitomycin, mivobulin, MK-2206, MK-0646 (dalotuzumab), MLN518, motexafin gadolinium, MS-209, MS-275, MX6, neridronate, neratinib, Nexavar, neovastat, nilotinib, nimesulide, nitroglycerin, nolatrexed, norelin, N-acetylcysteine, 06-benzylguanine, oblimersen, omeprazole, oncophage, oncoVEXGM-CSF, ormiplatin, ortataxel, OX44 antibodies, OSI-027, OSI-906 (linsitinib), 4-1BB antibodies, oxantrazole, oestrogen, panitumumab, patupilone, pegfilgrastim, PCK-3145, pegfilgrastim, PBI-1402, PBI-05204, PD0325901, PD-1 antibodies, PEG-paclitaxel, albumin-stabilized paclitaxel, PEP-005, PF-05197281, PF-05212384, PF-04691502, PHT-427, P-04, PKC412, P54, PI-88, pelitinib, pemetrexed, pentrix, perifosine, perillylalcohol, pertuzumab, PI3K inhibitors, PI3K/mTOR inhibitors, PG-TXL, PG2, PLX-4032/RO-5185426 (vemurafenib), PLX-3603/RO-5212054, PT-100, PWT-33597, PX-866, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, R115777, RAF-265, ramosetron, ranpirnase, RDEA-119/BAY 869766, RDEA-436, rebeccamycin analogues, receptor tyrosine kinase (RTK) inhibitors, revimid, RG-7167, RG-7304, RG-7421, RG-7321, RG 7440, rhizoxin, rhu-MAb, rinfabate, risedronate, rituximab, robatumumab, rofecoxib, RO-31-7453, RO-5126766, RO-5068760, RPR 109881A, rubidazone, rubitecan, R-flurbiprofen, RX-0201, S-9788, sabarubicin, SAHA, sargramostim, satraplatin, SB 408075, Se-015/Ve-015, SU5416, SU6668, SDX-101, semustin, seocalcitol, SM-11355, SN-38, SN-4071, SR-27897, SR-31747, SR-13668, SRL-172, sorafenib, spiroplatin, squalamine, suberanilohydroxamic acid, sutent, T 900607, T 138067, TAK-733, TAS-103, tacedinaline, talaporf in, Tarceva, tariquitar, tasisulam, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymalfasin, thymectacin, tiazofurin, tipifarnib, tirapazamine, tocladesine, tomudex, toremofin, trabectedin, TransMID-107, transretinic acid, traszutumab, tremelimumab, tretinoin, triacetyluridine, triapine, triciribine, trimetrexate, TLK-286TXD 258, tykerb/tyverb, urocidin, valrubicin, vatalanib, vincristine, vinflunine, virulizin, WX-UK1, WX-554, vectibix, xeloda, XELOX, XL-147, XL-228, XL-281, XL-518/R-7420/GDC-0973, XL-765, YM-511, YM-598, ZD-4190, ZD-6474, ZD-4054, ZD-0473, ZD-6126, ZD-9331, ZD1839, ZSTK-474, zoledronat, zosuquidar, and combinations thereof.

In some embodiments of the method of treatment, the second therapeutic agent is selected from the group consisting of tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxy-progesterone, octreotide, and combinations thereof. In some embodiments of the method of treatment, the second therapeutic agent is selected, without limitation, from the group consisting of LHRH agonists and LHRH antagonists. In some embodiments of the method of treatment, the second therapeutic agent includes a LHRH agonist selected from the group consisting of goserelin acetate, luprolide acetate, triptorelin pamoate and combinations thereof. In some embodiments of the method of treatment, the second therapeutic agent includes a LHRH antagonist selected from the group consisting of wherein the LHRH antagonists are selected from the group consisting of Degarelix, Cetrorelix, Abarelix, Ozarelix, Degarelix combinations thereof. In some embodiments of the method of treatment, the second therapeutic agent includes an inhibitor of a growth factor. In some embodiments of the method of treatment, of the second therapeutic agent, the inhibitor of the growth factor is selected, without limitation, from the group consisting of inhibitors of: platelet derived growth factor (PDGF), fibroblast growth factor (FGF), vascular endothelial growth factor (VEGF), epidermal growth factor (EGF), insuline-like growth factors (IGF), human epidermal growth factor (HER), hepatocyte growth factor (HGF), and combinations thereof. In some embodiments of the method of treatment, the second therapeutic agent includes In some embodiments of the method of treatment, the second therapeutic agent includes an inhibitor of a growth factor. In some embodiments of the method of treatment, the second therapeutic agent includes an inhibitor of the human epidermal growth factor (HER). In some embodiments of the method of treatment, the second therapeutic agent includes an inhibitor of a growth factor selected from the group consisting of: platelet derived growth factor (PDGF), fibroblast growth factor (FGF), vascular endothelial growth factor (VEGF), epidermal growth factor (EGF), insulin-like growth factors (IGF), human epidermal growth factor (HER) and hepatocyte growth factor (HGF). In some embodiments of the method of treatment, the second therapeutic agent includes n inhibitor of the human epidermal growth factor (HER). In some embodiments of the method of treatment, the second therapeutic agent includes an inhibitor of the human epidermal growth factor (HER) selected from the group consisting of HER2, HER3, and HER4. In some embodiments of the method of treatment, the second therapeutic agent includes a tyrosine kinase inhibitor. In some embodiments of the method of treatment, the second therapeutic agent includes a tyrosine kinase inhibitor selected, without limitation, from the group consisting of cetuximab, gefitinib, imatinib, lapatinib and trastuzumab, and combinations thereof. In some embodiments of the method of treatment, the second therapeutic agent includes an aromatase inhibitor. In some embodiments of the method of treatment, the second therapeutic agent includes an aromatase inhibitor selected from the group consisting of anastrozole, letrozole, liarozole, vorozole, exemestane, atamestane, and combinations thereof.

In some embodiments of the method of treatment, the second therapeutic agent includes an antimetabolite. In some embodiments of the method of treatment, the second therapeutic agent includes an antimetabolite that comprises an antifolate. In some embodiments of the method of treatment, the second therapeutic agent includes an antifolate selected from the group consisting of methotrexate, raltitrexed, pyrimidine analogues, and combinations thereof. In some embodiments of the method of treatment, the second therapeutic agent includes an antimetabolite that is pyrimidine analogue. In some embodiments of the method of treatment, the second therapeutic agent includes a pyrimidine analogue selected from the group consisting of 5-fluorouracil, capecitabin, gemcitabin, and combination thereof. In some embodiments of the method of treatment, the second therapeutic agent includes an antimetabolite that is a purine analogue or adenosine analogue. In some embodiments of the method of treatment, the second therapeutic agent includes a purine analogue or adenosine analogue selected from the group consisting of mercaptopurine, thioguanine, cladribine and pentostatin, cytarabine, fludarabine, and combinations thereof. In some embodiments of the method of treatment, the second therapeutic agent includes an antitumour antibiotic. In some embodiments of the method of treatment, the antitumor antibiotic is selected from the group consisting of anthracyclins, doxorubicin, daunorubicin, epirubicin and idarubicin, mitomycin-C, bleomycin, dactinomycin, plicamycin, streptozocin and combinations thereof. In some embodiments of the method of treatment, the second therapeutic agent includes a platinum derivative. In some embodiments of the method of treatment, the platinum derivative is selected from the group consisting of cisplatin, oxaliplatin, carboplatin and combinations thereof. In some embodiments of the method of treatment, the second therapeutic agent includes an alkylation agent. In some embodiments of the method of treatment, the second therapeutic agent includes an alkylation agent selected from the group consisting of estramustin, meclorethamine, melphalan, chlorambucil, busulphan, dacarbazin, cyclophosphamide, ifosfamide, temozolomide, nitrosoureas, and combinations thereof. In some embodiments of the method of treatment, the second therapeutic agent includes a nitrosourea. In some embodiments of the method of treatment, the second therapeutic agent includes a nitrosourea selected from the group consisting of carmustin, lomustin, thiotepa, and combinations thereof. In some embodiments of the method of treatment, the second therapeutic agent includes an antimitotic agent. In some embodiments of the method of treatment, the second therapeutic agent includes an antimitotic agent selected from the group consisting of *Vinca* alkaloids and taxanes. In some embodiments of the method of treatment, the second therapeutic agent includes a taxane selected from the group consisting of paclitaxel, docetaxel, and combinations thereof. In some embodiments of the method of treatment, the second therapeutic agent includes a *Vinca* alkaloids are selected from the group consisting of vinblastine, vindesin, vinorelbin, vincristine, and combinations thereof. In some embodiments of the method of treatment, the second therapeutic agent includes a topoisomerase inhibitor. In some embodiments of the method of treatment, the second therapeutic agent includes a topoisomerase inhibitor which is an epipodophyllotoxin. In some embodiments of the method of treatment, the second therapeutic agent includes a topoisomerase inhibitor, which is a epipodophyllotoxins selected from the group consisting of etoposide and etopophos, teniposide, amsacrin, topotecan, irinotecan, mitoxantron, and combinations thereof. In some embodiments of the method of treatment, the second therapeutic agent includes a serine/threonine kinase inhibitor. In some embodiments of the method of treatment, the second therapeutic agent includes a serine/threonine kinase inhibitor selected from the group consisting of PDK 1 inhibitors, B-Raf inhibitors, mTOR inhibitors, mTORC1 inhibitors, PI3K inhibitors, dual mTOR/PI3K inhibitors, STK 33 inhibitors, AKT inhibitors, PLK 1 inhibitors, inhibitors of CDKs, Aurora kinase inhibitors, and combinations thereof. In some embodiments of the method of treatment, the second therapeutic agent includes a tyrosine kinase inhibitor. In some embodiments of the method of treatment, the second therapeutic agent includes a PTK2/FAK inhibitor. In some embodiments of the method of treatment, the second therapeutic agent includes a protein protein interaction inhibitor. In some embodiments of the method of treatment, the second therapeutic agent includes a protein protein interaction inhibitor selected from the group consisting of IAP, Mcl-1, MDM2/MDMX and combinations thereof. In some embodiments of the method of treatment, the second therapeutic agent includes a rapamycin analog. In some embodiments of the method of treatment, the second therapeutic agent includes a rapamycin analog selected from the group consisting of everolimus, temsirolimus, ridaforolimus, sirolimus, and combinations thereof. In some embodiments of the method of treatment, the second therapeutic agent is selected from the group consisting of amifostin, anagrelid, clodronat, filgrastin, interferon, interferon alpha, leucovorin, rituximab, procarbazine, levamisole, mesna, mitotane, pamidronate and porfimer, and combinations thereof. In some embodiments of the method of treatment, the second therapeutic agent is selected from the group consisting of 2-chlorodesoxyadenosine, 2-fluorodesoxy-cytidine, 2-methoxyoestradiol, 2C4,3-alethine, 131-1-TM-601, 3CPA, 7-ethyl-10-hydroxycamptothecin, 16-aza-epothilone B, A 105972, A 204197, abiraterone, aldesleukin, alitretinoin, allovectin-7, altretamine, alvocidib, amonafide, anthrapyrazole, AG-2037, AP-5280, apaziquone, apomine, aranose, arglabin, arzoxifene, atamestane, atrasentan, auristatin PE, AVLB, AZ10992, ABX-EGF, AMG-479 (ganitumab), ARRY 162, ARRY 438162, ARRY-300, ARRY-142886/AZD-6244 (selumetinib), ARRY-704/AZD-8330, AR-12, AR-42, AS-703988, AXL-1717, AZD-8055, AZD-5363, AZD-6244, ARQ-736, ARQ 680, AS-703026 (primasertib), avastin, AZD-2014, azacytidine, azaepothilone B, azonafide, BAY-43-9006, BAY 80-6946, BBR-3464, BBR-3576, bevacizumab, BEZ-235, biricodar dicitrate, BCX-1777, BKM-120, bleocin, BLP-25, BMS-184476, BMS-247550, BMS-188797, BMS-275291, BMS-663513, BMS-754807, BNP-1350, BNP-7787, BIBW 2992 (afatinib, tomtovok), BIBF 1120 (vargatef), BI 836845, BI 2536, BI 6727, BI 836845, BI 847325, BI 853520, BUB-022, bleomycinic acid, bleomycin A, bleomycin B, brivanib, bryostatin-1, bortezomib, brostallicin, busulphan, BYL-719, CA-4 prodrug, CA-4, CapCell, calcitriol, canertinib, canfosfamide, capecitabine, carboxyphthalatoplatin, CC1-779, CC-115, CC-223, CEP-701, CEP-751, CBT-1 cefixime, ceflatonin, ceftriaxone, celecoxib, celmoleukin, cemadotin, CH4987655/RO-4987655, chlorotrianisene, cilengitide, ciclosporin, CDA-II, CDC-394, CKD-602, CKI-27, clofarabin, colchicin, combretastatin A4, COT inhibitors, CHS-828, CH-5132799, CLL-Thera, CMT-3 cryptophycin 52, CTP-37, CTLA-4 monoclonal antibodies, CP-461, CV-247, cyanomorpholinodoxorubicin, cytarabine, D 24851, decitabine, deoxorubicin, deoxyrubicin, deoxycoformycin, depsipeptide, desoxyepothilone B, dexamethasone, dexrazoxanet, diethylstilbestrol, diflomotecan, didox, DMDC, dolastatin 10, doranidazole, DS-7423, E7010, E-6201, edatrexat, edotreotide, efaproxiral, eflornithine, EGFR inhibitors, EKB-569, EKB-509, enzastaurin, enzalutamide, elsamitrucin, epothilone B, epratuzumab, ER-86526, erlotinib, ET-18-0CH3, ethynylcytidine, ethynyloestradiol, exatecan, exatecan mesylate, exemestane, exisulind, fenretinide, figitumumab, floxuridine, folic acid, FOLFOX, FOLFOX4, FOLFIRI, formestane, fotemustine, galarubicin, gallium maltolate, gefinitib, gemtuzumab, gimatecan, glufosfamide, GCS-100, GDC-0623, GDC-0941 (pictrelisib), GDC-0980, GDC-0032, GDC-0068, GDC-0349, GDC-0879, G17DT immunogen, GMK, GPX-100, gp100-peptide vaccines, GSK-5126766, GSK-690693, GSK-1120212 (trametinib), GSK-2118436 (dabrafenib), GSK-2126458, GSK-2132231A, GSK-2334470, GSK-2110183, GSK-2141795, GW2016, granisetron, herceptine, hexamethylmelamine, histamine, homoharringtonine, hyaluronic acid, hydroxyurea, hydroxyprogesterone caproate, ibandronate, ibritumomab, idatrexate, idenestrol, IDN-5109, IGF-1R inhibitors, IMC-1C11, IMC-A12 (cixutumumab), immunol, indisulam, interferon alpha-2a, interferon alpha-2b, pegylated interferon alpha-2b, interleukin-2, INK-1117, INK-128, INSM-18, ionafarnib, ipilimumab, iproplatin, irofulven, isohomohalichondrin-B, isoflavone, isotretinoin, ixabepilone, JRX-2, JSF-154, J-107088, conjugated oestrogens, kahalid F, ketoconazole, KW-2170, KW-2450, lobaplatin, leflunomide, lenograstim, leuprolide, leuporelin, lexidronam, LGD-1550, linezolid, lutetium texaphyrin, lometrexol, losoxantrone, LU 223651, lurtotecan, LY-S6AKT1, LY-2780301, mafosfamide, marimastat, mechloroethamine, MEK inhibitors, MEK-162, methyltestosteron, methylprednisolone, MEDI-573, MEN-10755, MDX-H210, MDX-447, MDX-1379, MGV, midostaurin, minodronic acid, mitomycin, mivobulin, MK-2206, MK-0646 (dalotuzumab), MLN518, motexaf in gadolinium, MS-209, MS-275, MX6, neridronate, neratinib, Nexavar, neovastat, nilotinib, nimesulide, nitroglycerin, nolatrexed, norelin, N-acetylcysteine, 06-benzylguanine, oblimersen, omeprazole, oncophage, oncoVEXGM-CSF, ormiplatin, ortataxel, OX44 antibodies, OSI-027, OSI-906 (linsitinib), 4-1BB antibodies, oxantrazole, oestrogen, panitumumab, patupilone, pegfilgrastim, PCK-3145, pegfilgrastim, PBI-1402, PBI-05204, PD0325901, PD-1 antibodies, PEG-paclitaxel, albumin-stabilized paclitaxel, PEP-005, PF-05197281, PF-05212384, PF-04691502, PHT-427, P-04, PKC412, P54, PI-88, pelitinib, pemetrexed, pentrix, perifosine, perillylalcohol, pertuzumab, PI3K inhibitors, PI3K/mTOR inhibitors, PG-TXL, PG2, PLX-4032/RO-5185426 (vemurafenib), PLX-3603/RO-5212054, PT-100, PWT-33597, PX-866, picoplatin, pivaloyloxymethylbutyrate, pixantrone, phenoxodiol O, PKI166, plevitrexed, plicamycin, polyprenic acid, porfiromycin, prednisone, prednisolone, quinamed, quinupristin, R115777, RAF-265, ramosetron, ranpirnase, RDEA-119/BAY 869766, RDEA-436, rebeccamycin analogues, receptor tyrosine kinase (RTK) inhibitors, revimid, RG-7167, RG-7304, RG-7421, RG-7321, RG 7440, rhizoxin, rhu-MAb, rinfabate, risedronate, rituximab, robatumumab, rofecoxib, RO-31-7453, RO-5126766, RO-5068760, RPR 109881A, rubidazone, rubitecan, R-flurbiprofen, RX-0201, S-9788, sabarubicin, SAHA, sargramostim, satraplatin, SB 408075, Se-015/Ve-015, SU5416, SU6668, SDX-101, semustin, seocalcitol, SM-11355, SN-38, SN-4071, SR-27897, SR-31747, SR-13668, SRL-172, sorafenib, spiroplatin, squalamine, suberanilohydroxamic acid, sutent, T 900607, T 138067, TAK-733, TAS-103, tacedinaline, talaporf in, Tarceva, tariquitar, tasisulam, taxotere, taxoprexin, tazarotene, tegafur, temozolamide, tesmilifene, testosterone, testosterone propionate, tesmilifene, tetraplatin, tetrodotoxin, tezacitabine, thalidomide, theralux, therarubicin, thymalfasin, thymectacin, tiazofurin, tipifarnib, tirapazamine, tocladesine, tomudex, toremofin, trabectedin, TransMID-107, transretinic acid, traszutumab, tremelimumab, tretinoin, triacetyluridine, triapine, triciribine, trimetrexate, TLK-286TXD 258, tykerb/tyverb, urocidin, valrubicin, vatalanib, vincristine, vinflunine, virulizin, WX-UK1, WX-554, vectibix, xeloda, XELOX, XL-147, XL-228, XL-281, XL-518/R-7420/GDC-0973, XL-765, YM-511, YM-598, ZD-4190, ZD-6474, ZD-4054, ZD-0473, ZD-6126, ZD-9331, ZD1839, ZSTK-474, zoledronat, zosuquidar, and combinations thereof.

In some embodiments, the at least one other therapeutic agent comprises a steroid. Steroids include, but are not limited to, dexamethasone, prednisolone, methyl prednisolone, prednisone, hydrocortisone, triamcinolone, betamethasone, and cortivazol. In some embodiments, the at least one other therapeutic agent comprises an anti-emetic. Antiemetics include, but are not limited to, 5-HT3 receptor agonists (such as dolasetron, granisetron, ondansetron, tropisetron, palonosetron, and mirtazapine), dopamine agonists (such as domperidone, olanzapine, droperidol, haloperidol, chlorpromazine, prochlorperazine, alizapride, prochlorperazine, and metoclopramide), NK1 receptor antagonists (such as aprepitant and casopitant), antihistamines (such as cyclizine, diphenhydramine, dimenhydrinate, doxylamine, meclizine, promethazine, hydroxyzine), cannabinoids (such as cannabis, dronabinol, nabilone, and sativex), benzodiazepines (such as midazolam and lorazepam), anticholinergics (such as hyoscine), trimethobenzamide, ginger, emetrol, propofol, peppermint, muscimol, and ajwain.

The pharmaceutical compositions of the present invention may be administered to a subject via any suitable route of administration. In one embodiment, the pharmaceutical composition is administered to a subject orally, parenterally, transdermally or transmucosally. In one embodiment, the pharmaceutical composition is administered to a subject in a parenteral dosage form. In one embodiment, the pharmaceutical composition is administered to a subject as a parenterally. In one embodiment, the pharmaceutical composition is administered to a subject via a parenteral route of administration selected from the group consisting of intravenous (IV), subcutaneous (SC), and intramuscular (IM). In one embodiment, the pharmaceutical composition is administered to a subject via a route of administration selected from rectal (PR) and transdermal. In one embodiment, the pharmaceutical composition is administered to a subject in a dosage form selected from the group consisting of sterile solutions, suspensions, suppositories, tablets and capsules. In one embodiment, the pharmaceutical composition is administered to a subject in an oral dosage form selected from the group consisting of a tablet, caplet, capsule, lozenge, syrup, liquid, suspension and elixir. In one embodiment, the pharmaceutical composition is administered to a subject in an oral dosage form selected from the group consisting of tablets, hard shell capsules, soft gelatin capsules, beads, granules, aggregates, powders, gels, solids and semi-solids.

In some embodiments, the pharmaceutical composition is in administered to a subject as a dosage form selected from the group consisting of sustained release forms, controlled release forms, delayed release forms and response release forms.

In some embodiments, the pharmaceutical composition in accordance with the present invention is administered to a subject once daily. In some embodiments, a pharmaceutical composition in accordance with the present invention is administered to a subject according to an infrequent dosing regimen (e.g., administered once per week or less frequently). In some embodiments, a pharmaceutical composition in accordance with the present invention is administered to a subject according to a frequent dosing regimen (e.g., administered more than once per week). In some embodiments, the pharmaceutical composition in accordance with the present invention is administered to a subject once weekly. In some embodiments, the pharmaceutical composition in accordance with the present invention is administered to a subject once every four weeks. In some embodiments, the pharmaceutical composition in accordance with the present invention is administered to a subject twice a week. In some embodiments, the pharmaceutical composition in accordance with the present invention is administered to a subject once every two weeks. In some embodiments, the pharmaceutical composition in accordance with the present invention is administered to a subject once every three weeks. In some embodiments, the pharmaceutical composition in accordance with the present invention is administered to a subject in a repeated cycle of once weekly, once every two weeks, once every three weeks, once every four weeks or combinations thereof.

In one embodiment, the method of treatment comprises administering to a subject in need of such treatment: (i) a first therapeutic agent including a compound comprising compound (1) or a pharmaceutically acceptable salt thereof in combination with (ii) a second therapeutic agent, wherein the first therapeutic agent and the second therapeutic agent are administered either simultaneously or sequentially; and further comprises assaying the expression of an endoplasmic reticulum (ER) stress response genes in a biological sample. In some embodiments the endoplasmic reticulum stress response gene is selected from the group that includes, but is not limited to, C/EBP-Homologous Protein (CHOP), Activating Transcription Factor 3 (ATF3) and both CHOP and ATF3. The biological sample may be tumor, peripheral blood mononuclear cells, or skin biopsy. The biological sample may be obtained before, during, or after drug administration. In some embodiments, the method of treatment further comprises adjusting a dose of compound (1) to achieve induction of about 50%, 75%, 100%, 125%, 150%, 175%, 200%, 225%, 250%, 275%, 300%, 325%, 350%, 375%, 400%, 425%, 450%, 475%, 500%, 525%, 550%, 575%, 600%, or greater than 600% of one or more ER stress gene(s). In some embodiments, the method of treatment further comprises adjusting a dose of compound (1) to achieve induction of about 50% to about 100%, about 100% to about 150%, about 150% to about 200%, about 200% to about 250%, about 250% to about 300%, about 300% to about 350%, about 350% to about 400%, about 400% to about 450%, about 450% to about 500%, about 500% to about 550%, about 550% to about 600%, or greater than 600% of the ER stress gene. In some embodiments, the method of treatment further comprises adjusting a dose of compound (1) to achieve induction of about 50% to about 100%, about 100% to about 200%, about 200% to about 300%, about 300% to about 400%, about 400% to about 500%, about 500% to about 600%, or greater than 600% of the ER stress gene.

In one embodiment, the method of treatment comprises administering to a subject in need of such treatment: (i) a first therapeutic agent including a compound comprising compound (1) or a pharmaceutically acceptable salt thereof in combination with (ii) a second therapeutic agent, wherein the first therapeutic agent and the second therapeutic agent are administered either simultaneously or sequentially; and further comprises assaying the expression of a proteasomal activity in a biological sample. In some embodiments the proteasomal activity may be chymotrysin-like, trypsin-like, and/or caspase-like activity. In some embodiments the biological sample may be tumor, peripheral blood mononuclear cells, or skin cells. The biological sample may be obtained before, during, or after drug administration. In some embodiments, the method of treatment further comprises adjusting the dose to achieve inhibition of about 20%, about 25%, about 30%, about 35%, about 40%, about 45%, about 50%, about 55%, about 60%, about 65%, about 70%, about 75%, about 80%, about 85%, about 90%, about 95%, or about 100% of the proteasomal activity. In some embodiments, the method of treatment further comprises adjusting the dose to achieve inhibition of at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% of the proteasomal activity. In some embodiments, the method of treatment further comprises adjusting the dose to achieve inhibition of about 20% to about 30%, about 30% to about 40%, about 40% to about 50%, about 50% to about 60%, about 60% to about 70%, about 70% to about 80%, about 80% to about 90%, or greater than 90% of the proteasomal activity.

In an aspect, the present invention provides a method of treatment, which comprises administering to a subject in need of such treatment a combination of a first therapeutic agent including the following compound (1) and a second therapeutic agent, the method comprising:
(i) administering to the subject the first therapeutic agent including compound (1):

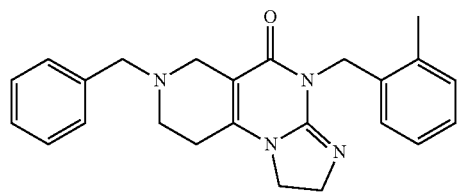

compound (1)

or a pharmaceutically acceptable salt (e.g., a di-salt or tri-salt) thereof;
(ii) waiting until a predetermined waiting time has elapsed after the time of administration of the first therapeutic agent to the subject; and/or until adverse events are resolved or resolving; and (iii) administering the second therapeutic agent to the subject, wherein the predetermined waiting time is chosen so as to obtain a delayed therapeutic effect of the first therapeutic agent without an increased risk of possible combined toxic effects of the first and second therapeutic agents. In some embodiments of the method of treatment, the predetermined waiting time is determined based on the clearance rate of compound (1) or the pharmaceutically acceptable salt thereof. In some embodiments of the method of treatment, the predetermined waiting time is determined by a quantitative assessment of renal function and parameters of renal. In some embodiments of the method of treatment, the predetermined waiting time is determined by an assays for the determination of renal function, wherein the assay is selected from the group consisting of serum level of compound (1) or the pharmaceutically acceptable salt thereof; compound (1) or the pharmaceutically acceptable salt thereof clearance rate; 24-hour urinary clearance of compound (1) or the pharmaceutically acceptable salt thereof or a metabolite thereof.

In one embodiment of the method of treatment, the predetermined waiting time substantially equals to the time required for systemic clearance of compound (1) or a pharmaceutically acceptable salt thereof from the body of the subject. In one embodiment of the method of treatment, the predetermined waiting time substantially equals to the time required for renal clearance of compound (1) or a pharmaceutically acceptable salt thereof from the body of the subject. In one embodiment of the method of treatment, the predetermined waiting time substantially equals to the time required for hepatic clearance of compound (1) or a pharmaceutically acceptable salt thereof from the body of the subject. In one embodiment of the method of treatment, the predetermined waiting time substantially equals to the time required for total clearance of compound (1) or a pharmaceutically acceptable salt thereof from the body of the subject. In one embodiment of the method of treatment, the predetermined waiting time is about 4 hours. In other embodiments the waiting time is 1 day. In some embodiments, the wait time is until Cmax of compound (1) has passed. In other embodiments, the waiting time is after most of the adverse events are resolved or are resolving. In one embodiment of the method of treatment, the predetermined waiting time is about 2 days. In one embodiment of the method of treatment, the predetermined waiting time is about 3 days. In one embodiment of the method of treatment, the predetermined waiting time is about 4 days. In one embodiment of the method of treatment, the predetermined waiting time is about 5 days. In one embodiment of the method of treatment, the predetermined waiting time is about 6 days. In one embodiment of the method of treatment, the predetermined waiting time is about 7 days. In one embodiment of the method of treatment, the predetermined waiting time is about 1-7 days. In one embodiment of the method of treatment, the predetermined waiting time is about 1-6 days. In one embodiment of the method of treatment, the predetermined waiting time is about 1-5 days. In one embodiment of the method of treatment, the predetermined waiting time is about 1-4 days. In one embodiment of the method of treatment, the predetermined waiting time is about 1-3 days. In one embodiment of the method of treatment, the predetermined waiting time is about 1 to 2 days. In some embodiments, the waiting time is up to 3 weeks. The preceeding are considered "therapeutic time periods."

When the order of administration is reversed, timing for the administration of compound (1) can be after the Cmax of the first administered drug has passed. In some embodiments, administration of compound (1) can be after most or substantially all of the first administered drug has been eliminated from the body or the toxicity effects for the first administered drug are resolved or are resolving.

In some embodiments, the method of treatment further comprises monitoring level of compound (1), a pharmaceutically acceptable salt thereof, or a metabolite thereof in the subject using pharmacokinetic profiling. In some such embodiments, monitoring level of compound (1), a pharmaceutically acceptable salt thereof, or a metabolite thereof in the subject using pharmacokinetic profiling comprises constructing a pharmacokinetic profile of compound (1), a pharmaceutically acceptable salt thereof, or a metabolite thereof for the subject using concentrations of compound (1), a pharmaceutically acceptable salt thereof, or a metabolite thereof in at least two samples obtained from the subject at time points suitable to construct a pharmacokinetic profile. In some embodiments of the method, which include monitoring level of compound (1), a pharmaceutically acceptable salt thereof, or a metabolite thereof in the subject using pharmacokinetic profiling, at least two samples are collected from the subject at point-of-care or point of use by sampling or self-sampling on point-of-care devices or point of use devices or on matrices suitable for storage of the at least two samples prior to quantitation in a laboratory. In some embodiments of the method of treatment, each of the point-of-care devices or point of use devices is capable of quantitating compound (1), a pharmaceutically acceptable salt thereof, or a metabolite. In some embodiments of the method, which include monitoring level of compound (1), a pharmaceutically acceptable salt thereof, or a metabolite thereof in the subject, one or more samples are collected from the subject at point-of-care or point of use by biopsy device for analysis at the point-of-care or point of use devices or for storage prior to analysis by a laboratory. In some embodiments of the method, a biopsy is taken after a time interval of 3-8 hours following administration of compound (1), a pharmaceutically acceptable salt thereof, or a metabolite thereof to the subject. In some embodiments of the method, a biopsy is taken after a time interval of 3-24 hours following administration of compound (1), a pharmaceutically acceptable salt thereof, or a metabolite thereof to the subject. In some embodiments of the method, a biopsy is taken after a time interval of 8-24 hours following administration of compound (1), a pharmaceutically acceptable salt thereof, or a metabolite thereof to the subject. In some embodiments of the method, a biopsy is taken after a time interval of 2 days following administration of compound (1), a pharmaceutically acceptable salt thereof, or a metabolite thereof to the subject. In some embodiments of the method, a biopsy is taken after a time interval of 3 days following administration of compound (1), a pharmaceutically acceptable salt thereof, or a metabolite thereof to the subject. In some embodiments of the method, a biopsy is taken after a time interval of 4 days following administration of compound (1), a pharmaceutically acceptable salt thereof, or a metabolite thereof to the subject. In some embodiments of the method, a biopsy is taken after a time interval of 1-7 days following administration of compound (1), a pharmaceutically acceptable salt thereof, or a metabolite thereof to the subject.

In some embodiments of the method of treatment, the pharmacokinetic profile includes pharmacokinetic parameters suitable for guiding dosing of compound (1) or a pharmaceutically acceptable salt thereof for the subject being treated. In some embodiments of the method of treatment, maximum concentration of the first therapeutic agent in blood (whole blood, plasma, or serum) ("Cmax") of the subject following its administration to the subject ranges from about 1000 ng/dl to 1500 ng/dl for a therapeutic time period. In some embodiments, Cmax is less than 1500 ng/dl and greater than 85 ng/dl for a therapeutic time period. In some embodiments of the method of treatment, maximum concentration of the first therapeutic agent in blood (whole blood, plasma, or serum) ("Cmax") of the subject following its administration to the subject ranges from about 1000 ng/ml to 1500 ng/ml for a therapeutic time period. In some embodiments, Cmax is less than 1500 ng/ml and greater than 85 ng/ml for a therapeutic time period.

In some embodiments, maximum concentration of the first therapeutic agent in blood (whole blood, plasma, or serum) ("Cmax") of the subject following its administration to the subject is a Cmax of from about 1000 ng/dl to about 1500 ng/dl, from about 1010 ng/dl to about 1500 ng/dl, from about 1020 ng/dl to about 1500 ng/dl, from about 1030 ng/dl to about 1500 ng/dl, from about 1040 ng/dl to about 1500 ng/dl, from about 1050 ng/dl to about 1500 ng/dl, from about 1060 ng/dl to about 1500 ng/dl, from about 1070 ng/dl to about 1500 ng/dl, from about 1080 ng/dl to about 1500 ng/dl, from about 1090 ng/dl to about 1500 ng/dl, from about 1100 ng/dl to about 1500 ng/dl, from about 1110 ng/dl to about 1500 ng/dl, from about 1120 ng/dl to about 1500 ng/dl, from about 1130 ng/dl to about 1500 ng/dl, from about 1140 ng/dl to about 1500 ng/dl, from about 1150 ng/dl to about 1500 ng/dl, from about 1160 ng/dl to about 1500 ng/dl, from about 1170 ng/dl to about 1500 ng/dl, from about 1180 ng/dl to about 1500 ng/dl, from about 1190 ng/dl to about 1500 ng/dl, from about 1200 ng/dl to about 1500 ng/dl, from about 1210 ng/dl to about 1500 ng/dl, from about 1220 ng/dl to about 1500 ng/dl, from about 1230 ng/dl to about 1500 ng/dl, from about 1240 ng/dl to about 1500 ng/dl, from about 1250 ng/dl to about 1500 ng/dl, from about 1260 ng/dl to about 1500 ng/dl, from about 1270 ng/dl to about 1500 ng/dl, from about 1280 ng/dl to about 1500 ng/dl, from about 1290 ng/dl to about 1500 ng/dl, from about 1300 ng/dl to about 1500 ng/dl, from about 1310 ng/dl to about 1500 ng/dl, from about 1320 ng/dl to about 1500 ng/dl, from about 1330 ng/dl to about 1500 ng/dl, from about 1340 ng/dl to about 1500 ng/dl, from about 1350 ng/dl to about 1500 ng/dl, from about 1360 ng/dl to about 1500 ng/dl, from about 1370 ng/dl to about 1500 ng/dl, from about 1380 ng/dl to about 1500 ng/dl, from about 1390 ng/dl to about 1500 ng/dl, from about 1400 ng/dl to about 1500 ng/dl, from about 1410 ng/dl to about 1500 ng/dl, from about 1420 ng/dl to about 1500 ng/dl, from about 1430 ng/dl to about 1500 ng/dl, from about 1440 ng/dl to about 1500 ng/dl, from about 1450 ng/dl to about 1500 ng/dl, from about 1460 ng/dl to about 1500 ng/dl, from about 1470 ng/dl to about 1500 ng/dl, from about 1480 ng/dl to about 1500 ng/dl, or from about 1490 ng/dl to about 1500 ng/dl.

In some embodiments, maximum concentration of the first therapeutic agent in blood (whole blood, plasma, or serum) ("Cmax") of the subject following its administration to the subject is a Cmax of from about 1000 ng/ml to about 1500 ng/ml, from about 1010 ng/ml to about 1500 ng/ml, from about 1020 ng/ml to about 1500 ng/ml, from about 1030 ng/ml to about 1500 ng/ml, from about 1040 ng/ml to about 1500 ng/ml, from about 1050 ng/ml to about 1500 ng/ml, from about 1060 ng/ml to about 1500 ng/ml, from about 1070 ng/ml to about 1500 ng/ml, from about 1080 ng/ml to about 1500 ng/ml, from about 1090 ng/ml to about 1500 ng/ml, from about 1100 ng/ml to about 1500 ng/ml, from about 1110 ng/ml to about 1500 ng/ml, from about 1120 ng/ml to about 1500 ng/ml, from about 1130 ng/ml to about 1500 ng/ml, from about 1140 ng/ml to about 1500 ng/ml, from about 1150 ng/ml to about 1500 ng/ml, from about 1160 ng/ml to about 1500 ng/ml, from about 1170 ng/ml to about 1500 ng/ml, from about 1180 ng/ml to about 1500 ng/ml, from about 1190 ng/ml to about 1500 ng/ml, from about 1200 ng/ml to about 1500 ng/ml, from about 1210 ng/ml to about 1500 ng/ml, from about 1220 ng/ml to about 1500 ng/ml, from about 1230 ng/ml to about 1500 ng/ml, from about 1240 ng/ml to about 1500 ng/ml, from about 1250 ng/ml to about 1500 ng/ml, from about 1260 ng/ml to about 1500 ng/ml, from about 1270 ng/ml to about 1500 ng/ml, from about 1280 ng/ml to about 1500 ng/ml, from about 1290 ng/ml to about 1500 ng/ml, from about 1300 ng/ml to about 1500 ng/ml, from about 1310 ng/ml to about 1500 ng/ml, from about 1320 ng/ml to about 1500 ng/ml, from about 1330 ng/ml to about 1500 ng/ml, from about 1340 ng/ml to about 1500 ng/ml, from about 1350 ng/ml to about 1500 ng/ml, from about 1360 ng/ml to about 1500 ng/ml, from about 1370 ng/ml to about 1500 ng/ml, from about 1380 ng/ml to about 1500 ng/ml, from about 1390 ng/ml to about 1500 ng/ml, from about 1400 ng/ml to about 1500 ng/ml, from about 1410 ng/ml to about 1500 ng/ml, from about 1420 ng/ml to about 1500 ng/ml, from about 1430 ng/ml to about 1500 ng/ml, from about 1440 ng/ml to about 1500 ng/ml, from about 1450 ng/ml to about 1500 ng/ml, from about 1460 ng/ml to about 1500 ng/ml, from about 1470 ng/ml to about 1500 ng/ml, from about 1480 ng/ml to about 1500 ng/ml, or from about 1490 ng/ml to about 1500 ng/ml.

In some embodiments, maximum concentration of the first therapeutic agent in blood (whole blood, plasma, or serum) ("Cmax") of the subject following its administration to the subject is selected from 1000 ng/dl, about 1010 ng/dl, about 1020 ng/dl, about 1030 ng/dl, about 1040 ng/dl, about 1050 ng/dl, about 1060 ng/dl, about 1070 ng/dl, about 1080 ng/dl, about 1090 ng/dl, about 1100 ng/dl, about 1110 ng/dl, about 1120 ng/dl, about 1130 ng/dl, about 1140 ng/dl, about 1150 ng/dl, about 1160 ng/dl, about 1170 ng/dl, about 1180 ng/dl, about 1190 ng/dl, about 1200 ng/dl, about 1210 ng/dl, about 1220 ng/dl, about 1230 ng/dl, about 1240 ng/dl, about 1250 ng/dl, about 1260 ng/dl, about 1270 ng/dl, about 1280 ng/dl, about 1290 ng/dl, about 1300 ng/dl, about 1310 ng/dl, about 1320 ng/dl, about 1330 ng/dl, about 1340 ng/dl, about 1350 ng/dl, about 1360 ng/dl, about 1370 ng/dl, about 1380 ng/dl, about 1390 ng/dl, about 1400 ng/dl, about 1410 ng/dl, about 1420 ng/dl, about 1430 ng/dl, about 1440 ng/dl, about 1450 ng/dl, about 1460 ng/dl, about 1470 ng/dl, about 1480 ng/dl, and about 1490 ng/dl.

In some embodiments, maximum concentration of the first therapeutic agent in blood (whole blood, plasma, or serum) ("Cmax") of the subject following its administration to the subject is selected from 1000 ng/ml, about 1010 ng/ml, about 1020 ng/ml, about 1030 ng/ml, about 1040 ng/ml, about 1050 ng/ml, about 1060 ng/ml, about 1070 ng/ml, about 1080 ng/ml, about 1090 ng/ml, about 1100 ng/ml, about 1110 ng/ml, about 1120 ng/ml, about 1130 ng/ml, about 1140 ng/ml, about 1150 ng/ml, about 1160 ng/ml, about 1170 ng/ml, about 1180 ng/ml, about 1190 ng/ml, about 1200 ng/ml, about 1210 ng/ml, about 1220 ng/ml, about 1230 ng/ml, about 1240 ng/ml, about 1250 ng/ml, about 1260 ng/ml, about 1270 ng/ml, about 1280 ng/ml, about 1290 ng/ml, about 1300 ng/ml, about 1310 ng/ml, about 1320 ng/ml, about 1330 ng/ml, about 1340 ng/ml, about 1350 ng/ml, about 1360 ng/ml, about 1370 ng/ml, about 1380 ng/ml, about 1390 ng/ml, about 1400 ng/ml, about 1410 ng/ml, about 1420 ng/ml, about 1430 ng/ml, about 1440 ng/ml, about 1450 ng/ml, about 1460 ng/ml, about 1470 ng/ml, about 1480 ng/ml, and about 1490 ng/ml.

In some embodiments, maximum concentration of the first therapeutic agent in blood (whole blood, plasma, or serum) ("Cmax") of the subject following its administration to the subject is selected from about 85 ng/dl, about 95 ng/dl, about 105 ng/dl, about 115 ng/dl, about 125 ng/dl, about 135 ng/dl, about 145 ng/dl, about 155 ng/dl, about 165 ng/dl, about 175 ng/dl, about 185 ng/dl, about 195 ng/dl, about 205 ng/dl, about 215 ng/dl, about 225 ng/dl, about 235 ng/dl, about 245 ng/dl, about 255 ng/dl, about 265 ng/dl, about 275 ng/dl, about 285 ng/dl, about 295 ng/dl, about 305 ng/dl, about 315 ng/dl, about 325 ng/dl, about 335 ng/dl, about 345 ng/dl, about 355 ng/dl, about 365 ng/dl, about 375 ng/dl, about 385 ng/dl, about 395 ng/dl, about 405 ng/dl, about 415 ng/dl, about 425 ng/dl, about 435 ng/dl, about 445 ng/dl, about 455 ng/dl, about 465 ng/dl, about 475 ng/dl, about 485 ng/dl, about 495 ng/dl, about 505 ng/dl, about 515 ng/dl, about 525 ng/dl, about 535 ng/dl, about 545 ng/dl, about 555 ng/dl, about 565 ng/dl, about 575 ng/dl, about 585 ng/dl, about 595 ng/dl, about 605 ng/dl, about 615 ng/dl, about 625 ng/dl, about 635 ng/dl, about 645 ng/dl, about 655 ng/dl, about 665 ng/dl, about 675 ng/dl, about 685 ng/dl, about 695 ng/dl, about 705 ng/dl, about 715 ng/dl, about 725 ng/dl, about 735 ng/dl, about 745 ng/dl, about 755 ng/dl, about 765 ng/dl, about 775 ng/dl, about 785 ng/dl, about 795 ng/dl, about 805 ng/dl, about 815 ng/dl, about 825 ng/dl, about 835 ng/dl, about 845 ng/dl, about 855 ng/dl, about 865 ng/dl, about 875 ng/dl, about 885 ng/dl, about 895 ng/dl, about 905 ng/dl, about 915 ng/dl, about 925 ng/dl, about 935 ng/dl, about 945 ng/dl, about 955 ng/dl, about 965 ng/dl, about 975 ng/dl, about 985 ng/dl, about 995 ng/dl, about 1005 ng/dl, about 1015 ng/dl, about 1025 ng/dl, about 1035 ng/dl, about 1045 ng/dl, about 1055 ng/dl, about 1065 ng/dl, about 1075 ng/dl, about 1085 ng/dl, about 1095 ng/dl, about 1105 ng/dl, about 1115 ng/dl, about 1125 ng/dl, about 1135 ng/dl, about 1145 ng/dl, about 1155 ng/dl, about 1165 ng/dl, about 1175 ng/dl, about 1185 ng/dl, about 1195 ng/dl, about 1205 ng/dl, about 1215 ng/dl, about 1225 ng/dl, about 1235 ng/dl, about 1245 ng/dl, about 1255 ng/dl, about 1265 ng/dl, about 1275 ng/dl, about 1285 ng/dl, about 1295 ng/dl, about 1305 ng/dl, about 1315 ng/dl, about 1325 ng/dl, about 1335 ng/dl, about 1345 ng/dl, about 1355 ng/dl, about 1365 ng/dl, about 1375 ng/dl, about 1385 ng/dl, about 1395 ng/dl, about 1405 ng/dl, about 1415 ng/dl, about 1425 ng/dl, about 1435 ng/dl, about 1445 ng/dl, about 1455 ng/dl, about 1465 ng/dl, about 1475 ng/dl, about 1485 ng/dl, about 1495 ng/dl, and about 1500 ng/dl.

In some embodiments, maximum concentration of the first therapeutic agent in blood (whole blood, plasma, or serum) ("Cmax") of the subject following its administration to the subject is selected from about 85 ng/ml, about 95 ng/ml, about 105 ng/ml, about 115 ng/ml, about 125 ng/ml, about 135 ng/ml, about 145 ng/ml, about 155 ng/ml, about 165 ng/ml, about 175 ng/ml, about 185 ng/ml, about 195 ng/ml, about 205 ng/ml, about 215 ng/ml, about 225 ng/ml, about 235 ng/ml, about 245 ng/ml, about 255 ng/ml, about 265 ng/ml, about 275 ng/ml, about 285 ng/ml, about 295 ng/ml, about 305 ng/ml, about 315 ng/ml, about 325 ng/ml, about 335 ng/ml, about 345 ng/ml, about 355 ng/ml, about 365 ng/ml, about 375 ng/ml, about 385 ng/ml, about 395 ng/ml, about 405 ng/ml, about 415 ng/ml, about 425 ng/ml, about 435 ng/ml, about 445 ng/ml, about 455 ng/ml, about 465 ng/ml, about 475 ng/ml, about 485 ng/ml, about 495 ng/ml, about 505 ng/ml, about 515 ng/ml, about 525 ng/ml, about 535 ng/ml, about 545 ng/ml, about 555 ng/ml, about 565 ng/ml, about 575 ng/ml, about 585 ng/ml, about 595 ng/ml, about 605 ng/ml, about 615 ng/ml, about 625 ng/ml, about 635 ng/ml, about 645 ng/ml, about 655 ng/ml, about 665 ng/ml, about 675 ng/ml, about 685 ng/ml, about 695 ng/ml, about 705 ng/ml, about 715 ng/ml, about 725 ng/ml, about 735 ng/ml, about 745 ng/ml, about 755 ng/ml, about 765 ng/ml, about 775 ng/ml, about 785 ng/ml, about 795 ng/ml, about 805 ng/ml, about 815 ng/ml, about 825 ng/ml, about 835 ng/ml, about 845 ng/ml, about 855 ng/ml, about 865 ng/ml, about 875 ng/ml, about 885 ng/ml, about 895 ng/ml, about 905 ng/ml, about 915 ng/ml, about 925 ng/ml, about 935 ng/ml, about 945 ng/ml, about 955 ng/ml, about 965 ng/ml, about 975 ng/ml, about 985 ng/ml, about 995 ng/ml, about 1005 ng/ml, about 1015 ng/ml, about 1025 ng/ml, about 1035 ng/ml, about 1045 ng/ml, about 1055 ng/ml, about 1065 ng/ml, about 1075 ng/ml, about 1085 ng/ml, about 1095 ng/ml, about 1105 ng/ml, about 1115 ng/ml, about 1125 ng/ml, about 1135 ng/ml, about 1145 ng/ml, about 1155 ng/ml, about 1165 ng/ml, about 1175 ng/ml, about 1185 ng/ml, about 1195 ng/ml, about 1205 ng/ml, about 1215 ng/ml, about 1225 ng/ml, about 1235 ng/ml, about 1245 ng/ml, about 1255 ng/ml, about 1265 ng/ml, about 1275 ng/ml, about 1285 ng/ml, about 1295 ng/ml, about 1305 ng/ml, about 1315 ng/ml, about 1325 ng/ml, about 1335 ng/ml, about 1345 ng/ml, about 1355 ng/ml, about 1365 ng/ml, about 1375 ng/ml, about 1385 ng/ml, about 1395 ng/ml, about 1405 ng/ml, about 1415 ng/ml, about 1425 ng/ml, about 1435 ng/ml, about 1445 ng/ml, about 1455 ng/ml, about 1465 ng/ml, about 1475 ng/ml, about 1485 ng/ml, about 1495 ng/ml, and about 1500 ng/ml.

In some embodiments of the method of treatment, the maximum concentration of the first therapeutic agent in blood (whole blood, plasma, or serum) ("Cmax") of the subject following its administration to the subject ranges from about 85 ng/dl to 1500 ng/dl. In some embodiments, maximum concentration of the first therapeutic agent in blood (whole blood, plasma, or serum) ("Cmax") of the subject following its administration to the subject is selected from about 85 ng/dl to about 1500 ng/dl, from about 95 ng/dl to about 1500 ng/dl, from about 105 ng/dl to about 1500 ng/dl, from about 115 ng/dl to about 1500 ng/dl, from about 125 ng/dl to about 1500 ng/dl, from about 135 ng/dl to about 1500 ng/dl, from about 145 ng/dl to about 1500 ng/dl, from about 155 ng/dl to about 1500 ng/dl, from about 165 ng/dl to about 1500 ng/dl, from about 175 ng/dl to about 1500 ng/dl, from about 185 ng/dl to about 1500 ng/dl, from about 195 ng/dl to about 1500 ng/dl, from about 205 ng/dl to about 1500 ng/dl, from about 215 ng/dl to about 1500 ng/dl, from about 225 ng/dl to about 1500 ng/dl, from about 235 ng/dl to about 1500 ng/dl, from about 245 ng/dl to about 1500 ng/dl, from about 255 ng/dl to about 1500 ng/dl, from about 265 ng/dl to about 1500 ng/dl, from about 275 ng/dl to about 1500 ng/dl, from about 285 ng/dl to about 1500 ng/dl, from about 295 ng/dl to about 1500 ng/dl, from about 305 ng/dl to about 1500 ng/dl, from about 315 ng/dl to about 1500 ng/dl, from about 325 ng/dl to about 1500 ng/dl, from about 335 ng/dl to about 1500 ng/dl, from about 345 ng/dl to about 1500 ng/dl, from about 355 ng/dl to about 1500 ng/dl, from about 365 ng/dl to about 1500 ng/dl, from about 375 ng/dl to about 1500 ng/dl, from about 385 ng/dl to about 1500 ng/dl, from about 395 ng/dl to about 1500 ng/dl, from about 405 ng/dl to about 1500 ng/dl, from about 415 ng/dl to about 1500 ng/dl, from about 425 ng/dl to about 1500 ng/dl, from about 435 ng/dl to about 1500 ng/dl, from about 445 ng/dl to about 1500 ng/dl, from about 455 ng/dl to about 1500 ng/dl, from about 465 ng/dl to about 1500 ng/dl, from about 475 ng/dl to about 1500 ng/dl, from about 485 ng/dl to about 1500 ng/dl, from about 495 ng/dl to about 1500 ng/dl, from about 505 ng/dl to about 1500 ng/dl, from about 515 ng/dl to about 1500 ng/dl, from about 525 ng/dl to about 1500 ng/dl, from about 535 ng/dl to about 1500 ng/dl, from about 545 ng/dl to about 1500 ng/dl, from about 555 ng/dl to about 1500 ng/dl, from about 565 ng/dl to about 1500 ng/dl, from about 575 ng/dl to about 1500 ng/dl, from about 585 ng/dl to about 1500 ng/dl, from about 595 ng/dl to about 1500 ng/dl, from about 605 ng/dl to about 1500 ng/dl, from about 615 ng/dl to about 1500 ng/dl, from about 625 ng/dl to about 1500 ng/dl, from about 635 ng/dl to about 1500 ng/dl, from about 645 ng/dl to about 1500 ng/dl, from about 655 ng/dl to about 1500 ng/dl, from about 665 ng/dl to about 1500 ng/dl, from about 675 ng/dl to about 1500 ng/dl, from about 685 ng/dl to about 1500 ng/dl, from about 695 ng/dl to about 1500 ng/dl, from about 705 ng/dl to about 1500 ng/dl, from about 715 ng/dl to about 1500 ng/dl, from about 725 ng/dl to about 1500 ng/dl, from about 735 ng/dl to about 1500 ng/dl, from about 745 ng/dl to about 1500 ng/dl, from about 755 ng/dl to about 1500 ng/dl, from about 765 ng/dl to about 1500 ng/dl, from about 775 ng/dl to about 1500 ng/dl, from about 785 ng/dl to about 1500 ng/dl, from about 795 ng/dl to about 1500 ng/dl, from about 805 ng/dl to about 1500 ng/dl, from about 815 ng/dl to about 1500 ng/dl, from about 825 ng/dl to about 1500 ng/dl, from about 835 ng/dl to about 1500 ng/dl, from about 845 ng/dl to about 1500 ng/dl, from about 855 ng/dl to about 1500 ng/dl, from about 865 ng/dl to about 1500 ng/dl, from about 875 ng/dl to about 1500 ng/dl, from about 885 ng/dl to about 1500 ng/dl, from about 895 ng/dl to about 1500 ng/dl, from about 905 ng/dl to about 1500 ng/dl, from about 915 ng/dl to about 1500 ng/dl, from about 925 ng/dl to about 1500 ng/dl, from about 935 ng/dl to about 1500 ng/dl, from about 945 ng/dl to about 1500 ng/dl, from about 955 ng/dl to about 1500 ng/dl, from about 965 ng/dl to about 1500 ng/dl, from about 975 ng/dl to about 1500 ng/dl, from about 985 ng/dl to about 1500 ng/dl, from about 995 ng/dl to about 1500 ng/dl, from about 1005 ng/dl to about 1500 ng/dl, from about 1015 ng/dl to about 1500 ng/dl, from about 1025 ng/dl to about 1500 ng/dl, from about 1035 ng/dl to about 1500 ng/dl, from about 1045 ng/dl to about 1500 ng/dl, from about 1055 ng/dl to about 1500 ng/dl, from about 1065 ng/dl to about 1500 ng/dl, from about 1075 ng/dl to about 1500 ng/dl, from about 1085 ng/dl to about 1500 ng/dl, from about 1095 ng/dl to about 1500 ng/dl, from about 1105 ng/dl to about 1500 ng/dl, from about 1115 ng/dl to about 1500 ng/dl, from about 1125 ng/dl to about 1500 ng/dl, from about 1135 ng/dl to about 1500 ng/dl, from about 1145 ng/dl to about 1500 ng/dl, from about 1155 ng/dl to about 1500 ng/dl, from about 1165 ng/dl to about 1500 ng/dl, from about 1175 ng/dl to about 1500 ng/dl, from about 1185 ng/dl to about 1500 ng/dl, from about 1195 ng/dl to about 1500 ng/dl, from about 1205 ng/dl to about 1500 ng/dl, from about 1215 ng/dl to about 1500 ng/dl, from about 1225 ng/dl to about 1500 ng/dl, from about 1235 ng/dl to about 1500 ng/dl, from about 1245 ng/dl to about 1500 ng/dl, from about 1255 ng/dl to about 1500 ng/dl, from about 1265 ng/dl to about 1500 ng/dl, from about 1275 ng/dl to about 1500 ng/dl, from about 1285 ng/dl to about 1500 ng/dl, from about 1295 ng/dl to about 1500 ng/dl, from about 1305 ng/dl to about 1500 ng/dl, from about 1315 ng/dl to about 1500 ng/dl, from about 1325 ng/dl to about 1500 ng/dl, from about 1335 ng/dl to about 1500 ng/dl, from about 1345 ng/dl to about 1500 ng/dl, from about 1355 ng/dl to about 1500 ng/dl, from about 1365 ng/dl to about 1500 ng/dl, from about 1375 ng/dl to about 1500 ng/dl, from about 1385 ng/dl to about 1500 ng/dl, from about 1395 ng/dl to about 1500 ng/dl, from about 1405 ng/dl to about 1500 ng/dl, from about 1415 ng/dl to about 1500 ng/dl, from about 1425 ng/dl to about 1500 ng/dl, from about 1435 ng/dl to about 1500 ng/dl, from about 1445 ng/dl to about 1500 ng/dl, from about 1455 ng/dl to about 1500 ng/dl, from about 1465 ng/dl to about 1500 ng/dl, from about 1475 ng/dl to about 1500 ng/dl, from about 1485 ng/dl to about 1500 ng/dl, from about 1495 ng/dl to about 1500 ng/dl, and from about 1500 ng/dl to about 1500 ng/dl.

In some embodiments of the method of treatment, the maximum concentration of the first therapeutic agent in blood (whole blood, plasma, or serum) ("Cmax") of the subject following its administration to the subject ranges from about 85 ng/ml to 1500 ng/ml. In some embodiments, maximum concentration of the first therapeutic agent in blood (whole blood, plasma, or serum) ("Cmax") of the subject following its administration to the subject is selected from about 85 ng/ml to about 1500 ng/ml, from about 95 ng/ml to about 1500 ng/ml, from about 105 ng/ml to about 1500 ng/ml, from about 115 ng/ml to about 1500 ng/ml, from about 125 ng/ml to about 1500 ng/ml, from about 135 ng/ml to about 1500 ng/ml, from about 145 ng/ml to about 1500 ng/ml, from about 155 ng/ml to about 1500 ng/ml, from about 165 ng/ml to about 1500 ng/ml, from about 175 ng/ml to about 1500 ng/ml, from about 185 ng/ml to about 1500 ng/ml, from about 195 ng/ml to about 1500 ng/ml, from about 205 ng/ml to about 1500 ng/ml, from about 215 ng/ml to about 1500 ng/ml, from about 225 ng/ml to about 1500 ng/ml, from about 235 ng/ml to about 1500 ng/ml, from about 245 ng/ml to about 1500 ng/ml, from about 255 ng/ml to about 1500 ng/ml, from about 265 ng/ml to about 1500 ng/ml, from about 275 ng/ml to about 1500 ng/ml, from about 285 ng/ml to about 1500 ng/ml, from about 295 ng/ml to about 1500 ng/ml, from about 305 ng/ml to about 1500 ng/ml, from about 315 ng/ml to about 1500 ng/ml, from about 325 ng/ml to about 1500 ng/ml, from about 335 ng/ml to about 1500 ng/ml, from about 345 ng/ml to about 1500 ng/ml, from about 355 ng/ml to about 1500 ng/ml, from about 365 ng/ml to about 1500 ng/ml, from about 375 ng/ml to about 1500 ng/ml, from about 385 ng/ml to about 1500 ng/ml, from about 395 ng/ml to about 1500 ng/ml, from about 405 ng/ml to about 1500 ng/ml, from about 415 ng/ml to about 1500 ng/ml, from about 425 ng/ml to about 1500 ng/ml, from about 435 ng/ml to about 1500 ng/ml, from about 445 ng/ml to about 1500 ng/ml, from about 455 ng/ml to about 1500 ng/ml, from about 465 ng/ml to about 1500 ng/ml, from about 475 ng/ml to about 1500 ng/ml, from about 485 ng/ml to about 1500 ng/ml, from about 495 ng/ml to about 1500 ng/ml, from about 505 ng/ml to about 1500 ng/ml, from about 515 ng/ml to about 1500 ng/ml, from about 525 ng/ml to about 1500 ng/ml, from about 535 ng/ml to about 1500 ng/ml, from about 545 ng/ml to about 1500 ng/ml, from about 555 ng/ml to about 1500 ng/ml, from about 565 ng/ml to about 1500 ng/ml, from about 575 ng/ml to about 1500 ng/ml, from about 585 ng/ml to about 1500 ng/ml, from about 595 ng/ml to about 1500 ng/ml, from about 605 ng/ml to about 1500 ng/ml, from about 615 ng/ml to about 1500 ng/ml, from about 625 ng/ml to about 1500 ng/ml, from about 635 ng/ml to about 1500 ng/ml, from about 645 ng/ml to about 1500 ng/ml, from about 655 ng/ml to about 1500 ng/ml, from about 665 ng/ml to about 1500 ng/ml, from about 675 ng/ml to about 1500 ng/ml, from about 685 ng/ml to about 1500 ng/ml, from about 695 ng/ml to about 1500 ng/ml, from about 705 ng/ml to about 1500 ng/ml, from about 715 ng/ml to about 1500 ng/ml, from about 725 ng/ml to about 1500 ng/ml, from about 735 ng/ml to about 1500 ng/ml, from about 745 ng/ml to about 1500 ng/ml, from about 755 ng/ml to about 1500 ng/ml, from about 765 ng/ml to about 1500 ng/ml, from about 775 ng/ml to about 1500 ng/ml, from about 785 ng/ml to about 1500 ng/ml, from about 795 ng/ml to about 1500 ng/ml, from about 805 ng/ml to about 1500 ng/ml, from about 815 ng/ml to about 1500 ng/ml, from about 825 ng/ml to about 1500 ng/ml, from about 835 ng/ml to about 1500 ng/ml, from about 845 ng/ml to about 1500 ng/ml, from about 855 ng/ml to about 1500 ng/ml, from about 865 ng/ml to about 1500 ng/ml, from about 875 ng/ml to about 1500 ng/ml, from about 885 ng/ml to about 1500 ng/ml, from about 895 ng/ml to about 1500 ng/ml, from about 905 ng/ml to about 1500 ng/ml, from about 915 ng/ml to about 1500 ng/ml, from about 925 ng/ml to about 1500 ng/ml, from about 935 ng/ml to about 1500 ng/ml, from about 945 ng/ml to about 1500 ng/ml, from about 955 ng/ml to about 1500 ng/ml, from about 965 ng/ml to about 1500 ng/ml, from about 975 ng/ml to about 1500 ng/ml, from about 985 ng/ml to about 1500 ng/ml, from about 995 ng/ml to about 1500 ng/ml, from about 1005 ng/ml to about 1500 ng/ml, from about 1015 ng/ml to about 1500 ng/ml, from about 1025 ng/ml to about 1500 ng/ml, from about 1035 ng/ml to about 1500 ng/ml, from about 1045 ng/ml to about 1500 ng/ml, from about 1055 ng/ml to about 1500 ng/ml, from about 1065 ng/ml to about 1500 ng/ml, from about 1075 ng/ml to about 1500 ng/ml, from about 1085 ng/ml to about 1500 ng/ml, from about 1095 ng/ml to about 1500 ng/ml, from about 1105 ng/ml to about 1500 ng/ml, from about 1115 ng/ml to about 1500 ng/ml, from about 1125 ng/ml to about 1500 ng/ml, from about 1135 ng/ml to about 1500 ng/ml, from about 1145 ng/ml to about 1500 ng/ml, from about 1155 ng/ml to about 1500 ng/ml, from about 1165 ng/ml to about 1500 ng/ml, from about 1175 ng/ml to about 1500 ng/ml, from about 1185 ng/ml to about 1500 ng/ml, from about 1195 ng/ml to about 1500 ng/ml, from about 1205 ng/ml to about 1500 ng/ml, from about 1215 ng/ml to about 1500 ng/ml, from about 1225 ng/ml to about 1500 ng/ml, from about 1235 ng/ml to about 1500 ng/ml, from about 1245 ng/ml to about 1500 ng/ml, from about 1255 ng/ml to about 1500 ng/ml, from about 1265 ng/ml to about 1500 ng/ml, from about 1275 ng/ml to about 1500 ng/ml, from about 1285 ng/ml to about 1500 ng/ml, from about 1295 ng/ml to about 1500 ng/ml, from about 1305 ng/ml to about 1500 ng/ml, from about 1315 ng/ml to about 1500 ng/ml, from about 1325 ng/ml to about 1500 ng/ml, from about 1335 ng/ml to about 1500 ng/ml, from about 1345 ng/ml to about 1500 ng/ml, from about 1355 ng/ml to about 1500 ng/ml, from about 1365 ng/ml to about 1500 ng/ml, from about 1375 ng/ml to about 1500 ng/ml, from about 1385 ng/ml to about 1500 ng/ml, from about 1395 ng/ml to about 1500 ng/ml, from about 1405 ng/ml to about 1500 ng/ml, from about 1415 ng/ml to about 1500 ng/ml, from about 1425 ng/ml to about 1500 ng/ml, from about 1435 ng/ml to about 1500 ng/ml, from about 1445 ng/ml to about 1500 ng/ml, from about 1455 ng/ml to about 1500 ng/ml, from about 1465 ng/ml to about 1500 ng/ml, from about 1475 ng/ml to about 1500 ng/ml, from about 1485 ng/ml to about 1500 ng/ml, from about 1495 ng/ml to about 1500 ng/ml, and from about 1500 ng/ml to about 1500 ng/ml.

In some embodiments of the method the total drug exposure over time, measured as the area under the curve ("AUC") of a plot of the concentration of the drug in blood (whole blood, plasma, or serum) of the subject following administration of the drug against time after administration of the drug ranges from about 150 ng hr/ml to about 8000 ng hr/ml. In some embodiments, AUC is less than 8000 ng hr/ml and is greater than or equal to 150 ng hr/ml.

In some embodiments of the method the total drug exposure over time, measured as the area under the curve ("AUC") of a plot of the concentration of the drug in blood (whole blood, plasma, or serum) of the subject following administration against time is an AUC of from about 100 ng hr/ml to about 8000 ng hr/ml, from about 150 ng hr/ml to about 8000 ng hr/ml, from about 200 ng hr/ml to about 8000 ng hr/ml, from about 400 ng hr/ml to about 8000 ng hr/ml, from about 600 ng hr/ml to about 8000 ng hr/ml, from about 800 ng hr/ml to about 8000 ng hr/ml, from about 1000 ng hr/ml to about 8000 ng hr/ml, from about 1200 ng hr/ml to about 8000 ng hr/ml, from about 1400 ng hr/ml to about 8000 ng hr/ml, from about 1600 ng hr/ml to about 8000 ng hr/ml, from about 1800 ng hr/ml to about 8000 ng hr/ml, from about 2000 ng hr/ml to about 8000 ng hr/ml, from about 2200 ng hr/ml to about 8000 ng hr/ml, from about 2400 ng hr/ml to about 8000 ng hr/ml, from about 2600 ng hr/ml to about 8000 ng hr/ml, from about 2800 ng hr/ml to about 8000 ng hr/ml, from about 3000 ng hr/ml to about 8000 ng hr/ml, from about 3200 ng hr/ml to about 8000 ng hr/ml, from about 3400 ng hr/ml to about 8000 ng hr/ml, from about 3600 ng hr/ml to about 8000 ng hr/ml, from about 3800 ng hr/ml to about 8000 ng hr/ml, from about 4000 ng hr/ml to about 8000 ng hr/ml, from about 4200 ng hr/ml to about 8000 ng hr/ml, from about 4400 ng hr/ml to about 8000 ng hr/ml, from about 4600 ng hr/ml to about 8000 ng hr/ml, from about 4800 ng hr/ml to about 8000 ng hr/ml, from about 5000 ng hr/ml to about 8000 ng hr/ml, from about 5200 ng hr/ml to about 8000 ng hr/ml, from about 5400 ng hr/ml to about 8000 ng hr/ml, from about 5600 ng hr/ml to about 8000 ng hr/ml, from about 5800 ng hr/ml to about 8000 ng hr/ml, from about 6000 ng hr/ml to about 8000 ng hr/ml, from about 6200 ng hr/ml to about 8000 ng hr/ml, from about 6400 ng hr/ml to about 8000 ng hr/ml, from about 6600 ng hr/ml to about 8000 ng hr/ml, from about 6800 ng hr/ml to about 8000 ng hr/ml, from about 7000 ng hr/ml to about 8000 ng hr/ml, from about 7200 ng hr/ml to about 8000 ng hr/ml, from about 7400 ng hr/ml to about 8000 ng hr/ml, from about 7600 ng hr/ml to about 8000 ng hr/ml, or from about 7800 ng hr/ml to about 8000 ng hr/ml.

In some embodiments of the method the total drug exposure over time, measured as the area under the curve ("AUC") of a plot of the concentration of the drug in blood (whole blood, plasma, or serum) of the subject following administration against time is an AUC of from about 100 ng hr/ml to about 8000 ng hr/ml, from about 150 ng hr/ml to about 7800 ng hr/ml, from about 150 ng hr/ml to about 7600 ng hr/ml, from about 150 ng hr/ml to about 7400 ng hr/ml, from about 150 ng hr/ml to about 7200 ng hr/ml, from about 150 ng hr/ml to about 7000 ng hr/ml, from about 150 ng hr/ml to about 6800 ng hr/ml, from about 150 ng hr/ml to about 6600 ng hr/ml, from about 150 ng hr/ml to about 6400 ng hr/ml, from about 150 ng hr/ml to about 6200 ng hr/ml, from about 150 ng hr/ml to about 6000 ng hr/ml, from about 150 ng hr/ml to about 5800 ng hr/ml, from about 150 ng hr/ml to about 5600 ng hr/ml, from about 150 ng hr/ml to about 5400 ng hr/ml, from about 150 ng hr/ml to about 5200 ng hr/ml, from about 1500 ng hr/ml to about 5000 ng hr/ml, from about 1500 ng hr/ml to about 4800 ng hr/ml, from about 150 ng hr/ml to about 4600 ng hr/ml, from about 150 ng hr/ml to about 4400 ng hr/ml, from about 150 ng hr/ml to about 4200 ng hr/ml, from about 150 ng hr/ml to about 4000 ng hr/ml, from about 150 ng hr/ml to about 3800 ng hr/ml, from about 150 ng hr/ml to about 3600 ng hr/ml, from about 150 ng hr/ml to about 3400 ng hr/ml, from about 150 ng hr/ml to about 3200 ng hr/ml, from about 150 ng hr/ml to about 3000 ng hr/ml, from about 1500 ng hr/ml to about 2800 ng hr/ml, from about 150 ng hr/ml to about 2600 ng hr/ml, from about 150 ng hr/ml to about 2400 ng hr/ml, from about 150 ng hr/ml to about 2200 ng hr/ml, from about 150 ng hr/ml to about 2000 ng hr/ml, from about 150 ng hr/ml to about 1800 ng hr/ml, from about 150 ng hr/ml to about 1600 ng hr/ml, from about 150 ng hr/ml to about 1400 ng hr/ml, from about 150 ng hr/ml to about 1200 ng hr/ml, from about 150 ng hr/ml to about 1000 ng hr/ml, from about 150 ng hr/ml to about 800 ng hr/ml, from about 150 ng hr/ml to about 600 ng hr/ml, from about 150 ng hr/ml to about 400 ng hr/ml, from about 150 ng hr/ml to about 200 ng hr/ml, or from about 100 ng hr/ml to about 200 ng hr/ml.

In some embodiments of the method the total drug exposure over time, measured as the area under the curve ("AUC") of a plot of the concentration of the drug in blood (whole blood, plasma, or serum) of the subject following administration against time is selected from about 100 ng hr/ml, about 150 ng hr/ml, about 200 ng hr/ml, about 400 ng hr/ml, about 600 ng hr/ml, about 800 ng hr/ml, about 1000 ng hr/ml, about 1200 ng about 1400 ng hr/ml, about 1600 ng hr/ml, about 1800 ng hr/ml, about 2000 ng hr/ml, about 2200 ng hr/ml, about 2400 ng hr/ml, about 2600 ng hr/ml, about 2800, about 3000 ng hr/ml, about 3200 ng hr/ml, about 3400 ng hr/ml, about 3600 ng hr/ml, about 3800 ng hr/ml, about 4000 ng hr/ml, about 4200 ng hr/ml, about 4400 ng hr/ml, about 46000 ng about 4800 ng hr/ml, about 5000 ng hr/ml, about 5200 ng hr/ml, about 5400 ng hr/ml, about 5600 ng hr/ml, about 5800 ng hr/ml, about 6000 ng hr/ml, about 6200 ng about 6400 ng hr/ml, about 6600 ng hr/ml, about 6800 ng hr/ml, about 7000 ng hr/ml, about 7200 ng hr/ml, about 7400 ng hr/ml, about 7600 ng hr/ml, about 7800 ng hr/ml, and about 8000 ng hr/ml.

In another aspect, the present invention provides a method of treatment, or use of the composition to treat a disease state, which comprises administering to a subject in need of such treatment a combination of a first therapeutic agent and a second therapeutic agent, the method comprising:

(i) administering to the subject the first therapeutic agent including compound (1):

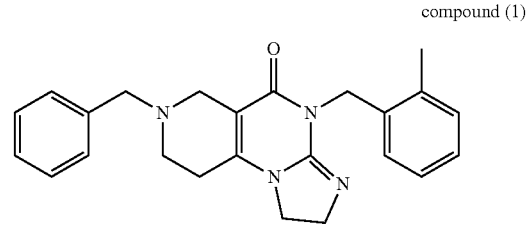 [SMILES: Cc1ccccc1CN1C(=O)C2=C(CCN(Cc3ccccc3)C2)N2CCN=C12]

compound (1)

or a pharmaceutically acceptable salt thereof;

(ii) monitoring level of compound (1) or a pharmaceutically acceptable salt thereof or a metabolite thereof in the subject using pharmacokinetic profiling; and (iii) administering the second therapeutic agent conditional on the level of the first therapeutic agent in the subject. In some embodiments of the method, the monitoring step includes constructing a pharmacokinetic profile of compound (1) or a pharmaceutically acceptable salt thereof or a metabolite thereof for the subject using concentrations of compound (1) or a pharmaceutically acceptable salt thereof or a metabolite thereof in at least two samples obtained from the subject at time points suitable to construct a pharmacokinetic profile. In some embodiments of the method, the at least two samples are collected at point-of-care or point of use by sampling or self-sampling on point-of-care devices or point of use devices or on matrices suitable for storage of the at least two samples prior to quantitation of compound (1) or a pharmaceutically acceptable salt thereof or a metabolite by a laboratory. In some embodiments of the method, each point-of-care devices or point of use devices is capable of quantitating compound (1) or a pharmaceutically acceptable salt thereof or a metabolite. In some embodiments of the method, the pharmacokinetic profile includes pharmacokinetic parameters suitable for guiding dosing of compound (1) or a pharmaceutically acceptable salt thereof for the subject. In some embodiments of the method, the at least two samples include from 2-12 samples. In some embodiments of the method, the at least two samples are collected over a time period of up to 8 hours, up to 24 hours, up to 48 hours, or up to 72 hours. In some embodiments of the method, the pharmacokinetic parameters include at least one parameter selected from the group consisting of AUC, AUCinf, Tmax, Cmax, time above threshold, steady state concentration, absorption rate, clearance rate, distribution rate, terminal T-1/2 or parameters drawn from noncompartmental pharmacokinetic (PK) or compartmental PK analysis, including physiological model-based compartmental PK analysis. In some embodiments of the method, the method of treatment further comprises generating a report including the pharmacokinetic profile of the subject. In some embodiments of the method, the report includes a recommendation regarding dosing based on the pharmacokinetic profile of the subject. In some embodiments of the method, a reduction in dosage of compound (1) or a pharmaceutically acceptable salt thereof is indicated to reduce risk of toxicity based on one or more pharmacokinetic parameters. In some embodiments of the method, the reduction in dosage of compound (1) or a pharmaceutically acceptable salt thereof is indicated based on time above threshold, wherein the threshold is the drug concentration above which toxicity occurs, or one or more of AUC, AUCinf, mean residence time (MRT), exponentials defining the pharmacokinetic profile, volume of distribution at steady state (Vss), volume of distribution during the terminal phase (Vz) or combination of a group of pharmacokinetic variable to adequately describe the pharmacokinetic profile. In some embodiments of the method, a dose adjustment of compound (1) or a pharmaceutically acceptable salt thereof is indicated to increase efficacy based on one or more pharmacokinetic parameters. In some embodiments of the method, an increase in dosage of compound (1) or a pharmaceutically acceptable salt thereof is indicated based on one or more of AUC, AUCinf, MRT, exponentials defining the pharmacokinetic profile, steady state volume (Vss) of distribution, volume of distribution during the terminal phase (Vz) or combination of a group of pharmacokinetic variables to adequately describe the pharmacokinetic profile. In some embodiments of the method, the dose of compound (1) or a pharmaceutically acceptable salt thereof is adjusted to within 5% to 25% of a desired target value. In some embodiments of the method, each of the at least two samples is applied to the point-of-care device or the point of use device for determining the concentration of the compound (1) or a pharmaceutically acceptable salt thereof or a metabolite thereof, wherein the point-of-care device or the point of use device comprises a lateral flow strip having a construction and composition such that an application of one or more of the at least two samples to the lateral flow strip causes a fraction of the drug in the sample to bind to with a component of the lateral flow strip such that a detectable signal proportional to the concentration of the drug in the applied sample is produced. In some embodiments of the method, the at least two samples are applied to matrices suitable for storage of the at least two samples prior to quantitation by a laboratory. In some embodiments of the method, the at least two samples are stored as dried blood spots. In some embodiments of the method, drug concentrations are measured by ELISA, LC MS MS, LC UV or LCMS. In some embodiments of the method, the pharmacokinetic parameters include at least one of steady state concentration, absorption, and terminal T1/2. In some embodiments of the method, at least one of the at least two samples is whole blood.

V. TNF-Related Apoptosis-Inducing Ligand ("TRAIL")

TRAIL protein can be assayed in a test sample obtained from a subject to detect TRAIL expression induced by compound (1) or a pharmaceutically acceptable salt thereof. Immunoassay methods can be used to assay TRAIL in a sample, including, but not limited to, enzyme-linked immunosorbent assay (ELISA), enzyme-linked immunofiltration assay (ELIFA), flow cytometry, immunoblot, immunoprecipitation, immunohistochemistry, immunocytochemistry, luminescent immunoassay (LIA), fluorescent immunoassay (FIA), and radioimmunoassay. Assay methods may be used to obtain qualitative and/or quantitative results. Specific details of suitable assay methods for both qualitative and quantitative assay of a sample are described in standard references, illustratively including E. Harlow and D. Lane, Antibodies: A Laboratory Manual, Cold Spring Harbor Laboratory Press, 1988; F. Breitling and S. Diibel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B. K. C. Lo, Antibody Engineering: Methods and Protocols, Methods in Molecular Biology, Humana Press, 2003; F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; Ormerod, M. G., Flow Cytometry: a practical approach, Oxford University Press, 2000; Givan, A. L., Flow Cytometry: first principles, Wiley, New York, 2001; Gorczyca, W., Flow Cytometry in Neoplastic Hematology: morphologic-immunophenotypic correlation, Taylor & Francis, 2006; Crowther, J. R., The ELISA Guidebook (Methods in Molecular Biology), Humana Press, 2000; Wild, D., The Immunoassay Handbook, 3rd Edition, Elsevier Science, 2005. and J. Sambrook and D. W. Russell, Molecular Cloning: A Laboratory Manual, Cold Spring Harbor Laboratory Press, 3rd Ed., 2001.

Examples of protocols for assaying and analyzing a sample for TRAIL for the purpose of detection of an effect of a pharmaceutical composition of the present invention are described in U.S. Patent Application No. 2012/0276088 to Wafik S. El-deiry et al., which is incorporated by reference herein in its entirety.

In some embodiments of the present invention, assays for TRAIL are used to monitor a subject. Thus, for example, a test sample is obtained from the subject before treatment with a pharmaceutical composition of the present invention and at one or more times during and/or following treatment in order to assess effectiveness of the treatment. In a further example, a test sample is obtained from the subject at various times in order to assess the course or progress of disease or healing. In one embodiment, death receptors can also be analyzed from circulating tumor cells to see if the administration of compound (1) or a pharmaceutically acceptable salt thereof increases the amount or type of death receptors.

Cancers treated using methods and compositions described herein are characterized by abnormal cell proliferation including, but not limited to, pre-neoplastic hyperproliferation, cancer in-situ, neoplasms and metastasis. Methods and compositions of the present invention can be used for prophylaxis as well as amelioration of signs and/or symptoms of cancer. The terms "treating" and "treatment" used to refer to treatment of a cancer in a subject include: preventing, inhibiting or ameliorating the cancer in the subject, such as slowing progression of the cancer and/or reducing or ameliorating a sign or symptom of the cancer. Examples of cancers treated using methods and compositions of the present invention include, but are not limited to, breast cancer, CNS cancers, colon cancer, ovarian cancer, prostate cancer, leukemia, lung cancer, and lymphoma.

VI. Multimodal Therapeutic Methods

In one aspect, the present invention is directed to multimodal therapeutic methods in which administration of compound (1) or a pharmaceutically acceptable salt thereof to a subject in need of such treatment is supplemented by administration of other therapeutic modalities. In one embodiment, the multimodal therapeutic method of the present invention comprises administering to a subject a pharmaceutical composition comprising the compound (1) or a pharmaceutically acceptable salt thereof in conjunction with radiation therapy or after radiation is determined to not have been efficacious. In one embodiment, the multimodal therapeutic method of the present invention comprises administering to a subject a pharmaceutical composition comprising compound (1) or a pharmaceutically acceptable salt thereof in conjunction with radiation therapy, wherein the pharmaceutical composition comprising compound (1) or a pharmaceutically acceptable salt thereof and the radiation therapy are administered concurrently or sequentially in any order. In one embodiment, the multimodal therapeutic method comprises administering to a subject a pharmaceutical composition comprising compound (1) or a pharmaceutically acceptable salt thereof in conjunction with radiation therapy in a sequential arrangement. In one embodiment, the multimodal therapeutic method comprises administering to a subject in need of such treatment a pharmaceutical composition comprising compound (1) or a pharmaceutically acceptable salt thereof concurrently with radiation therapy. In one embodiment, the multimodal therapeutic method of the present invention is used for the treatment of cancer. In one embodiment, the multimodal therapeutic method includes administering to a cancer subject in need of such treatment a pharmaceutical composition comprising compound (1) or a pharmaceutically acceptable salt thereof and irradiating cancer cells with a radiation beam. In one embodiment, the multimodal therapeutic method uses the technique of conformal radiotherapy (CRT) to deliver a dose volume histogram (DVH) prescribed to a cancer subject. In one embodiment, the multimodal therapeutic method uses the technique of intensity modulated radiation therapy (IMRT) to deliver radiation to cancer cells. In one embodiment, the multimodal therapeutic method uses a techniques compensates for motion of tumors in the subject during treatment (e.g., where doses of radiation must be administered to a thoracic tumor which moves as the patient breathes). In one embodiment, the multimodal therapeutic method use Four Dimensional Computed Tomography (4D CT) scanning techniques to adjust the delivered radiation field to compensate for tumor motion over the breathing cycle.

Any suitable type of radiation, including gamma radiation which is given fractionated, IMRT (intensity modulated radiation therapy), gamma knife, proton therapy and brachytherapy can be used with the multimodal therapeutic method of the present invention. Radiation therapy and compound (1) or a pharmaceutically acceptable salt thereof can be used to treat brain tumors such as glioblastoma or disease that has metastasized to the brain from lung cancer. The multimodal therapeutic method of the present invention can be used to treat lung cancer, pancreatic cancer, rectal cancer, breast cancer, sarcoma, prostate cancer, gynecological malignancies, and lymphoma. The gamma knife is used frequently to treat brain metastases. In one embodiment, the multimodal therapeutic method of the present invention includes use of proton therapy to treat cancer, including brain tumors, prostate cancer and any tumor proximate vital organs where it is very important to minimize toxicity to nearby normal tissue.

In one embodiment, the multimodal therapeutic method of the present invention eliminates minimal residual disease without adding to any toxicity resulting from treatment compound (1) or a pharmaceutically acceptable salt thereof. In one embodiment, the multimodal therapeutic method of the present invention improves prognosis and/or reduces adverse side-effects associated with a disease state or condition in a subject undergoing treatment.

VII. Synthesis of a Salt of Compound (1) and Related Analogs

The compound represented by the above compound (1) can be prepared by the synthetic process illustrated in Scheme 1 below.

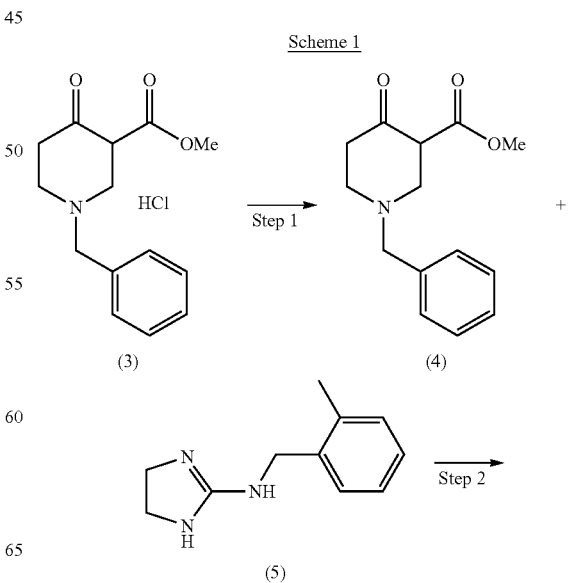

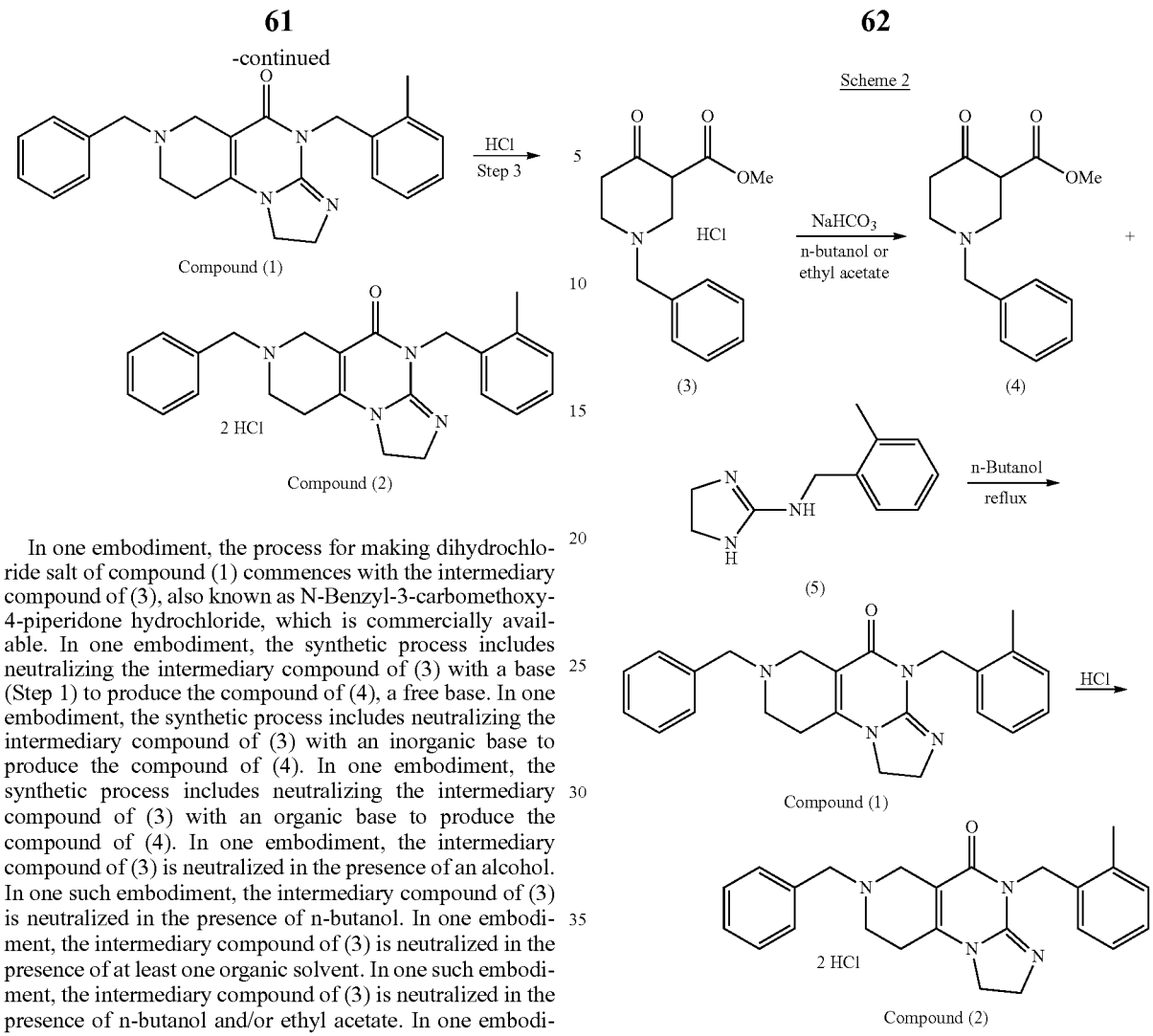

Scheme 2

Compound (1)

Compound (2)

In one embodiment, the process for making dihydrochloride salt of compound (1) commences with the intermediary compound of (3), also known as N-Benzyl-3-carbomethoxy-4-piperidone hydrochloride, which is commercially available. In one embodiment, the synthetic process includes neutralizing the intermediary compound of (3) with a base (Step 1) to produce the compound of (4), a free base. In one embodiment, the synthetic process includes neutralizing the intermediary compound of (3) with an inorganic base to produce the compound of (4). In one embodiment, the synthetic process includes neutralizing the intermediary compound of (3) with an organic base to produce the compound of (4). In one embodiment, the intermediary compound of (3) is neutralized in the presence of an alcohol. In one such embodiment, the intermediary compound of (3) is neutralized in the presence of n-butanol. In one embodiment, the intermediary compound of (3) is neutralized in the presence of at least one organic solvent. In one such embodiment, the intermediary compound of (3) is neutralized in the presence of n-butanol and/or ethyl acetate. In one embodiment, the intermediary compound of (3) is neutralized in the presence of a base and at least one organic solvent. In one such embodiment, the intermediary compound of (3) is neutralized in the presence of NaHCO3 and n-butanol. In one embodiment, the intermediary compound of (3) is neutralized in the presence of n-butanol and triethyl amine (Et3N).

In one embodiment, the synthetic process includes reacting the compound of (4) with the compound of (5) (Step 2) to produce intermediary compound of (1). In one embodiment, the reaction in Step 2 includes heating the compound of (4) with the compound of (5). In one embodiment, the reaction in Step 2 includes refluxing heating the compound of (4) and the compound of (5) in the presence of a solvent. In one embodiment, the reaction in Step 2 includes use of Dean-stark trap to remove water and/or methanol (MeOH) formed in the reaction.

In one embodiment, the synthetic process includes forming a dihydrochloride salt of the compound of (1) (Step 3). In one embodiment, the reaction in Step 3 includes treating compound of (1) with HCl in dioxane. In one embodiment, the reaction in Step 3 includes treating compound (3) with 4N HCl in dioxane.

In one embodiment, the synthetic process optionally includes recrystallization of the di-salt of compound (1).

In one preferred embodiment, the synthetic process for the preparation of the di-hydrochloride salt of compound (1) is as illustrated in the following Scheme 2.

VIII. Derivatives and Analogs of and Salts of Compound (1) and Related Compounds In one aspect, the present invention provides analogs and related salts of compound (1) and processes of making the same. Persons skilled in the art will understand that the same general principles and concepts described above in conjunction with compound (1) and salts thereof, including principles and concepts related to methods and pharmaceutical compositions, apply with equal force to derivatives and analogs of and salts of compound (1) and salts thereof.

In one embodiment, the compounds related to compound (1) have the structure of compound (10):

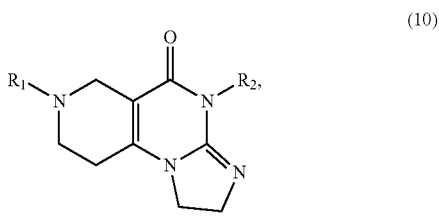

(10)

wherein $R_1$ and $R_2$ independently represent hydrogen, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In another embodiment, the compounds related to compound (1) have the structure of compound (10), wherein $R_1$ and $R_2$ are independently selected from the group consisting of H, $C_{1-4}$alkyl, $C_{1-4}$alkylphenyl, $C_{1-4}$alkylphenylketone, $C_{1-4}$benzyl-piperazine, and $C_{1-4}$alkylthienyl wherein $C_{1-4}$alkyl, $C_{1-4}$alkylphenyl, $C_{1-4}$alkylphenylketone, and $C_{1-4}$benzyl-piperazine are optionally substituted with $C_{1-4}$alkyl, hydroxyl, or halo. In still another embodiment, the compounds related to compound (1) have the structure of compound (10), wherein $R_1$ and $R_2$ are independently selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph. In some embodiments, when $R_1$ represents $CH_2Ph$, $R_2$ does not represent $CH_2$-((2-$CH_3$)-Ph).

As illustrated in Schemes 3 and 4, compound (10) can be synthesized starting either with methyl 1-$R_1$-4-oxo-3-piperidinecarboxylate (6) or by reacting compound (12) with compound (6).

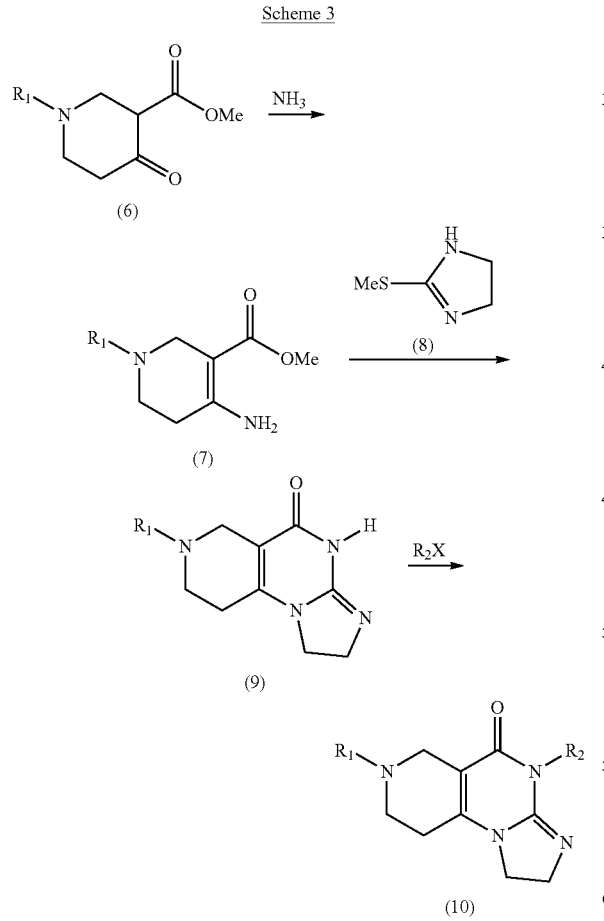

boxylate) by a reaction with ammonia. In one embodiment, compound (7) (or 4-amino-3-pyridinecarboxylic acid ester methyl ester (7)) was treated with 2-(Methylsulfanyl)-4,5-dihydro-1H-imidazole (8) to make compound (9), which when alkylated $R_2X$, wherein $R_2$ is as defined above and X is a halogen or an equivalent leaving group, produced compound (10) with different values for the $R_2$ substituent.

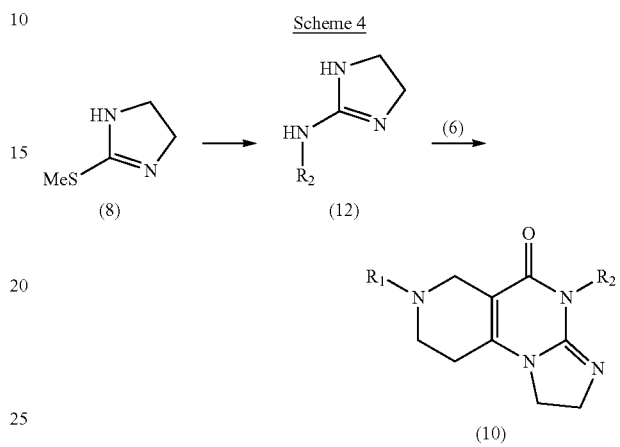

Scheme 4 illustrates the synthesis of compound (10) starting from compound (6) and compound (12). In one embodiment, as illustrated in Scheme 4, compound (12) is prepared from compound (8). In one embodiment, compound (12) was treated with compound (6) to produce compound (10) with different values for the $R_2$ substituent.

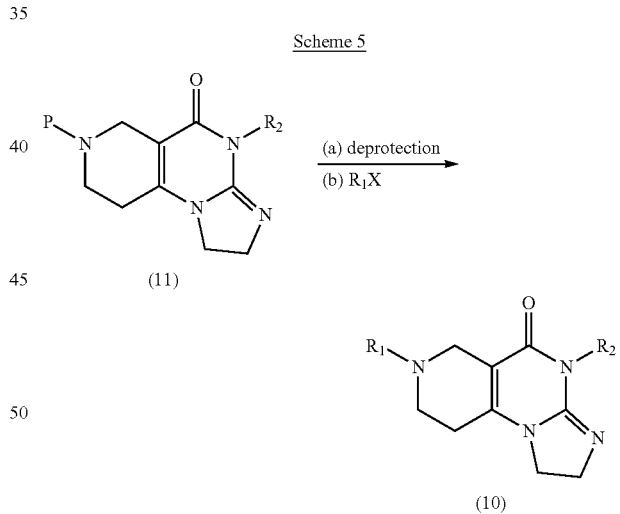

Scheme 3 illustrates the synthesis of compound (10) starting from compound (6). In one embodiment, as illustrated in Scheme 3, compound (6) was converted into 4-amino-3-pyridinecarboxylic acid ester methyl ester (7) (or methyl 4-amino-1-$R_1$-1,2,5,6-tetrahydro-3-pyridinecar- Scheme 5 illustrates the synthesis of compound (10) starting from compound (11). In one embodiment, as illustrated in Scheme 5, compound (11), having a nitrogen protecting group (P) at the N atom at ring position 7, was first deprotected and then akylated with $R_1X$, wherein $R_1$ is as defined above and X is a halogen or an equivalent leaving group, to produce compound (10) with different values for the $R_1$ substituent. In some embodiments compound (10) can be prepared as a salt, for example a 2TFA salt or 2HCl salt. In some embodiments, compound (10) can be prepared as a 2HCl salt by following a scheme analagous to Scheme 2 described above.

Examples of Compound (10)

| No. | ONC Number | R₁ | R₂ |
|---|---|---|---|
| 1 | ONC201 | CH₂Ph | CH₂-((2-CH₃)—Ph) |
| 13 | | CH₂Ph | CH₃ |
| 14 | ONC902 | CH₂Ph | CH₂-((2-Cl)—Ph) |
| 15 | ONC903 | CH₂Ph | CH₂-(2-thienyl) |
| 16 | ONC904 | CH₂Ph | CH₂CH₂Ph |
| 17 | ONC905 | CH₂Ph | CH₂CH₂(4-N-benzyl-piperazine) |
| 18 | ONC906 | CH₂Ph | CH₂-(2,4-di F—Ph) |
| 19 | ONC907 | H | CH₂-((2-CH₃)—Ph) |
| 20 | ONC908 | CH₃ | CH₂-((2-CH₃)—Ph) |
| 21 | ONC909 | CH₂CH₂Ph | CH₂-((2-CH₃)—Ph) |
| 22 | | CH₂CH₂-(4-N-benzyl-piperizine) | CH₂-((2-CH₃)—Ph) |
| 23 | | CH₂CHOHPh | CH₂-((2-CH₃)—Ph) |
| 24 | | (CH₂)₃CO—4F—Ph | CH₂-((2-CH₃)—Ph) |
| 32 | ONC910 (PV 03171) | CH₂CH₂NHCOOC(CH₃)₃ | CH₂-((2-CH₃)—Ph) |
| 33 | ONC911 (PV 03172) | CH₂CH₂CH₂NH₂ | CH₂-((2-CH₃)—Ph) |

In one embodiment, the analogs have the structure of compound (25):

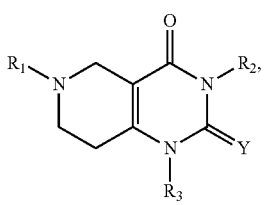

(25)

wherein Y represents $NR_4$ or O, and wherein $R_1$, $R_2$, $R_3$, and $R_4$ independently represent hydrogen, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In some embodiments, $R_1$, $R_2$, $R_3$, and $R_4$ are optionally substituted. In some embodiments, some or all hydrogens in $R_1$, $R_2$, $R_3$, and $R_4$ may be substituted by deuterium. In other embodiments, the analogs have the structure of compound (25), wherein $R_1$, $R_2$, $R_3$, and $R_4$ are independently selected from the group consisting of H, $C_{1-4}$alkyl, $C_{1-4}$alkylphenyl, $C_{1-4}$alkylphenylketone, $C_{1-4}$benzyl-piperazine, and $C_{1-4}$alkylthienyl wherein $C_{1-4}$alkyl, $C_{1-4}$alkylphenyl, $C_{1-4}$alkylphenylketone, and $C_{1-4}$benzyl-piperazine are optionally substituted with $C_{1-4}$alkyl, hydroxyl, or halo. In still other embodiments, the analogs have the structure of compound (25), wherein $R_1$, $R_2$, $R_3$, and $R_4$ are independently selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph.

In one embodiment, the analogs have the structure of compound (26):

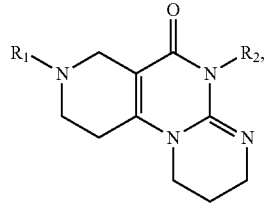

(26)

wherein $R_1$ and $R_2$, independently represent hydrogen, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In some embodiments, $R_1$ and $R_2$ are optionally substituted. In some embodiments, some or all hydrogens in $R_1$ and $R_2$ may be substituted by deuterium. In other embodiments, the analogs have the structure of compound (26), wherein $R_1$ and $R_2$ are independently selected from the group consisting of H, $C_{1-4}$alkyl, $C_{1-4}$alkylphenyl, $C_{1-4}$alkylphenylketone, $C_{1-4}$benzyl-piperazine, and $C_{1-4}$alkylthienyl wherein $C_{1-4}$alkyl, $C_{1-4}$alkylphenyl, $C_{1-4}$alkylphenylketone, and $C_{1-4}$benzyl-piperazine are optionally substituted with $C_{1-4}$alkyl, hydroxyl, or halo. In still other embodiments, the analogs have the structure of compound (26), wherein $R_1$ and $R_2$ are independently selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-(2,3,4-tri F-Ph), $CH_2$-(2,3,4,5-quadra F-Ph), $CH_2$-(penta F-Ph) $CH_2$-((2-$CH_3$)-Ph), $CH_2CHOHPh$, and $(CH_2)_3CO$-4F-Ph. In still other embodiments, the analogs have the structure of compound (26), wherein $R_1$ and $R_2$ are independently selected from the group consisting of $C_6H_4(CH_3)$, $C_6H_3(CH_3)_2$, $C_6H_2(CH_3)_3$, $C_6H(CH_3)_4$, $C_6(CH_3)_5$, $CH_2$—$C_6H_4(CH_3)$, $CH_2$—$C_6H_3(CH_3)_2$, $CH_2$—$C_6H_2(CH_3)_3$, $CH_2$—$C_6H(CH_3)_4$, $CH_2$—$C_6(CH_3)_5$. In still other embodiments, the analogs have the structure of compound (26), wherein $R_1$ and $R_2$ are independently selected from the group consisting of $C_6H_4(OH)$, $C_6H_3(OH)_2$, $C_6H_2(OH)_3$, $C_6H(OH)_4$, $C_6(OH)_5$, $CH_2$—$C_6H_4(OH)$, $CH_2$—$C_6H_3(OH)_2$, $CH_2$—$C_6H_2(OH)_3$, $CH_2$—$C_6H(OH)_4$, $CH_2$—$C_6(OH)_5$.

In one embodiment, the analogs have the structure of compound (27):

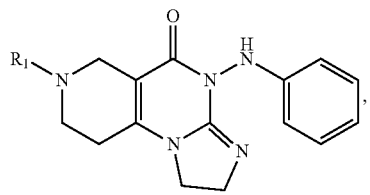

(27)

wherein $R_1$ represents hydrogen, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In some embodiments, $R_1$ is optionally substituted. In some embodiments, some or all hydrogens in $R_1$ may be substituted by deuterium. In other embodiments, the analogs have the structure of compound (27), wherein $R_1$ is selected from the group consisting of H, $C_{1-4}$alkyl, $C_{1-4}$ alkylphenyl, $C_{1-4}$alkylphenylketone, $C_{1-4}$benzyl-piperazine, and $C_{1-4}$alkylthienyl wherein $C_{1-4}$alkyl, $C_{1-4}$alkylphenyl, $C_{1-4}$alkylphenylketone, and $C_{1-4}$benzyl-piperazine are optionally substituted with $C_{1-4}$alkyl, hydroxyl, or halo. In still other embodiments, the analogs have the structure of compound (27), wherein $R_1$ is selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph.

In one embodiment, the analogs have the structure of compound (28):

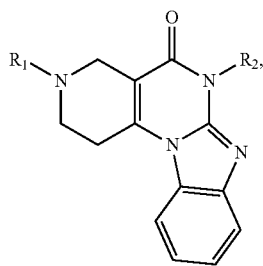

(28)

wherein $R_1$, and $R_2$ independently represent hydrogen, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In some embodiments, $R_1$ and $R_2$ are optionally substituted. In some embodiments, some or all hydrogens in $R_1$ and $R_2$ may be substituted by deuterium. In other embodiments, the analogs have the structure of compound (28), wherein $R_1$ and $R_2$ are independently selected from the group consisting of H, $C_{1-4}$alkyl, $C_{1-4}$alkylphenyl, $C_{1-4}$alkylphenylketone, $C_{1-4}$benzyl-piperazine, and $C_{1-4}$alkylthienyl wherein $C_{1-4}$ alkyl, $C_{1-4}$ alkylphenyl, $C_{1-4}$alkylphenylketone, and $C_{1-4}$benzyl-piperazine are optionally substituted with $C_{1-4}$alkyl, hydroxyl, or halo. In still other embodiments, the analogs have the structure of compound (28), wherein $R_1$ and $R_2$ are independently selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph.

In one embodiment, the analogs have the structure of compound (29):

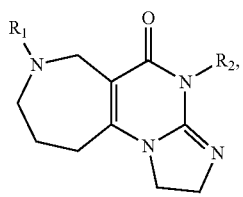

(29)

wherein $R_1$, and $R_2$ independently represent hydrogen, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In some embodiments, $R_1$ and $R_2$ are optionally substituted. In some embodiments, some or all hydrogens in $R_1$ and $R_2$ may be substituted by deuterium. In other embodiments, the analogs have the structure of compound (29), wherein $R_1$ and $R_2$ are independently selected from the group consisting of H, $C_{1-4}$alkyl, $C_{1-4}$alkylphenyl, $C_{1-4}$alkylphenylketone, $C_{1-4}$benzyl-piperazine, and $C_{1-4}$alkylthienyl wherein $C_{1-4}$alkyl, $C_{1-4}$alkylphenyl, $C_{1-4}$alkylphenylketone, and $C_{1-4}$benzyl-piperazine are optionally substituted with $C_{1-4}$alkyl, hydroxyl, or halo. In still other embodiments, the analogs have the structure of compound (29), wherein $R_1$ and $R_2$ are independently selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph.

In one embodiment, the analogs have the structure of compound (30):

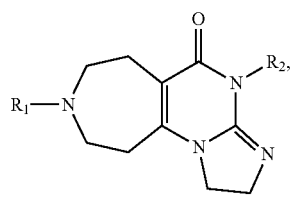

(30)

wherein $R_1$, and $R_2$ independently represent hydrogen, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In some embodiments, $R_1$ and $R_2$ are optionally substituted. In some embodiments, some or all hydrogens in $R_1$ and $R_2$ may be substituted by deuterium. In other embodiments, the analogs have the structure of compound (30), wherein $R_1$ and $R_2$ are independently selected from the group consisting of H, $C_{1-4}$alkyl, $C_{1-4}$alkylphenyl, $C_{1-4}$alkylphenylketone, $C_{1-4}$benzyl-piperazine, and $C_{1-4}$alkylthienyl wherein $C_{1-4}$alkyl, $C_{1-4}$alkylphenyl, $C_{1-4}$alkylphenylketone, and $C_{1-4}$benzyl-piperazine are optionally substituted with $C_{1-4}$alkyl, hydroxyl, or halo. In still other embodiments, the analogs have the structure of compound (30), wherein $R_1$ and $R_2$ are independently selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph.

In one embodiment, the analogs have the structure of compound (31):

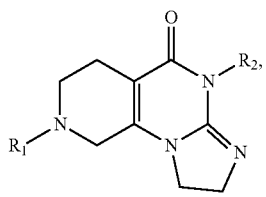

(31)

wherein $R_1$, and $R_2$ independently represent hydrogen, alkyl, cycloalkyl, cycloalkylalkyl, carboxyl, haloalkyl, alkenyl, cycloalkenyl, alkynyl, aryl, aralkyl, hydroxyalkyl, alkoxy, aryloxy, alkoxyalkyl, alkoxycarbonyl, aralkoxy, aralkylthio, alkanoyl, mercapto, alkylthio, arylthio, alkylsulfinyl, arylsulfinyl, alkylsulfonyl, arylsulfonyl, heteroaryl, acyl, and heterocycle radicals. In some embodiments, $R_1$ and $R_2$ are optionally substituted. In some embodiments, some or all hydrogens in $R_1$ and $R_2$ may be substituted by deuterium. In other embodiments, the analogs have the structure of compound (31), wherein $R_1$ and $R_2$ are independently selected from the group consisting of H, $C_{1-4}$alkyl, $C_{1-4}$alkylphenyl, $C_{1-4}$alkylphenylketone, $C_{1-4}$benzyl-piperazine, and $C_{1-4}$alkylthienyl wherein $C_{1-4}$alkyl, $C_{1-4}$alkylphenyl, $C_{1-4}$alkylphenylketone, and $C_{1-4}$benzyl-piperazine are optionally substituted with $C_{1-4}$alkyl, hydroxyl, or halo. In still other embodiments, the analogs have the structure of compound (31), wherein $R_1$ and $R_2$ are independently selected from the group consisting of H, $CH_3$, $CH_2Ph$, $CH_2$-((2-Cl)-Ph), $CH_2$-(2-thienyl), $CH_2CH_2Ph$, $CH_2CH_2$(4-N-benzyl-piperazine), $CH_2$-(2,4-di F-Ph), $CH_2$-((2-$CH_3$)-Ph), $CH_2CHOHPh$, and $(CH_2)_3CO$-4F-Ph.

IX. Examples

It should be understood that the description and specific examples provided below are intended for purposes of illustration only and are not intended to limit the scope of the present disclosure. Examples 1 to 2 illustrate synthesis of dihydrochloride salt of compound (1) starting from compound (1). In these examples and throughout the application the dihydrochloride salt of compound (1) is referred to as compound (2). The following examples are intended to illustrate the embodiments disclosed and are not to be construed as being limitations thereto. Additional compounds, other than those described below, may be prepared using the following reaction schemes described above or appropriate variations or modifications thereof.

Example 1

Synthesis of 2-Chlorobenzylamino-2-imidazoline hydriodide

To a stirred solution of 2-methylthio-2-imidazoline hydriodide (244 mg, 1.00 mMol) in dry dioxane (2.0 mL) was added 2-chlorobenzylamine (141 mg, 1.0 mMol). The reaction mixture was stirred for 90 min at 70 C. under an atmosphere of argon. The solution was cooled to room temperature, filtered on a sintered funnel, washed with cold dioxane (2 mL) and dried under vacuum. The white solid compound 4●HI ($R_2$=2-chlorobenzyl) was obtained (242 mg, 72%) and used without further purification.

Example 2

Synthesis of 2-Chlorobenzylamino-2-imidazoline

To a stirred solution of 2-chlorobenzylamino-2-imidazoline hydriodide (242 mg, 0.72 mMol) in water (3 mL), was added 1.0 N sodium hydroxide (2 mL) at 7° C. The reaction mixture was stirred for 30 min at 7° C. under argon. After that methylene chloride (5 mL) was added and the mixture stirred for another 5 min. The reaction mixture was extracted with methylene chloride (2×2.5 mL), The organic layer was dried over anhydrous $Na_2SO_4$, filtered and evaporated. The resulting free base (150 mg, 100%) was obtained as a viscous liquid and was used for the next reaction without any further purification. MS(ESI) 210(M+H).

Example 3

Synthesis of Methyl-1-benzyl 4-oxo-3-piperidine carboxylate (Compound (6))

To a stirred methyl-1-benzyl 4-oxo-3-piperidine carboxylate hydrochloride (5.7 g, 20 mMol) in ethyl acetate (50 mL), was added triethylamine (6 mL) at 7° C. The reaction mixture was stirred for 30 min at 7° C. under atmosphere of argon. The reaction mixture was extracted with ethyl acetate (2×50 mL) washed with water (50 mL). The organic layer was dried over anhydrous $Na_2SO_4$, filtered and evaporated. The resulting free base residue (5, $R_1$=benzyl) as a viscous oil was used in the next reaction without any further purification MS(ESI) 248(M+H)

Example 4

Synthesis of ONC902 (Compound (14))

To a solution of 2-chlorobenzylamino-2-imidazoline (150 mg, 0.72 mMol), methyl 1-benzyl 4-oxo-3-piperidine carboxylate (5, $R_1$=benzyl) (195 mg, 0.79 mMol) in 1-butanol (2 mL) was added PPTS (10 mg) and the mixture was stirred at room temperature for 48 h. After that the reaction mixture was refluxed at 125° C. to 130° C. for 2 h. The solvents were removed under vacuum, extracted with ethyl acetate (10 mL), washed with saturated sodium bicarbonate solution (2×10 mL) and water (10 mL). The organic layer was dried over anhydrous $Na_2SO_4$, filtered and evaporated. The crude free base was purified by RP HPLC (10%-40% acetonitrile/water) to give ONC902 TFA salt as a white solid (228 mg, 50% yield) MS(ESI) 407 (M+H).

The same process was used starting with different benzylamines to prepare various analogs, e.g., ONC903, 904, 905, and 906.

Example 5

Synthesis of ONC907 (Compound (19))

To a suspension of 60% sodium hydride (3.5 g, 88 mMol) in dry toluene (50 mL), dimethyl carbonate (4.32 g, 48.0 mMol) was added dropwise in 0.5 h at room temperature under an atmosphere of nitrogen. After addition of a few drops of methanol, a solution of 1-tert-butoxycarbonyl-4-piperidone (4.8 g, 24 mMol) dissolved in dry toluene (20 mL) was added dropwise to the reaction mixture while stirring at 80° C. over 1 h. The reaction mixture was stirred for 3 h at the same temperature and then cooled to 0° C. (ice bath) and adjusted to pH 6-6.5 with acetic acid. The resulting cold mixture was diluted with water (10 mL) and adjusted to pH 8 with 5% sodium hydroxide solution. The toluene layer was separated and the aqueous layer was extracted with toluene (20 mL). The combined organic layer was dried over anhydrous sodium sulfate, and concentrated under reduced pressure The compound was dried in vacuum to give methyl-1-tert-butoxycarbonyl-4-oxo-3-piperidine carboxylate (5.0 g, 80%). The compound obtained was carried to next reaction without any further purification.

2-methybenzylamino-2-imidazoline (190 mg, 1 mMol), methyl 1-tert-butoxycarbonyl-4-oxo-3-piperidine carboxylate (315 mg, 1.1 mMol) in 1-butanol (2 mL) was added PPTS (10.0 mg) and the mixture was stirred at room temperature for 48 h. After that the reaction mixture was refluxed at 125° C. to 130° C. for 2 h. The solvents were removed under vacuum, extracted with ethyl acetate (10 mL), washed with saturated sodium bicarbonate solution (2×10 mL) and water (10 mL). The organic layer was dried over anhydrous $Na_2SO_4$, filtered and evaporated. The crude free base was cleaved with 10% trifluoroacetic acid in dichloromethane, purified by RP HPLC (10%-40% acetonitrile/water) to give ONC907 (262 mg, 50%) TFA salt as a white solid MS(ESI) 297 (M+H).

Example 6

Synthesis of ONC909 (Compound 21)

A mixture of ONC907 (100 mg, 0.2 mMol), phenylethyl bromide (55.0 mg, 0.28 mMol) and potassium carbonate (150 mg, 1.0 mMol) in N,N-dimethylformamide (3 mL) was heated to 70° C. for 12 h. The solvents were removed under vacuum, extracted with ethyl acetate (10 mL), washed with water (5 mL). The organic layer was dried over anhydrous $Na_2SO_4$, filtered and evaporated. The crude free base was purified by RP HPLC (10%-40% acetonitrile/water) to give ONC909 (62 mg, 50%) TFA salt as a white solid MS(ESI) 401 (M+H).

Example 7

Synthesis of ONC908 (Compound 20)

To a solution of 2-methylbenzylamino-2-imidazoline (190.0 mg, 1.0 mmol), methyl 1-methyl 4-oxo-3-piperidine carboxylate (185.0 mg, 1.0 mMol) in 1-butanol (2.0 mL) was added PPTS (10.0 mg) and the mixture was stirred at room temperature for 48 h. After that the reaction mixture was refluxed at 125° C. to 130° C. for 2 h. The solvents were removed under vacuum, extracted with ethyl acetate (10 mL), washed with saturated sodium bicarbonate solution (2×10 ml) and water (10 mL). The organic layer was dried over anhydrous $Na_2SO_4$, filtered and evaporated. The crude free base was purified by HPLC 10%-40% acetonitrile and water to give ONC908 (270.0 mg, 50%) TFA salt as a white solid MS(ESI) 311 (M+H).

Example 8

Synthesis of ONC201 (Compound 1)

To a stirred 800 mL saturated $NaHCO_3$ in a 2 L round bottom flask, compound (3) (239.7 g, 0.845 mol, 1.6 equiv) was added in portions. n-Butanol (500 mL) was added to the resulting mixture and the mixture was stirred for 30 min and then transferred to a separating funnel. The organic phase, containing compound (4), was separated and transferred to a 2 L three-neck round bottom flask equipped with mechanical stirring, $N_2$ inlet, a thermocouple, a condenser and a Dean-Stark trap. Compound (5) (100 g, 0.528 mol, 1 equiv) and pyridinium p-toluenesulfonate (PPTS) (6.63 gm 0.026 mol, 5 mol %) were added to the contents of the flask. The resulting mixture was heated to reflux for 6 hours. Water in the reaction mixture was separated into the Dean-Stark trap as necessary. Refluxing temperature increased from 93° C. to 118° C. Reaction progress was monitored by HPLC. When the peak area of compound (1) on HPLC remained constant with the reaction time, the reaction was stopped.

Example 9

Synthesis of Di-Salt of ONC201 (Compound (2))

Without isolation of the compound (1), the reaction mixture from EXAMPLE 8 was washed with 500 mL of water and diluted with methyl tert-butyl ether (MTBE) (800 mL). The organic phase was washed with water (500 mL×2) and transferred to a 3 L three-neck round bottom flask equipped with mechanical stirring, N2 inlet, a thermocouple, a condenser and a Dean-Stark trap. While agitating the reaction mixture, 1 N HCl in dioxane-MTBE solution was added dropwise (4 N HCl in dioxane: 300 mL, 1.2 mol, 2.27 equiv; MTBE: 1200 mL) until no more solid precipitated out of the reaction mixture upon addition of HCl. The reaction mixture was heated to reflux at 60-65° C. for 2 hours. Water was separated into the Dean-Stark trap as necessary. Upon cooling to room temperature, the solid precipitate was filtered through a sintered glass funnel and washed with n-butanol-MTBE (1:2, 600 mL) and MTBE (600 mL) respectively. The solid was dried in the vacuum oven at 65° C. overnight (16 hours) to afford 200 g yellow solid.

To a 2 L three-neck round bottom flask equipped with mechanical stirring, N2 inlet, a thermocouple and a condenser, the above solid (200 g) was added, followed by ethanol (1000 mL). The mixture was heated to reflux at 78° C. for 2 hours. Upon cooling to room temperature, the solid was filtered through a sintered glass funnel and washed with ethanol (200 mL×3). The wet solid was dried in the vacuum oven at 85° C. for 3 days until the residual solvent met specification. 120 g of compound (2) was obtained as a white solid in a yield of 49%, with HPLC purity 99.7%.

It will be appreciated by those skilled in the art that changes could be made to the exemplary embodiments shown and described above without departing from the broad inventive concept thereof. It is understood, therefore, that this invention is not limited to the exemplary embodiments shown and described, but it is intended to cover modifications within the spirit and scope of the present invention as defined by the claims. For example, specific features of the exemplary embodiments may or may not be part of the claimed invention and features of the disclosed embodiments may be combined. Unless specifically set forth herein, the terms "a", "an" and "the" are not limited to one element but instead should be read as meaning "at least one".

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

Further, to the extent that the method does not rely on the particular order of steps set forth herein, the particular order of the steps should not be construed as limitation on the claims. The claims directed to the method of the present invention should not be limited to the performance of their steps in the order written, and one skilled in the art can readily appreciate that the steps may be varied and still remain within the spirit and scope of the present invention.

All references, including publications, patent applications, and patents, cited herein are hereby incorporated by reference to the same extent as if each reference were individually and specifically indicated to be incorporated by reference and were set forth in its entirety herein.

The invention claimed is:

1. A method of treatment, comprising administering to a subject in need of such treatment a therapeutic agent comprising compound (1):

Compound (1)

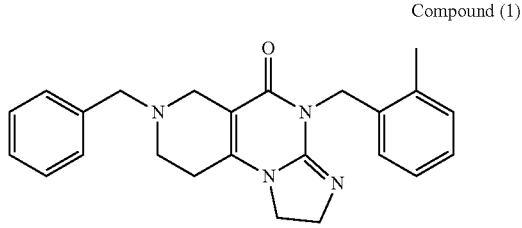 [SMILES: Cc1ccccc1CN1C(=O)C2=C(CCN(Cc3ccccc3)C2)N2CCN=C12]

or a pharmaceutically acceptable salt thereof, wherein the treatment is for Leukemia.

2. A method of treatment, comprising administering to a subject in need of such treatment a first therapeutic agent comprising compound (1):

Compound (1)

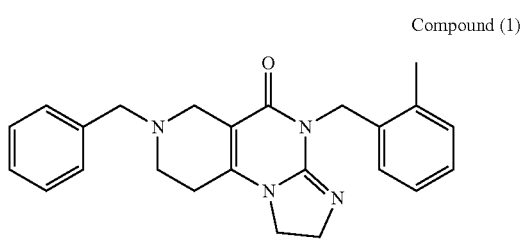 [SMILES: Cc1ccccc1CN1C(=O)C2=C(CCN(Cc3ccccc3)C2)N2CCN=C12]

or a pharmaceutically acceptable salt thereof, wherein the treatment is for an acute leukemia.

3. The method according to claim 2, wherein the acute leukemia is selected from group consisting of acute lymphocyte leukemia, acute myeloid leukemia, chronic myeloid leukemia, myelodysplastic syndrome, and myeloproliferative disease.

4. A method of treatment comprising administering to a subject having leukemia a pharmaceutically acceptable amount of compound (1):

Compound (1)

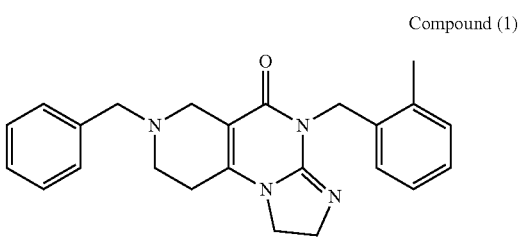 [SMILES: Cc1ccccc1CN1C(=O)C2=C(CCN(Cc3ccccc3)C2)N2CCN=C12]

or a pharmaceutically acceptable salt thereof, wherein the pharmaceutically acceptable amount of compound (1) is administered as a salvage therapy.

* * * * *